(12) United States Patent
Meinicke et al.

(10) Patent No.: US 12,364,700 B2
(45) Date of Patent: *Jul. 22, 2025

(54) MEDICAL USE OF PHARMACEUTICAL COMBINATION OR COMPOSITION

(71) Applicant: Boehringer Ingelheim International GmbH, Ingelheim am Rhein (DE)

(72) Inventors: Thomas Meinicke, Mittelbiberach (DE); Maximilian Von Eynatten, Wiesbaden (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/230,693

(22) Filed: Aug. 7, 2023

(65) Prior Publication Data

US 2023/0381188 A1 Nov. 30, 2023

Related U.S. Application Data

(63) Continuation of application No. 17/209,365, filed on Mar. 23, 2021, now abandoned, which is a continuation of application No. 16/788,608, filed on Feb. 12, 2020, now abandoned, which is a continuation of application No. 16/170,134, filed on Oct. 25, 2018, now abandoned, which is a continuation of application No. 15/616,974, filed on Jun. 8, 2017, now Pat. No. 10,155,000.

(51) Int. Cl.
| | |
|---|---|
| A61K 31/522 | (2006.01) |
| A61K 9/00 | (2006.01) |
| A61K 9/20 | (2006.01) |
| A61K 31/155 | (2006.01) |
| A61K 31/50 | (2006.01) |
| A61K 45/06 | (2006.01) |

(52) U.S. Cl.
CPC .............. *A61K 31/522* (2013.01); *A61K 9/00* (2013.01); *A61K 9/0053* (2013.01); *A61K 9/20* (2013.01); *A61K 9/2018* (2013.01); *A61K 31/155* (2013.01); *A61K 45/06* (2013.01); *A61K 31/50* (2013.01)

(58) Field of Classification Search
CPC ..... A61K 31/522; A61K 31/155; A61K 45/06
See application file for complete search history.

(56) References Cited

U.S. PATENT DOCUMENTS

| | | |
|---|---|---|
| 2,056,046 A | 9/1936 | Fourneau |
| 2,375,138 A | 5/1945 | Victors |
| 2,629,736 A | 2/1953 | Krimmel |
| 2,730,544 A | 1/1956 | Sahyun |
| 2,750,387 A | 6/1956 | Krimmel |
| 2,928,833 A | 3/1960 | Leake et al. |
| 3,174,901 A | 3/1965 | Sterne |
| 3,236,891 A | 2/1966 | Seemuller |
| 3,454,635 A | 7/1969 | Muth |
| 3,673,241 A | 6/1972 | Marxer |
| 3,925,357 A | 12/1975 | Okada et al. |
| 4,005,208 A | 1/1977 | Bender et al. |
| 4,061,753 A | 12/1977 | Bodor et al. |
| 4,159,345 A | 6/1979 | Takeo et al. |
| 4,382,091 A | 5/1983 | Benjamin et al. |
| 4,599,338 A | 7/1986 | Regnier et al. |
| 4,639,436 A | 1/1987 | Junge et al. |
| 4,687,777 A | 8/1987 | Meguro et al. |
| 4,743,450 A | 5/1988 | Harris et al. |
| 4,764,466 A | 8/1988 | Suyama et al. |
| 4,816,455 A | 3/1989 | Schickaneder et al. |
| 4,873,330 A | 10/1989 | Lindholm |
| 4,968,672 A | 11/1990 | Jacobson et al. |
| 5,034,225 A | 7/1991 | Bennett et al. |
| 5,041,448 A | 8/1991 | Janssens et al. |
| 5,051,509 A | 9/1991 | Nagano et al. |
| 5,051,517 A | 9/1991 | Findeisen et al. |
| 5,084,460 A | 1/1992 | Munson, Jr. et al. |
| 5,120,712 A | 6/1992 | Habener |
| 5,130,244 A | 7/1992 | Nishimaki et al. |
| 5,164,526 A | 11/1992 | Macher |
| 5,219,870 A | 6/1993 | Kim |
| 5,223,499 A | 6/1993 | Greenlee et al. |
| 5,234,897 A | 8/1993 | Findeisen et al. |
| 5,258,380 A | 11/1993 | Janssens et al. |
| 5,266,555 A | 11/1993 | Findeisen et al. |
| 5,273,995 A | 12/1993 | Roth |
| 5,284,967 A | 2/1994 | Macher |
| 5,300,298 A | 4/1994 | LaNoue |
| 5,329,025 A | 7/1994 | Wong et al. |
| 5,332,744 A | 7/1994 | Chakravarty et al. |

(Continued)

FOREIGN PATENT DOCUMENTS

| | | |
|---|---|---|
| AU | 2003280680 A1 | 6/2004 |
| AU | 2009224546 A1 | 9/2009 |

(Continued)

OTHER PUBLICATIONS

Haak, Initial Combination of linagliptin and metformin improves glycemic control in type 2 diabetes, Diabetes, Obesity and Metabolism, vol. 14, 2012, p. 565-574.

Hainer, Vojtech MD, PHD "Comparative Efficiency and Safety of Pharmacological Approaches to the Management of Obesity." Diabetes Care, 2011, vol. 34, Suppl. 2, pp. S349-S354.

(Continued)

*Primary Examiner* — Kevin E Weddington
(74) *Attorney, Agent, or Firm* — David L. Kershner

(57) ABSTRACT

The present invention relates to a certain DPP-4 inhibitor for use in combination with metformin in CKD patients.

18 Claims, No Drawings

(56) References Cited

U.S. PATENT DOCUMENTS

| | | |
|---|---|---|
| 5,389,642 A | 2/1995 | Dorsch et al. |
| 5,399,578 A | 3/1995 | Buhlmayer et al. |
| 5,407,929 A | 4/1995 | Takahashi et al. |
| 5,461,066 A | 10/1995 | Gericke et al. |
| 5,470,579 A | 11/1995 | Bonte et al. |
| 5,591,762 A | 1/1997 | Hauel et al. |
| 5,594,003 A | 1/1997 | Hauel et al. |
| 5,602,127 A | 2/1997 | Hauel et al. |
| 5,614,519 A | 3/1997 | Hauel et al. |
| 5,719,279 A | 2/1998 | Kufner-Muhl et al. |
| 5,728,849 A | 3/1998 | Bouchard et al. |
| 5,753,635 A | 5/1998 | Buckman et al. |
| 5,777,115 A | 7/1998 | Leigh et al. |
| 5,830,908 A | 11/1998 | Grunenberg et al. |
| 5,879,708 A | 3/1999 | Makino et al. |
| 5,958,951 A | 9/1999 | Ahrndt et al. |
| 5,965,555 A | 10/1999 | Gebert et al. |
| 5,965,592 A | 10/1999 | Buhlmayer et al. |
| 6,011,049 A | 1/2000 | Whitcomb |
| 6,107,302 A | 8/2000 | Carter et al. |
| 6,166,063 A | 12/2000 | Villhauer |
| 6,200,958 B1 | 3/2001 | Odaka et al. |
| 6,248,758 B1 | 6/2001 | Klokkers et al. |
| 6,303,661 B1 | 10/2001 | Demuth et al. |
| 6,342,601 B1 | 1/2002 | Bantick et al. |
| 6,372,940 B1 | 4/2002 | Cavazza |
| 6,399,101 B1 | 6/2002 | Frontanes et al. |
| 6,448,323 B1 | 9/2002 | Jordan et al. |
| 6,548,481 B1 | 4/2003 | Demuth et al. |
| 6,579,868 B1 | 6/2003 | Asano et al. |
| 6,689,353 B1 | 2/2004 | Wang et al. |
| 6,699,845 B2 | 3/2004 | Asahi |
| 6,727,261 B2 | 4/2004 | Gobbi et al. |
| 6,784,195 B2 | 8/2004 | Hale et al. |
| 6,821,978 B2 | 11/2004 | Chackalamannil et al. |
| 6,869,947 B2 | 3/2005 | Kanstrup et al. |
| 6,890,898 B2 | 5/2005 | Bachovchin et al. |
| 6,995,183 B2 | 2/2006 | Hamann et al. |
| 7,034,039 B2 | 4/2006 | Oi et al. |
| 7,060,722 B2 | 6/2006 | Kitajima et al. |
| 7,074,794 B2 | 7/2006 | Kitajima et al. |
| 7,074,798 B2 | 7/2006 | Yoshikawa et al. |
| 7,074,923 B2 | 7/2006 | Dahanukar et al. |
| 7,109,192 B2 | 9/2006 | Hauel et al. |
| 7,179,809 B2 | 2/2007 | Eckhardt et al. |
| 7,183,280 B2 | 2/2007 | Himmelsbach et al. |
| 7,192,952 B2 | 3/2007 | Kanstrup et al. |
| 7,217,711 B2 | 5/2007 | Eckhardt et al. |
| 7,220,750 B2 | 5/2007 | Himmelsbach et al. |
| 7,235,538 B2 | 6/2007 | Kanstrup et al. |
| 7,247,478 B2 | 7/2007 | Eberhardt et al. |
| 7,282,219 B2 | 10/2007 | Nomura et al. |
| 7,291,642 B2 | 11/2007 | Kauffmann-Hefner et al. |
| 7,361,687 B2 | 4/2008 | Barth et al. |
| 7,393,847 B2 | 7/2008 | Eckhardt et al. |
| 7,407,955 B2 | 8/2008 | Himmelsbach et al. |
| 7,432,262 B2 | 10/2008 | Eckhardt et al. |
| 7,439,370 B2 | 10/2008 | Eckhardt |
| 7,470,716 B2 | 12/2008 | Eckhardt et al. |
| 7,476,671 B2 | 1/2009 | Eckhardt et al. |
| 7,482,337 B2 | 1/2009 | Himmelsbach et al. |
| 7,495,002 B2 | 2/2009 | Langkopf et al. |
| 7,495,003 B2 | 2/2009 | Eckhardt et al. |
| 7,495,005 B2 | 2/2009 | Himmelsbach et al. |
| 7,501,426 B2 | 3/2009 | Himmelsbach et al. |
| 7,550,455 B2 | 6/2009 | Himmelsbach et al. |
| 7,560,450 B2 | 7/2009 | Eckhardt et al. |
| 7,566,707 B2 | 7/2009 | Eckhardt et al. |
| 7,569,574 B2 | 8/2009 | Maier et al. |
| 7,579,449 B2 | 8/2009 | Eckhardt et al. |
| 7,610,153 B2 | 10/2009 | Carter, Jr. et al. |
| 7,645,763 B2 | 1/2010 | Himmelsbach et al. |
| 7,718,666 B2 | 5/2010 | Boehringer et al. |
| 7,754,481 B2 | 7/2010 | Eberhardt et al. |
| 7,799,782 B2 | 9/2010 | Munson et al. |
| 7,820,815 B2 | 10/2010 | Pfrengle et al. |
| 7,838,529 B2 | 11/2010 | Himmelsbach et al. |
| 7,919,572 B2 | 4/2011 | Angot et al. |
| 8,039,477 B2 | 10/2011 | Hendrix et al. |
| 8,071,583 B2 | 12/2011 | Himmelsbach |
| 8,106,060 B2 | 1/2012 | Pfrengle et al. |
| 8,119,648 B2 | 2/2012 | Himmelsbach et al. |
| 8,158,633 B2 | 4/2012 | Hendrix et al. |
| 8,178,541 B2 | 5/2012 | Himmelsbach et al. |
| 8,232,281 B2 | 7/2012 | Dugi et al. |
| 8,338,450 B2 | 12/2012 | Arora et al. |
| 8,399,414 B2 | 3/2013 | Harada et al. |
| 8,455,435 B2 | 6/2013 | Franz et al. |
| 8,513,264 B2 | 8/2013 | Mark et al. |
| 8,541,450 B2 | 9/2013 | Pfrengle et al. |
| 8,637,530 B2 | 1/2014 | Pfrengle et al. |
| 8,664,232 B2 | 3/2014 | Himmelsbach et al. |
| 8,673,927 B2 | 3/2014 | Dugi et al. |
| 8,679,520 B2 | 3/2014 | Horres et al. |
| 8,697,868 B2 | 4/2014 | Himmelsbach et al. |
| 8,785,455 B2 | 7/2014 | Hotter et al. |
| 8,846,695 B2 | 9/2014 | Dugi |
| 8,853,156 B2 | 10/2014 | Dugi et al. |
| 8,865,729 B2 | 10/2014 | Sieger et al. |
| 8,883,800 B2 | 11/2014 | Pfrengle et al. |
| 8,883,805 B2 | 11/2014 | Pfrengle et al. |
| 8,962,636 B2 | 2/2015 | Pfrengle et al. |
| 9,034,883 B2 | 5/2015 | Klein et al. |
| 9,108,964 B2 | 8/2015 | Himmelsbach et al. |
| 9,149,478 B2 | 10/2015 | Klein et al. |
| 9,155,705 B2 | 10/2015 | Friedl et al. |
| 9,173,859 B2 | 11/2015 | Dugi et al. |
| 9,186,392 B2 | 11/2015 | Klein et al. |
| 9,199,998 B2 | 12/2015 | Pfrengle et al. |
| 9,212,183 B2 | 12/2015 | Sieger et al. |
| 9,266,888 B2 | 2/2016 | Sieger et al. |
| 9,321,791 B2 | 4/2016 | Himmelsbach et al. |
| 9,415,016 B2 | 8/2016 | Friedl et al. |
| 9,486,426 B2 | 8/2016 | Eller |
| 9,457,029 B2 | 10/2016 | Dugi et al. |
| 9,486,526 B2 | 11/2016 | dugi |
| 9,493,462 B2 | 11/2016 | Sieger |
| 9,815,837 B2 | 11/2017 | Sieger |
| 10,023,574 B2 | 7/2018 | Himmelsbach |
| 10,034,877 B2 | 7/2018 | dugi |
| 10,092,571 B2 | 10/2018 | Dugi et al. |
| 10,155,000 B2 * | 12/2018 | Meinicke ............ A61K 9/0053 |
| 10,301,313 B2 | 5/2019 | Sieger et al. |
| 10,973,827 B2 | 4/2021 | Friedl et al. |
| 11,033,552 B2 | 6/2021 | Kohlrausch et al. |
| 2001/0020006 A1 | 9/2001 | Demuth et al. |
| 2001/0051646 A1 | 12/2001 | Demuth et al. |
| 2002/0019411 A1 | 2/2002 | Robl et al. |
| 2002/0042393 A1 | 4/2002 | Oobae et al. |
| 2002/0049164 A1 | 4/2002 | Demuth et al. |
| 2002/0115718 A1 | 8/2002 | Chen et al. |
| 2002/0137903 A1 | 9/2002 | Ellsworth et al. |
| 2002/0160047 A1 | 10/2002 | Hussain et al. |
| 2002/0161001 A1 | 10/2002 | Kanstrup et al. |
| 2002/0169174 A1 | 11/2002 | Chackalamannil et al. |
| 2002/0198205 A1 | 12/2002 | Himmelsbach et al. |
| 2003/0040490 A1 | 2/2003 | Sugiyama et al. |
| 2003/0078269 A1 | 4/2003 | Pearson et al. |
| 2003/0100563 A1 | 5/2003 | Edmondson et al. |
| 2003/0104053 A1 | 6/2003 | Gusler et al. |
| 2003/0104983 A1 | 6/2003 | DeFelippis et al. |
| 2003/0105077 A1 | 6/2003 | Kanstrup et al. |
| 2003/0114390 A1 | 6/2003 | Washburn et al. |
| 2003/0130313 A1 | 7/2003 | Fujino et al. |
| 2003/0149071 A1 | 8/2003 | Gobbi et al. |
| 2003/0153509 A1 | 8/2003 | Bachovchin et al. |
| 2003/0166578 A1 | 9/2003 | Arch et al. |
| 2003/0199528 A1 | 10/2003 | Kanstrup et al. |
| 2003/0224043 A1 | 12/2003 | Appel et al. |
| 2003/0232987 A1 | 12/2003 | Dahanukar et al. |
| 2003/0236272 A1 | 12/2003 | Carr |
| 2004/0018468 A1 | 1/2004 | Gorokhovsky |
| 2004/0022866 A1 | 2/2004 | Rampoldi et al. |
| 2004/0023981 A1 | 2/2004 | Ren et al. |

(56) References Cited

U.S. PATENT DOCUMENTS

| | | |
|---|---|---|
| 2004/0034014 A1 | 2/2004 | Kanstrup et al. |
| 2004/0037883 A1 | 2/2004 | Zhou et al. |
| 2004/0063725 A1 | 4/2004 | Barth et al. |
| 2004/0077645 A1 | 4/2004 | Himmelsbach et al. |
| 2004/0082570 A1 | 4/2004 | Yoshikawa et al. |
| 2004/0087587 A1 | 5/2004 | Himmelsbach et al. |
| 2004/0097399 A1 | 5/2004 | Rapin et al. |
| 2004/0097410 A1 | 5/2004 | Zheng et al. |
| 2004/0097510 A1 | 5/2004 | Himmelsbach et al. |
| 2004/0116328 A1 | 6/2004 | Yoshikawa et al. |
| 2004/0122048 A1 | 6/2004 | Benjamin et al. |
| 2004/0122228 A1 | 6/2004 | Maier et al. |
| 2004/0126358 A1 | 7/2004 | Warne et al. |
| 2004/0138214 A1 | 7/2004 | Himmelsbach et al. |
| 2004/0138215 A1 | 7/2004 | Eckhardt et al. |
| 2004/0152659 A1 | 8/2004 | Matsuoka et al. |
| 2004/0152720 A1 | 8/2004 | Hartig et al. |
| 2004/0166125 A1 | 8/2004 | Himmelsbach et al. |
| 2004/0171836 A1 | 9/2004 | Fujino et al. |
| 2004/0180925 A1 | 9/2004 | Matsuno et al. |
| 2004/0259843 A1 | 12/2004 | Madar et al. |
| 2004/0259903 A1 | 12/2004 | Boehringer et al. |
| 2004/0266806 A1 | 12/2004 | Sanghvi et al. |
| 2005/0020484 A1 | 1/2005 | Harada |
| 2005/0020574 A1 | 1/2005 | Hauel et al. |
| 2005/0026921 A1 | 2/2005 | Eckhardt et al. |
| 2005/0027012 A1 | 2/2005 | Kohlrausch |
| 2005/0031682 A1 | 2/2005 | Cucala Escoi et al. |
| 2005/0032804 A1 | 2/2005 | Cypes et al. |
| 2005/0065145 A1 | 3/2005 | Cao et al. |
| 2005/0070562 A1 | 3/2005 | Jones et al. |
| 2005/0070594 A1 | 3/2005 | Kauschke et al. |
| 2005/0070694 A1 | 3/2005 | Gelfanova et al. |
| 2005/0097798 A1 | 5/2005 | Evans et al. |
| 2005/0107730 A1 | 5/2005 | Doty et al. |
| 2005/0119162 A1 | 6/2005 | Harada et al. |
| 2005/0130985 A1 | 6/2005 | Himmelsbach et al. |
| 2005/0143377 A1 | 6/2005 | Himmelsbach et al. |
| 2005/0171093 A1 | 8/2005 | Eckhardt et al. |
| 2005/0187227 A1 | 8/2005 | Himmelsbach et al. |
| 2005/0203095 A1 | 9/2005 | Eckhardt et al. |
| 2005/0234108 A1 | 10/2005 | Himmelsbach et al. |
| 2005/0234235 A1 | 10/2005 | Eckhardt et al. |
| 2005/0239778 A1 | 10/2005 | Konetzki et al. |
| 2005/0244502 A1 | 11/2005 | Mathias et al. |
| 2005/0256310 A1 | 11/2005 | Hulin et al. |
| 2005/0261271 A1 | 11/2005 | Feng et al. |
| 2005/0261352 A1 | 11/2005 | Eckhardt |
| 2005/0266080 A1 | 12/2005 | Desai et al. |
| 2005/0276794 A1 | 12/2005 | Papas et al. |
| 2006/0004074 A1 | 1/2006 | Eckhardt et al. |
| 2006/0008829 A1 | 1/2006 | Hess |
| 2006/0034922 A1 | 2/2006 | Cheng et al. |
| 2006/0039968 A1 | 2/2006 | Manikandan et al. |
| 2006/0039974 A1 | 2/2006 | Akiyama et al. |
| 2006/0047125 A1 | 3/2006 | Leonardi et al. |
| 2006/0058323 A1 | 3/2006 | Eckhardt et al. |
| 2006/0063787 A1 | 3/2006 | Yoshikawa et al. |
| 2006/0074058 A1 | 4/2006 | Holmes et al. |
| 2006/0079541 A1 | 4/2006 | Langkopf et al. |
| 2006/0094722 A1 | 5/2006 | Yasuda et al. |
| 2006/0100199 A1 | 5/2006 | Yoshikawa et al. |
| 2006/0106035 A1 | 5/2006 | Hendrix et al. |
| 2006/0111372 A1 | 5/2006 | Hendrix et al. |
| 2006/0111379 A1 | 5/2006 | Guillemont et al. |
| 2006/0134206 A1 | 6/2006 | Iyer et al. |
| 2006/0142310 A1 | 6/2006 | Pfrengle et al. |
| 2006/0154866 A1 | 7/2006 | Chu et al. |
| 2006/0159746 A1 | 7/2006 | Troup et al. |
| 2006/0173056 A1 | 8/2006 | Kitajima et al. |
| 2006/0205711 A1 | 9/2006 | Himmelsbach et al. |
| 2006/0205943 A1 | 9/2006 | Dahanukar et al. |
| 2006/0247226 A1 | 11/2006 | Himmelsbach et al. |
| 2006/0270668 A1 | 11/2006 | Chew et al. |
| 2006/0270701 A1 | 11/2006 | Kroth et al. |
| 2007/0014855 A1 | 1/2007 | Rahul et al. |
| 2007/0027168 A1 | 2/2007 | Pfrengle et al. |
| 2007/0059797 A1 | 3/2007 | Low et al. |
| 2007/0060530 A1 | 3/2007 | Christopher et al. |
| 2007/0072803 A1 | 3/2007 | Chu et al. |
| 2007/0072810 A1 | 3/2007 | Asakawa |
| 2007/0088038 A1 | 4/2007 | Eckhardt et al. |
| 2007/0093659 A1 | 4/2007 | Bonfanti et al. |
| 2007/0142383 A1 | 6/2007 | Eckhardt et al. |
| 2007/0173452 A1 | 7/2007 | DiMarchi et al. |
| 2007/0185091 A1 | 8/2007 | Himmelsbach et al. |
| 2007/0196472 A1 | 8/2007 | Kiel et al. |
| 2007/0197522 A1 | 8/2007 | Edwards et al. |
| 2007/0197552 A1 | 8/2007 | Carr |
| 2007/0219178 A1 | 9/2007 | Muramoto |
| 2007/0254944 A1 | 11/2007 | Hughes |
| 2007/0259880 A1 | 11/2007 | Sakashita et al. |
| 2007/0259900 A1 | 11/2007 | Sieger et al. |
| 2007/0259925 A1 | 11/2007 | Boehringer et al. |
| 2007/0259927 A1 | 11/2007 | Suzuki et al. |
| 2007/0265349 A1 | 11/2007 | Rapin et al. |
| 2007/0281940 A1 | 12/2007 | Dugi et al. |
| 2007/0299076 A1 | 12/2007 | Piotrowski et al. |
| 2008/0014270 A1 | 1/2008 | Harada |
| 2008/0039427 A1 | 2/2008 | Ray et al. |
| 2008/0107731 A1 | 5/2008 | Kohlrausch et al. |
| 2008/0108816 A1 | 5/2008 | Zutter |
| 2008/0221200 A1 | 9/2008 | Allison et al. |
| 2008/0234291 A1 | 9/2008 | Francois et al. |
| 2008/0249089 A1 | 10/2008 | Himmelsbach et al. |
| 2008/0255159 A1 | 10/2008 | Himmelsbach et al. |
| 2008/0312243 A1 | 12/2008 | Eckhardt et al. |
| 2008/0318922 A1 | 12/2008 | Nakahira et al. |
| 2009/0023920 A1 | 1/2009 | Eckhardt |
| 2009/0054303 A1 | 2/2009 | Gougoutas et al. |
| 2009/0082256 A1 | 3/2009 | Abe et al. |
| 2009/0088408 A1 | 4/2009 | Meade et al. |
| 2009/0088569 A1 | 4/2009 | Eckhardt et al. |
| 2009/0093457 A1 | 4/2009 | Himmelsbach et al. |
| 2009/0131432 A1 | 5/2009 | Himmelsbach et al. |
| 2009/0136596 A1 | 5/2009 | Munson et al. |
| 2009/0137801 A1 | 5/2009 | Himmelsbach et al. |
| 2009/0149483 A1 | 6/2009 | Nakahira et al. |
| 2009/0186086 A1 | 7/2009 | Shankar et al. |
| 2009/0192314 A1 | 7/2009 | Pfrengle et al. |
| 2009/0253752 A1 | 10/2009 | Burkey et al. |
| 2009/0297470 A1 | 12/2009 | Franz |
| 2009/0301105 A1 | 12/2009 | Loerting |
| 2009/0325926 A1 | 12/2009 | Himmelsbach |
| 2010/0074950 A1 | 3/2010 | Sesha |
| 2010/0092551 A1 | 4/2010 | Nakamura et al. |
| 2010/0173916 A1 | 7/2010 | Himmelsbach et al. |
| 2010/0179191 A1 | 7/2010 | Himmelsbach et al. |
| 2010/0183531 A1 | 7/2010 | Johncock et al. |
| 2010/0204250 A1 | 8/2010 | Himmelsbach et al. |
| 2010/0209506 A1 | 8/2010 | Eisenreich |
| 2010/0310664 A1 | 12/2010 | Watson et al. |
| 2010/0317575 A1 | 12/2010 | Pinnetti et al. |
| 2010/0330177 A1 | 12/2010 | Pourkavoos |
| 2011/0009391 A1 | 1/2011 | Braun et al. |
| 2011/0028391 A1 | 2/2011 | Holst et al. |
| 2011/0046076 A1 | 2/2011 | Eickelmann et al. |
| 2011/0065731 A1 | 3/2011 | Dugi et al. |
| 2011/0092510 A1 | 4/2011 | Klein et al. |
| 2011/0098240 A1 | 4/2011 | Dugi et al. |
| 2011/0112069 A1 | 5/2011 | Himmelsbach et al. |
| 2011/0144083 A1 | 6/2011 | Himmelsbach et al. |
| 2011/0144095 A1 | 6/2011 | Himmelsbach et al. |
| 2011/0190322 A1 | 8/2011 | Klein et al. |
| 2011/0195917 A1 | 8/2011 | Dugi et al. |
| 2011/0206766 A1 | 8/2011 | Friedl et al. |
| 2011/0212982 A1 | 9/2011 | Christopher et al. |
| 2011/0263493 A1 | 10/2011 | Dugi et al. |
| 2011/0263617 A1 | 10/2011 | Mark et al. |
| 2011/0275561 A1 | 11/2011 | Graefe-Mody et al. |
| 2011/0301182 A1 | 12/2011 | Dugi |
| 2012/0003313 A1 | 1/2012 | Kohlrausch et al. |
| 2012/0035158 A1 | 2/2012 | Himmelsbach et al. |
| 2012/0040982 A1 | 2/2012 | Himmelsbach et al. |

(56) References Cited

U.S. PATENT DOCUMENTS

| | | |
|---|---|---|
| 2012/0053173 A1 | 3/2012 | Banno et al. |
| 2012/0094894 A1 | 4/2012 | Graefe-Mody et al. |
| 2012/0107398 A1 | 5/2012 | Schneider et al. |
| 2012/0121530 A1 | 5/2012 | Klein et al. |
| 2012/0122776 A1 | 5/2012 | Graefe-Mody et al. |
| 2012/0129874 A1 | 5/2012 | Sieger et al. |
| 2012/0142712 A1 | 6/2012 | Pfrengle et al. |
| 2012/0165251 A1 | 6/2012 | Klein et al. |
| 2012/0208831 A1 | 8/2012 | Himmelsbach et al. |
| 2012/0219622 A1 | 8/2012 | Kohlrausch et al. |
| 2012/0219623 A1 | 8/2012 | Meinicke |
| 2012/0232004 A1 | 9/2012 | Bachovchin et al. |
| 2012/0252782 A1 | 10/2012 | Himmelsbach et al. |
| 2012/0252783 A1 | 10/2012 | Himmelsbach et al. |
| 2012/0296091 A1 | 11/2012 | Sieger et al. |
| 2013/0064887 A1 | 3/2013 | Ito et al. |
| 2013/0122089 A1 | 5/2013 | Kohlrausch et al. |
| 2013/0172244 A1 | 7/2013 | Klein et al. |
| 2013/0184204 A1 | 7/2013 | Pfrengle et al. |
| 2013/0196898 A1 | 8/2013 | Dugi et al. |
| 2013/0236543 A1 | 9/2013 | Ito et al. |
| 2013/0303462 A1 | 11/2013 | Klein |
| 2013/0303554 A1 | 11/2013 | Klein et al. |
| 2013/0310398 A1 | 11/2013 | Mark et al. |
| 2013/0315975 A1 | 11/2013 | Klein et al. |
| 2013/0317046 A1 | 11/2013 | Johansen |
| 2013/0324463 A1 | 12/2013 | Klein et al. |
| 2014/0100236 A1 | 4/2014 | Busl et al. |
| 2014/0274889 A1 | 9/2014 | Johansen et al. |
| 2014/0315832 A1 | 10/2014 | Broedl et al. |
| 2014/0343014 A1 | 11/2014 | Klein et al. |
| 2014/0371243 A1 | 12/2014 | Klein et al. |
| 2015/0196565 A1 | 7/2015 | Klein et al. |
| 2015/0246045 A1 | 9/2015 | Klein et al. |
| 2015/0265538 A1 | 9/2015 | Balthes et al. |
| 2016/0058769 A1 | 3/2016 | Graefe-Mody et al. |
| 2016/0082011 A1 | 3/2016 | Klein et al. |
| 2016/0089373 A1 | 3/2016 | Johansen et al. |
| 2016/0106677 A1 | 4/2016 | Boeck et al. |
| 2016/0310435 A1 | 10/2016 | Friedl et al. |
| 2017/0020868 A1 | 1/2017 | Dugi et al. |
| 2017/0354660 A1 | 12/2017 | Meinicke et al. |
| 2021/0205316 A1 | 7/2021 | Johansen et al. |
| 2021/0299120 A1 | 9/2021 | Gupta |
| 2022/0378797 A1 | 12/2022 | Friedl et al. |

FOREIGN PATENT DOCUMENTS

| | | |
|---|---|---|
| CA | 1123437 A1 | 5/1982 |
| CA | 2136288 A1 | 5/1995 |
| CA | 2375779 | 5/2000 |
| CA | 2418656 A1 | 2/2002 |
| CA | 2435730 A1 | 9/2002 |
| CA | 2496249 A1 | 3/2004 |
| CA | 2496325 A1 | 3/2004 |
| CA | 2498423 A1 | 4/2004 |
| CA | 2505389 A1 | 5/2004 |
| CA | 2508233 A1 | 6/2004 |
| CA | 2529729 A1 | 12/2004 |
| CA | 2543074 A1 | 6/2005 |
| CA | 2555050 A1 | 9/2005 |
| CA | 2556064 A1 | 9/2005 |
| CA | 2558067 A1 | 10/2005 |
| CA | 2558446 A1 | 10/2005 |
| CA | 2561210 A1 | 10/2005 |
| CA | 2562859 A1 | 11/2005 |
| CA | 2576294 A1 | 3/2006 |
| CA | 2590912 A1 | 6/2006 |
| CA | 2599419 A1 | 11/2006 |
| CA | 2651019 A1 | 11/2007 |
| CA | 2651089 A1 | 11/2007 |
| CA | 2720450 A1 | 10/2009 |
| CN | 101035522 A | 9/2007 |
| CN | 101234105 A | 8/2008 |
| CN | 101309689 A | 11/2008 |
| CN | 101590007 A | 12/2009 |
| CN | 104130258 A | 11/2014 |
| CN | 104418857 A | 3/2015 |
| CN | 105272982 A | 1/2016 |
| DE | 2205815 A1 | 8/1973 |
| DE | 2758025 A1 | 7/1979 |
| DE | 19705233 A1 | 8/1998 |
| DE | 10109021 A1 | 9/2002 |
| DE | 10117803 A1 | 10/2002 |
| DE | 10238243 A1 | 3/2004 |
| DE | 102004019540 A1 | 11/2005 |
| DE | 102004024454 A1 | 12/2005 |
| DE | 102004044221 A1 | 3/2006 |
| DE | 102004054054 A1 | 5/2006 |
| EA | 201300121 | 10/2009 |
| EP | 0023032 A1 | 1/1981 |
| EP | 0149578 A2 | 7/1985 |
| EP | 0189941 A2 | 8/1986 |
| EP | 0223403 A2 | 5/1987 |
| EP | 0237608 A1 | 9/1987 |
| EP | 0248634 A2 | 12/1987 |
| EP | 0289282 A2 | 11/1988 |
| EP | 0342675 A2 | 11/1989 |
| EP | 0389282 A2 | 9/1990 |
| EP | 0399285 A1 | 11/1990 |
| EP | 0400974 A2 | 12/1990 |
| EP | 409281 A1 | 1/1991 |
| EP | 0412358 A1 | 2/1991 |
| EP | 443983 A1 | 8/1991 |
| EP | 0475482 A1 | 3/1992 |
| EP | 0524482 A1 | 1/1993 |
| EP | 0638567 A1 | 2/1995 |
| EP | 0657454 A1 | 6/1995 |
| EP | 0775704 A1 | 5/1997 |
| EP | 0950658 A1 | 10/1999 |
| EP | 1054012 A1 | 11/2000 |
| EP | 1066265 A1 | 1/2001 |
| EP | 1310245 A1 | 5/2003 |
| EP | 1333033 | 8/2003 |
| EP | 1338595 A2 | 8/2003 |
| EP | 1406873 A2 | 4/2004 |
| EP | 1500403 A1 | 1/2005 |
| EP | 1514552 A1 | 3/2005 |
| EP | 1523994 A1 | 4/2005 |
| EP | 1535906 A1 | 6/2005 |
| EP | 1537880 A1 | 6/2005 |
| EP | 1557165 A1 | 7/2005 |
| EP | 1586571 A1 | 10/2005 |
| EP | 1604989 A1 | 12/2005 |
| EP | 1743655 A1 | 1/2007 |
| EP | 1760076 | 3/2007 |
| EP | 1829877 A1 | 9/2007 |
| EP | 1852108 A1 | 11/2007 |
| EP | 1897892 A2 | 3/2008 |
| EP | 2143443 A1 | 1/2010 |
| EP | 2166007 A1 | 3/2010 |
| EP | 2308878 A2 | 4/2011 |
| EP | 3646859 A1 | 5/2020 |
| ES | 385302 A1 | 4/1973 |
| ES | 2256797 T3 | 7/2006 |
| ES | 2263057 T3 | 12/2006 |
| FR | 2707641 A1 | 1/1995 |
| GB | 2084580 A | 4/1982 |
| HU | 9003243 | 5/1990 |
| HU | 9902308 A2 | 7/2000 |
| JP | S374895 A | 6/1962 |
| JP | 61030567 | 2/1986 |
| JP | 770120 | 3/1995 |
| JP | 8333339 | 12/1996 |
| JP | 11193270 | 7/1999 |
| JP | 2000502684 A | 3/2000 |
| JP | 2001213770 A | 8/2001 |
| JP | 2001278812 A | 10/2001 |
| JP | 2001292388 A | 10/2001 |
| JP | 2002348279 A | 12/2002 |
| JP | 2003286287 A | 10/2003 |
| JP | 2003300977 A | 10/2003 |
| JP | 2004161749 A | 6/2004 |
| JP | 2004196824 A | 7/2004 |

(56) References Cited

FOREIGN PATENT DOCUMENTS

| | | |
|---|---|---|
| JP | 2004250336 A | 9/2004 |
| JP | 2005511636 A | 4/2005 |
| JP | 2005519059 A | 6/2005 |
| JP | 2006503013 A | 1/2006 |
| JP | 2006045156 A | 2/2006 |
| JP | 2006137678 A | 6/2006 |
| JP | 2007501231 A | 1/2007 |
| JP | 2007510059 A | 4/2007 |
| JP | 2007522251 A | 8/2007 |
| JP | 2007531780 A | 11/2007 |
| JP | 2008513390 A | 5/2008 |
| JP | 2008536881 A | 9/2008 |
| JP | 2010500326 A | 1/2010 |
| JP | 2010053576 A | 3/2010 |
| JP | 2010070576 A | 4/2010 |
| JP | 2010524580 A | 7/2010 |
| JP | 2010535850 A | 11/2010 |
| JP | 2010536734 A | 12/2010 |
| JP | 2011088838 A | 5/2011 |
| JP | 2011529945 A | 12/2011 |
| JP | 2012502081 A | 1/2012 |
| JP | 2012505859 A | 3/2012 |
| KR | 20070111099 A | 11/2007 |
| WO | 8706941 A1 | 11/1987 |
| WO | 199107945 A1 | 6/1991 |
| WO | 199205175 A1 | 4/1992 |
| WO | 199219227 A2 | 11/1992 |
| WO | 199308259 A2 | 4/1993 |
| WO | 199402150 A1 | 2/1994 |
| WO | 199403456 A1 | 2/1994 |
| WO | 1994012200 | 6/1994 |
| WO | 9532178 A1 | 11/1995 |
| WO | 199609045 A1 | 3/1996 |
| WO | 199611917 A1 | 4/1996 |
| WO | 199636638 A1 | 11/1996 |
| WO | 199718814 A1 | 5/1997 |
| WO | 199723447 A1 | 7/1997 |
| WO | 199723473 A1 | 7/1997 |
| WO | 199728808 A1 | 8/1997 |
| WO | 199746526 A1 | 12/1997 |
| WO | 1998007725 | 2/1998 |
| WO | 199811893 | 3/1998 |
| WO | 9818770 A1 | 5/1998 |
| WO | 199822464 A1 | 5/1998 |
| WO | 199828007 A1 | 7/1998 |
| WO | 199840069 A2 | 9/1998 |
| WO | 1998046082 A1 | 10/1998 |
| WO | 199856406 A1 | 12/1998 |
| WO | 9903854 A1 | 1/1999 |
| WO | 199929695 A1 | 6/1999 |
| WO | 1999038501 A2 | 8/1999 |
| WO | 199950248 A1 | 10/1999 |
| WO | 1999049857 | 10/1999 |
| WO | 199956561 A1 | 11/1999 |
| WO | 199967279 A1 | 12/1999 |
| WO | 2000003735 A1 | 1/2000 |
| WO | 200012064 A1 | 3/2000 |
| WO | 200072873 | 5/2000 |
| WO | 200034241 A1 | 6/2000 |
| WO | 0069464 A1 | 11/2000 |
| WO | 200066101 A2 | 11/2000 |
| WO | 0072799 A2 | 12/2000 |
| WO | 0078735 A1 | 12/2000 |
| WO | 200072973 A1 | 12/2000 |
| WO | 200073307 A2 | 12/2000 |
| WO | 200107441 A1 | 2/2001 |
| WO | 2001032158 A2 | 5/2001 |
| WO | 2001040180 A2 | 6/2001 |
| WO | 200152825 | 7/2001 |
| WO | 200152852 A1 | 7/2001 |
| WO | 2001047514 A1 | 7/2001 |
| WO | 2001051919 | 7/2001 |
| WO | 2001052825 A2 | 7/2001 |
| WO | 2001066548 A1 | 9/2001 |
| WO | 2001068603 | 9/2001 |
| WO | 2001068646 A1 | 9/2001 |
| WO | 200177110 A1 | 10/2001 |
| WO | 2001072290 A2 | 10/2001 |
| WO | 200196301 A1 | 12/2001 |
| WO | 200197808 A1 | 12/2001 |
| WO | 200202560 A2 | 1/2002 |
| WO | 200214271 A1 | 2/2002 |
| WO | 200224698 A1 | 3/2002 |
| WO | 2002053516 A2 | 7/2002 |
| WO | 2002068420 A1 | 9/2002 |
| WO | 2003000241 A2 | 1/2003 |
| WO | 2003000250 | 1/2003 |
| WO | 2003002531 A2 | 1/2003 |
| WO | 2003002553 A2 | 1/2003 |
| WO | 2003004496 A1 | 1/2003 |
| WO | 2003006425 | 1/2003 |
| WO | 2003024965 A2 | 3/2003 |
| WO | 2003033686 A2 | 4/2003 |
| WO | 03038123 A2 | 5/2003 |
| WO | 2003034944 A1 | 5/2003 |
| WO | 2003035177 A2 | 5/2003 |
| WO | 2003037327 A1 | 5/2003 |
| WO | 2003053929 A1 | 7/2003 |
| WO | 2003055881 A1 | 7/2003 |
| WO | 2003057200 A2 | 7/2003 |
| WO | 2003057245 A1 | 7/2003 |
| WO | 2003059327 | 7/2003 |
| WO | 2003061688 A1 | 7/2003 |
| WO | 2003064454 A1 | 8/2003 |
| WO | 2003074500 A2 | 9/2003 |
| WO | 2003088900 A2 | 10/2003 |
| WO | 2003094909 A2 | 11/2003 |
| WO | 2003099279 A1 | 12/2003 |
| WO | 2003099836 A1 | 12/2003 |
| WO | 2003104229 A1 | 12/2003 |
| WO | 2003106428 A1 | 12/2003 |
| WO | 2004002924 A1 | 1/2004 |
| WO | 2004011416 A1 | 2/2004 |
| WO | 2004016587 A1 | 2/2004 |
| WO | 2000003735 | 3/2004 |
| WO | 2004018467 A2 | 3/2004 |
| WO | 2004018468 A2 | 3/2004 |
| WO | 2004018469 A1 | 3/2004 |
| WO | 2004028524 A1 | 4/2004 |
| WO | 2004033455 A1 | 4/2004 |
| WO | 2004035575 A1 | 4/2004 |
| WO | 2004037169 A2 | 5/2004 |
| WO | 2004041820 A1 | 5/2004 |
| WO | 2004043940 | 5/2004 |
| WO | 2004046148 A1 | 6/2004 |
| WO | 2004048379 A1 | 6/2004 |
| WO | 2004050658 A1 | 6/2004 |
| WO | 2004052362 A1 | 6/2004 |
| WO | 2004058233 A1 | 7/2004 |
| WO | 2004062689 A1 | 7/2004 |
| WO | 2004065380 A1 | 8/2004 |
| WO | 2004074246 A2 | 9/2004 |
| WO | 2004081006 A1 | 9/2004 |
| WO | 2004082402 A1 | 9/2004 |
| WO | 2004096806 A1 | 11/2004 |
| WO | 2004096811 A1 | 11/2004 |
| WO | 2004104216 A2 | 12/2004 |
| WO | 2004106279 A2 | 12/2004 |
| WO | 2004108730 A1 | 12/2004 |
| WO | 2004111051 A1 | 12/2004 |
| WO | 2005000846 A1 | 1/2005 |
| WO | 2005000848 A1 | 1/2005 |
| WO | 2005007137 A2 | 1/2005 |
| WO | 2005007647 A1 | 1/2005 |
| WO | 2005007658 A2 | 1/2005 |
| WO | 2005012288 A1 | 2/2005 |
| WO | 2005016365 | 2/2005 |
| WO | 2005023179 A2 | 3/2005 |
| WO | 2005049022 A2 | 6/2005 |
| WO | 2005051950 A1 | 6/2005 |
| WO | 2005058901 A1 | 6/2005 |
| WO | 2005061489 A1 | 7/2005 |
| WO | 2005063750 A1 | 7/2005 |
| WO | 2005075410 A1 | 8/2005 |

(56) References Cited

FOREIGN PATENT DOCUMENTS

| | | |
|---|---|---|
| WO | 2005082906 A1 | 9/2005 |
| WO | 2005085246 A1 | 9/2005 |
| WO | 2005092870 A1 | 10/2005 |
| WO | 2005092877 A1 | 10/2005 |
| WO | 2005095343 A1 | 10/2005 |
| WO | 2005095381 A1 | 10/2005 |
| WO | 2005097798 A1 | 10/2005 |
| WO | 2005107730 A2 | 11/2005 |
| WO | 2005116000 A1 | 12/2005 |
| WO | 2005116014 A1 | 12/2005 |
| WO | 2005117861 A1 | 12/2005 |
| WO | 2005117948 A1 | 12/2005 |
| WO | 2005119526 A1 | 12/2005 |
| WO | 2006005613 A1 | 1/2006 |
| WO | 2006027204 A1 | 3/2006 |
| WO | 2006029577 A1 | 3/2006 |
| WO | 2006029769 A1 | 3/2006 |
| WO | 2006036664 A1 | 4/2006 |
| WO | 2006040625 A1 | 4/2006 |
| WO | 2006041976 A1 | 4/2006 |
| WO | 2006047248 A1 | 5/2006 |
| WO | 2006048209 A1 | 5/2006 |
| WO | 2006048427 A1 | 5/2006 |
| WO | 2006068163 A1 | 6/2006 |
| WO | 2006071078 A1 | 7/2006 |
| WO | 2006076231 A2 | 7/2006 |
| WO | 2006078593 A2 | 7/2006 |
| WO | 2006083491 A2 | 8/2006 |
| WO | 2006116157 | 11/2006 |
| WO | 2006129785 A1 | 12/2006 |
| WO | 2006135693 A2 | 12/2006 |
| WO | 2006137085 A1 | 12/2006 |
| WO | 2007007173 A2 | 1/2007 |
| WO | 2007014886 A1 | 2/2007 |
| WO | 2007014895 A2 | 2/2007 |
| WO | 2007017423 A1 | 2/2007 |
| WO | 07035665 A1 | 3/2007 |
| WO | 2007033350 A1 | 3/2007 |
| WO | 2007035355 A2 | 3/2007 |
| WO | 2007035665 A1 | 3/2007 |
| WO | 2007038979 A1 | 4/2007 |
| WO | 2007041053 A2 | 4/2007 |
| WO | 2007050485 A2 | 5/2007 |
| WO | 2007071738 | 6/2007 |
| WO | 2007072083 A1 | 6/2007 |
| WO | 2007078726 A2 | 7/2007 |
| WO | 2007093610 A1 | 8/2007 |
| WO | 2007099345 A1 | 9/2007 |
| WO | 2007120702 A2 | 10/2007 |
| WO | 2007120936 A2 | 10/2007 |
| WO | 2007128721 A | 11/2007 |
| WO | 2007128724 A1 | 11/2007 |
| WO | 2007128761 A2 | 11/2007 |
| WO | 2007135196 A2 | 11/2007 |
| WO | 2007136151 A1 | 11/2007 |
| WO | 2007137107 A2 | 11/2007 |
| WO | 2007147185 A1 | 12/2007 |
| WO | 2007148185 A2 | 12/2007 |
| WO | 2007149797 A2 | 12/2007 |
| WO | 2003057245 | 1/2008 |
| WO | 2008005569 A2 | 1/2008 |
| WO | 2008005576 A1 | 1/2008 |
| WO | 2008017670 | 2/2008 |
| WO | 2008017670 A1 | 2/2008 |
| WO | 2008022267 A2 | 2/2008 |
| WO | 2008042408 A2 | 4/2008 |
| WO | 2008055870 A1 | 5/2008 |
| WO | 2008055940 A2 | 5/2008 |
| WO | 2008070692 A2 | 6/2008 |
| WO | 2008077639 A1 | 7/2008 |
| WO | 2008081205 A1 | 7/2008 |
| WO | 2008083238 A2 | 7/2008 |
| WO | 2008087198 A1 | 7/2008 |
| WO | 2008093878 A1 | 8/2008 |
| WO | 2008093882 A1 | 8/2008 |
| WO | 2008097180 A1 | 8/2008 |
| WO | 2008113000 A1 | 9/2008 |
| WO | 2008130998 A2 | 10/2008 |
| WO | 2008131149 A2 | 10/2008 |
| WO | 2008137435 A1 | 11/2008 |
| WO | 2008114800 A3 | 12/2008 |
| WO | 2009011451 A | 1/2009 |
| WO | 2009022007 | 2/2009 |
| WO | 2009022007 A1 | 2/2009 |
| WO | 2009022008 A1 | 2/2009 |
| WO | 2009022009 A1 | 2/2009 |
| WO | 2009022010 A1 | 2/2009 |
| WO | 2009024542 A2 | 2/2009 |
| WO | 2009063072 A2 | 5/2009 |
| WO | 2009091082 A1 | 7/2009 |
| WO | 2009099734 A1 | 8/2009 |
| WO | 2009111200 A1 | 9/2009 |
| WO | 2009112691 A2 | 9/2009 |
| WO | 2009121945 A2 | 10/2009 |
| WO | 2009123992 A1 | 10/2009 |
| WO | 199967278 | 12/2009 |
| WO | 2009147125 A1 | 12/2009 |
| WO | 201092124 | 2/2010 |
| WO | 2010015664 A1 | 2/2010 |
| WO | 2010018217 A2 | 2/2010 |
| WO | 2010029089 A2 | 3/2010 |
| WO | 2010043688 A1 | 4/2010 |
| WO | 2010045656 A2 | 4/2010 |
| WO | 2010072776 A1 | 7/2010 |
| WO | 2010079197 A1 | 7/2010 |
| WO | 2010086411 A1 | 8/2010 |
| WO | 2010092125 A1 | 8/2010 |
| WO | 2010092163 A2 | 8/2010 |
| WO | 2010096384 A2 | 8/2010 |
| WO | 2010106457 A2 | 9/2010 |
| WO | 2010126908 A1 | 11/2010 |
| WO | 2010140111 A1 | 12/2010 |
| WO | 2010147768 A1 | 12/2010 |
| WO | 2011011541 A1 | 1/2011 |
| WO | 2011039337 A1 | 4/2011 |
| WO | 2011039367 A2 | 4/2011 |
| WO | 2011064352 A1 | 6/2011 |
| WO | 2011109333 | 9/2011 |
| WO | 2011113947 A1 | 9/2011 |
| WO | 2011138380 A1 | 11/2011 |
| WO | 2011138421 A1 | 11/2011 |
| WO | 2011154496 A1 | 12/2011 |
| WO | 2011161161 A1 | 12/2011 |
| WO | 2011163206 A2 | 12/2011 |
| WO | 2012031124 A2 | 3/2012 |
| WO | 2012039420 A1 | 3/2012 |
| WO | 2012065993 A1 | 5/2012 |
| WO | 2012088682 A1 | 7/2012 |
| WO | 2012089127 A1 | 7/2012 |
| WO | 2012106303 A1 | 8/2012 |
| WO | 2012120040 A1 | 9/2012 |
| WO | 2003061688 | 4/2013 |
| WO | 2013098372 A1 | 7/2013 |
| WO | 2013103629 A1 | 7/2013 |
| WO | 2013131967 A1 | 9/2013 |
| WO | 2013171167 A1 | 11/2013 |
| WO | 2013174768 A1 | 11/2013 |
| WO | 2013179307 A2 | 12/2013 |
| WO | 2014029848 A1 | 2/2014 |
| WO | 2014140284 A1 | 9/2014 |
| WO | 2014170383 A1 | 10/2014 |
| WO | 20160089373 | 1/2017 |
| WO | 2017047970 A1 | 3/2017 |
| WO | 2020016232 | 1/2020 |
| WO | 2020016232 A1 | 1/2020 |

OTHER PUBLICATIONS

Halimi, "Combination treatment in the management of type 2 diabetes: focus on vildagliptin and metformin as a single tablet", Vascular Health and Risk Management, 2008 481-92.
Halimi, S. et al., "Combination treatment in the management of type 2 diabetes: focus on vildagliptin and metformin as a single tablet."

(56) References Cited

OTHER PUBLICATIONS

Vascular Health and Risk Management, 2008, vol. 4, No. 3, pp. 481-492.
Haluzik, M. et al., "Renal Effects of DPP-4 Inhibitors: A Focus on Microalbuminuria." International Journal of Endocrinology, 2013, vol. 35, No. 6, pp. 1-7.
Hammouda, Y. et al., "Lactose-induced Discoloration of Amino Drugs in Solid Dosage Form." Die Pharmazie, 1971, vol. 26, p. 181.
Han, Basic and Clinical Coronary Heart Disease, Jilin Univ. Press, 2012, p. 114-118.
Hansen, European Journal of Pharmacology, "The DPP-IV inhibitor linagliptin and GLP-1 induce synergistic effects on body weight loss and appetite suppression in the diet-induced obese rat", 2014, p. 254-263.
Hansen, H. et al., "Co-Administration of the DPP-4 Inhibitor Linagliptin and Native GLP-1 Induce Body Weight Loss and Appetite Suppression." 73rd Annual Meeting Science Session, ADA, Chicago, Jun. 21, 2013.
Hashida, Mitsuru, "Strategies for designing and developing oral administration formulations." Yakuji-Jiho, Inc., 1995, pp. 50-51 and 89.
Hayashi, Michio., "Recipe for Oral Hypoglycemic Agents to Pathological Condition" Pharmacy (2006) vol. 57, No. 9 pp. 2735-2739.
He, Y. L. et al., "Bioequivalence of Vildagliptin/Metformin Combination Tablets and Coadministration of Vildagliptin and Metformin as Free Combination in Healthy Subjects". J. Clinical Pharmacology, 2007, vol. 47, No. 9, Abstracts of the 36th Annual Meeting of the American College of Clinical Pharmacology, San Francisco, CA, Abstract 116, p. 1210.
He, Y.L. et al., "The influence of hepatic impairment on the pharmacokinetics f the dipeptidyl peptidase IV (DPP-4) inhibitor vildagliptin" European Journal of Clinical Pharmacology, vol. 63, No. 7, May 8, 2007, p. 677-686.
He, Y.L. et al., "The Influence of Renal Impairment on the Pharmacokinetics of Vildagliptin." Clinical Pharmacology & Therapeutics, 2007, vol. 81, Suppl. 1, Abstract No. PIII-86.
Headland, K. et al., "The Effect of Combination Linagliptin and Voglibose on Glucose Control and Body Weight." 73rd Annual Meeting Science Session, ADA, Chicago, Jun. 21, 2013.
Heihachiro, A. et al., "Synthesis of Prolyl Endopeptidase Inhibitors and Evaluation of Their Structure-Activity Relationships: In Vitro Inhibition of Prolyl Endopeptidase from Canine Brain." 1993, Chemical and Pharmaceutical Bulletin, vol. 41, pp. 1583-1588.
Heise, et al., Diabetes, Obesity and Metabolism, "Pharmacokinetics, pharmacokinetics and tolerability of mutilple oral doses of linagliptin, a dipeptidyl peptidase-4 inhibitor in male type 2 diabetes patients", 2009, vol. 11, No. 8, p. 786-794.
Heise, T. et al., "Treatment with BI 1356, a Novel and Potent DPP-IV Inhibitor, Significantly Reduces Glucose Excursions after an OGTT in Patients with Type 2 Diabetes." A Journal of the American Diabetes Association, Jun. 2007, vol. 56, Supplement 1, Poster No. 0588P.
Herman, G. A. et al., "Dipeptidyl Peptidase-4 Inhibitors for the Treatment of Type 2 Diabetes: Focus on Sitagliptin." Clinical Pharmacology and Therapeutics, 2007, vol. 81, No. 5, pp. 761-767.
Herman, Gary et al. "Co-Administration of MK-0431 and Metformin in Patients with Type 2 Diabetes Does Not Alter the Pharmacokinetics of MK-0431 or Metformin" (2005) Journal of American Diabetes Association vol. 54, Supplement 1, 3 pgs.
Hermann, Robert, et al; Lack of Association of PAX4 Gene with Type 1 Diabetes in the Hungarian Populations; Diabetes (2005) vol. 54 pp. 2816-2819.
Hermansen, K., "Efficacy and Safety of the Dipeptidyl Peptidase-4 Inhibitor, Sitagliptin, in Patients with Type 2 Diabetes Mellitus Inadequately Controlled on Glimepiride Alone or on Glimepiride and Metformin". Diabetes, Obesity and Metabolism (2007) vol. 9, No. 5 pp. 733-745.
Hilfiker, R. et al., "Relevance of Solid-state Properties for Pharmaceutical Products." Polymorphism in the Pharmaceutical Industry, 2006, Chapter 1, pp. 1-19.
Hinke, S.A. et al., "Metformin Effects on Dipeptidylpeptidase IV Degradation of Glucagon-like Peptide-1." Biochemical and Biophysical Research Communications, 2002, vol. 291, No. 5, pp. 1302-1308.
Hinke, S.A. et al., "On Combination Therapy of Diabetes With Metformin and Dipeptidyl Peptidase IV Inhibitors." Diabetes Care, 2002, vol. 25, No. 8, pp. 1490-1492.
Hinnen, D. et al., "Incretin Mimetics and DPP-IV Inhibitors: New Paradigms for the Treatment of Type 2 Diabetes." Journal Of The American Board Of Family Medicine, 2006, vol. 19, No. 6, pp. 612-620.
Hocher, B. et al., "Renal and Cardiac Effects of DPP-4 Inhibitors—from Preclinical Development to Clinical Research." Kidney & Blood Pressue Research, 2012, vol. 36, No. 1, pp. 65-84.
Hocher, B. et al., "The novel DPP-4 inhibitors linagliptin and BI 14361 reduce infarct size after myocardial ischemia/reperfusion in rats." International Journal of Cardiology, 2013, vol. 167, pp. 87-93.
Holman, et al., "Addition of biphasic, prandial, or basal insulin to oral therapy in type 2 diabetes", N. England Journal Medicine, p. 1716-1730, 2007.
Holst,Role on incretin hormones in the regulation of insulin, Am j. Physiol Endocrinol Metab., 2004.
Horikawa, Synergistic Efffect of a-glucosidase inhibitors and dipeptidyl peptidase 4 inhibitor treatment, Journal of Diabetes Investigation, 2011, vol. 2, p. 200-203.
Horsford, E. N. "On the source of free hydrochloric acid in the gastric juice." Proceedings of the Royal Society of London, Published in 1868-1869, vol. 17, pp. 391-395.
Houben-Weyl, Oxygen Compounds, Methods of Organic Chemistry, 1929, 5 pages.
Hu, Diabetes Mellitus and Cardiovascular Disease, People's Military Medical Press, 2005, p. 211.
Hu, Y. et al., "Synthesis and Structure-activity Relationship of N-alkyl Gly-boro-Pro Inhibitors of DPP4, FAP, and DPP7." Bioorganic & Medicinal Chemistry Letters 15, 2005, pp. 4239-4242.
Huang, et al. Elimination of metformin-croscarmellose sodium interaction by competition, International Journal of Pharmaceutics, 2006, p. 33-39.
Huettner Silks et al: "BI 1356, a novel and selective xanthine based DPP-IV inhibitor, demonstrates good safety and tolerability with a wide therapeutic window" Diabetes< American Diabetes Association, US, vol. 56, No. Suppl 1, Jun. 1, 2007, p. A156.
Hull, R. et al., "Nephrotic syndrome in adults." British Medical Journal, 2008, vol. 336, pp. 1185-1190.
Hunziker, D. et al., "Inhibitors of DPP IV-recent advances and structural views", Current Topics in Medicinal Chemistry, 2005, vol. 5 issue 16, pp. 1623-1637.
Huttner, S. et al., "Safety, Tolerability, Pharmacokinetics, and Pharmacodynamics of Single Oral Doses of BI 1356, an Inhibitor of Dipeptidyl Peptidase 4, in Healthy Male Volunteers." Journal of Clinical Pharmacology, 2008, vol. 48, No. 10, pp. 1171-1178.
Inagaki, Linagliptin provides effective, well-tolerated add-on therapy to pre-existing oral antidiabetic therapy over 1 year in Japanese patients with type 2 diabetes, Diabetes, Obesity and Metabolis, 2013, p. 833-843.
International Search Report—European Search Report for PCT/EP2003/09127 mailed Mar. 1, 2011.
International Search Report and Written Opinion for PCT/EP2006/064657 mailed Nov. 2, 2006.
International Search Report and Written Opinion for PCT/EP2007/054201 mailed Aug. 29, 2007.
International Search Report and Written Opinion for PCT/EP2007/054270 mailed Aug. 14, 2007.
International Search Report and Written Opinion for PCT/EP2008/060740 mailed Mar. 30, 2009.
International Search Report and Written Opinion for PCT/EP2009/053978 mailed Sep. 29, 2009.
International Search Report and Written Opinion for PCT/EP2009/056722 mailed Aug. 13, 2009.
International Search Report and Written Opinion for PCT/EP2009/060521 mailed Mar. 9, 2010.
International Search Report and Written Opinion for PCT/EP2009/063511 mailed Feb. 26, 2010.

(56) References Cited

OTHER PUBLICATIONS

Clinical Trials: NCT00954447, View on Jun. 14, 2010. "Efficacy and Safety of Linagliptin in Combination with Insulin in Patients with Type 2 Diabetes". <http://clinicaltrials.gov/archive/NCT00954447/2010_06_14>.

Clinical Trials: NCT00103857, "A Multicenter, Randomized, Double-Blind Factorial Study of the Co-Administration of MK0431 and Metformin in Patients With Type 2 Diabetes Mellitus Who Have Inadequate Glycemic Control" last updated on Apr. 27, 2015.

Clinical Trials: NCT00309608, "Efficacy and Safety of BI 1356 BS (Linagliptin) in Combination With Metformin in Patients With type2 Diabetes" Boehringer Ingelheim Pharmaceuticals, last updated on Jun. 24, 2014.

Clinical Trials: NCT00309608, "Efficacy and Safety of BI 1356 BS (Linagliptin) in Combination With Metformin in Patients With type2 Diabetes" Boehringer Ingelheim Pharmaceuticals, last updated: Dec. 11, 2013.

Clinical Trials: NCT00309608. Efficacy and safety of BI 1356 in combination with metformin in patients with type2 diabetes. Boehringer Ingelheim Pharmaceuticals, Jan. 27, 2009. Clinical Trials.gov . http://clinicaltrials.gov/archive/NCT00309608/2009_01_27.

Clinical Trials: NCT00602472. "BI 1356 in combination withe metformin and a sulphonylurea in Type 2 Diabetes". DrugLib.com, Nov. 3, 2008. http://www.druglib.com/trial/08/NCT00309608.html.

Clinical Trials: NCT00622284. Efficacy and Safety of BI 1356 in Combination with Metformin in Patients with Type 2 Diabetes. Boehringer Ingelheim Pharmaceuticals, Aug. 2008. http://clinicaltrials.gov/archive/NCT00622284/2010_01_13.

Clinical Trials: NCT00798161. "Safety and efficacy of Bi 1356 Plus Metformin in Type 2 Diabetes, Factorial Design". Clinical Trials. gov archive. A Service of the U.S> National Institutes of Health. Nov. 24, 2008, p. 1-3. http://clinicaltrials.gov/archive/NCT00798161/2008_11_24.

Colorcon (retrieved from website http://www.colorcon.com/products-formulation/all-products/film-coatings/immediate-release/opadry, published2015).

Colorcon, "Lactose Replacement with Starch 1500 in a Direct Compression Formula." 2005, pp. 1-4.

Colorcon, "Reducing Coated Tablet Defects from Laboratory through Production Scale: Performance of Hypromellose or Polyvinyl Alcohol-Based Aqueous Film Coating Systems." Opadry II, 2009, pp. 1-7.

Combs, D. W. et al., "Phosphoryl Chloride Induced Ring Contraction of 11,4-Benzodiazepinones to Chloromethylquinazolines". J. Heterocyclic Chemistry, BD. 23, 1986, p. 1263-1264.

Conarello, S.L. et al., "Mice lacking dipeptidyl peptidase IV are protected against obesity and insulin resistance". PNAS, May 27, 2003, vol. 100, No. 11, p. 6825-6830.

Connelly, Dipeptyl peptidase-4 inhibition improves left ventricular function in chronic kidney disease, Clinical and Investigative Medicine, vol. 37, 2014, p. 172-185.

Controlling Temperature (Guidelines for the Storage of Essential Medicines and Other Health Commodities, 2003, http://apps.who.int.medicinedocs/en/d/Js4885e/6.5html), 5 pages.

Cotton, M.L. et al., "L-649,923—The selection of an appropriate salt form and preparation of a stable oral formulation." International Journal of Pharmaceutics, 1994, vol. 109, Issue 3, pp. 237-249.

Craddy, P. et al., "Comparative Effectiveness of Dipeptidylpeptidase-4 Inhibitors in Type 2 Diabetes: A Systematic Review and Mixed Treatment Comparison." Diabetes Therapy, 2014, vol. 5, No. 1, pp. 1-41.

Crowe, E. et al., "Early identification and management of chronic kidney disease: summary of NICE guidance." British Medical Journal, 2008, vol. 337, pp. 812-815.

Cygankiewicz, Andrzej et al., Investigations into the Piperazine Derivatives of Dimethylxanthine:, Acta Polon. Pharm. [Papers of Polish Pharmacology], XXXOV, No. 5, pp. 607-612, 1977.

Dave, K.G. et al., "Reaction of Nitriles under Acidic Conditions, Part I. A General Method of Synthesis of Condensed Pyrimidines", J. Heterocyclic Chemistry, BD, 17, 1, ISSN 0022-152X, Nov. 1980, p. 1497-1500.

Dave, Rutesh H. "Overview of pharmaceutical excipients used in tablets and capsules." Drug Topics, Oct. 24, 2008.

Deacon, Carolyn F., et al., "Linagliptin, a xanthine based dipeptyl peptidase-4 inhibitor with an unusual profile for the treatment of type 2 diabetes" Expert Opinion Investig. Drugs 2010, 19 (1) p. 133-140.

Deacon, C.F. et al.; "Dipeptidyl peptidase IV inhabitation as an approach to the treatment and prevention of type 2 diabetes: a historical perspective;" Biochemical and Biophysical Research Communications (BBRC) 294 (2002) 1-4.

Deacon, C.F., et al. Inhibitors of dipeptidyl peptidase IV: a novel approach for the prevention and treatment of Type 2 diabetes? Expert Opinion on Investigational Drugs, 2004, September, vol. 13, No. 9, p. 1091-1102.

Deacon, Carolyn F., "Dipeptidyl peptidase 4 inhibition with sitagliptin: a new therapy for Type 2 diabetes." Expert Opinion on Investigational Drugs, 2007, vol. 16, No. 4, pp. 533-545.

Definition of "prevent", e-dictionary, Aug. 15, 2013, http://dictionary.reference.com/browse/prevent.

Del Prato, Diabetes, Obesity and Metabolism, Effect of linagliptin monotherapy on glycemic control and markers of b-cell function in patients with inadequately controlled type 2 diabetes: a randomized controlled trial, 2011, p. 258-267.

Demeester, I. et al; "CD26, let it cut or cut it down", Review: Immunology Today; Aug. 1999, vol. 20, No. 8 pp. 367-375.

Demuth, H-U. et al., "Type 2 diabetes—Therapy with dipeptidyl peptidase IV inhibitors". Biochimica et Biophysica Acta, vol. 1751(1), 2005, p. 33-44.

Diabetes and Foot ulcers, www.diabetes.co.uk/diabetes-complications/diabetic-foot-ulcers.html, 2018.

Diabetes Frontier, 2007, vol. 18, No. 2, p. 145-148.

Diabetes Health Center, "Diabetic Retinopathy—Prevention." Retrieved online Mar. 22, 2011. www.diabetes.webmd.com/tc/diabetic-retinopathy-prevention <http://www.diabetes.webmd.com/tc/diabetic-retinopathy-prevention?print=true>.

Diabetes, Type 1 Diabetes-Associated Autoantibodies, 2009, vol. 52, Issue 8, p. 675-677.

Diabetesincontrol.com "EASD: Eucreas, a Combination of Galvus and Metformin, Recommended for Approval." Diabetes In Control. com, Sep. 25, 2007, Retrieved from internet on Nov. 30, 2012, http://www.diabetesincontrol.com/articles/53-diabetes-news/5145.

Diabetic Neuropathy, Retrieved online Mar. 6, 2012. www.mayoclinic.com/health/diabetic-neuropathy/DS01045/METHOD=print&DSE <http://www.mayoclinic.com/health/diabetic-neuropathy/DS01045/METHOD=print&DSE>.

DiFeo, Drug Product Development, A Technical Review of Chemistry, Drug Development and Industrial Pharmacy, vol. 29, 2003, p. 939-958.

Doopedia, Maillard Reaction.

Drucker, Daniel J., "Dipeptidyl Peptidase-4 Inhibition and the Treatment of Type 2 Diabetes." Diabetes Care, 2007, vol. 30, No. 6, pp. 1335-1343.

Drucker, et al., The incretin system: glucagon-like peptide-1 receptor agonists and dipeptidyl peptidase-4 inhibitors in type 2 diabetes. Lancet, 2006, 368: 1696-705.

Dugi, K. et al., "Safety, tolerability, pharmacokinetics, and pharmacodynamics of BI 1356, a novel DPP-IV inhibitor with a wide therapeutic window." Diabetic Medicine, 2006, vol. 23, Suppl. 4, p. 300.

Dunitz, J. et al., "Disappearing Polymorphs." Acc. Chem. Res. 1995, vol. 28, No. 4, pp. 193-200.

Eckhardt Matthias et al: 8-(3-(R)-aminopiperidin-1-yl)-7-but-2-yny 1-3-methyl-1-(4-methyl-quina zolin-2-ylmethyl)-3,7-dihydropurine-2,6-dione (BI 1356), a highly potent, selective, long-acting, and orally bioavailable DPP-4 inhibitor for the treatment of type 2 diabetes: Journal of Medicinal Chemistry, American Chemical Society. Washington.; US, vol. 50, No. 26, Dec. 1, 2007, p. 6450-6453.

Eckhardt, "-(3-(R)-Aminopiperidin-1-yl)7-but-2-ynyl-3-methyl-1-(4-methyl-quinazolin-2-ylmethyl-3,7-dihydropurine-2,6-dione (BI 1356), a highly potent, selective, long-acting, and orally bioavailable DPP-4 inhibitor for the treatment of type 2 diabetes", J. med. Chem, vol. 50, 2007.

(56) References Cited

OTHER PUBLICATIONS

Eckhardt, M. et al., "3,5-dihydro-imidazo[4,5-d]pyridazin-4-ones: a class of potent DPP-4 inhibitors" Bioorganic & Medicinal Chemistry Letters, Pergamon, Elsevier Science, GB, vol. 18, No. 11, Jun. 1, 2008, pp. 3158-3162, XP022711188.
Edosada, C. Y. et al. "Selective Inhibition of Fibroblast Activation Protein Protease Based on Dipeptide Substrate Specificity." The Journal of Biological Chemistry, 2006, vol. 281, No. 11, pp. 7437-7444.
Elrishi M A et al: "The dipeptidyl-peptidase-4 (D::-4) inhibitors: A new class of oral therapy for patients with type 2 diabetes mellitus" Practical Diabetes International Chichester, vol. 24, No. 9, Nov. 1, 2007 pp. 474-482.
EMEA Guidelines on Eucreas®, 2007, pp. 1-27.
EMEA Guidelines on Galvus®, 2007, pp. 1-34.
EMEA: European Medicines Agency, "Galvus (vildagliptin)" Retrieved online on Jan. 21, 2016.
EMEA: European Medicines Agency, ICH Topic E4, "Dose Response Information to Support Drug Registration." 1994, pp. 1-10.
Bollag, R.J. et al; "Osteoblast-Derived Cells Express Functional Glucose-Dependent Insulinotropic Peptide Receptors," Endocrinology, vol. 141, No. 3, 2000, pp. 1228-1235.
Borloo, M. et al. "Dipeptidyl Peptidase IV: Development, Design, Synthesis and Biological Evaluation of Inhibitors." 1994, Universitaire Instelling Antwerpen, vol. 56, pp. 57-88.
Bosi, E. et al., "Effects of Vildagliptin on Glucose Control Over 24 Weeks in Patients With Type 2 Diabetes Inadequately Controlled With Metformin." Diabetes Care, 2007, vol. 30, No. 4, pp. 890-895.
Boulton, D.W. et al., "Safety, Tolerability, Pharmacokinetics and Pharmacodynamics of Once-Daily Oral Doses of Saxagliptin for 2 Weeks in Type 2 Diabetic and Healthy Subjects." Diabetes, 2007, Supplement 1, vol. 56, pp. A161.
Brazg, R. et al: "Effect of adding sitagliptin, a dipeptidyll peptidase-4 inhibitor, to metformin on 24-h glycaemic control and beta-cell function in patients with type 2 diabetes." Diabetes, Obesity and Metabolism, Mar. 2007, vol. 9, No. 2, Mar. 2007 pp. 186-193.
Brazg, Ronald, et al; Effect of Adding MK-0431 to On-Going Metforming Therapy in Type 2 Diabetic Patients Who Have Inadequate Glycemic Control on Metformin; Diabetes ADA (2005) vol. 54, Suppl. 1 p. A3.
Brittain, H.G., "Methods for the Characterization of Polymorphs: X-Ray Powder Diffraction," Polymorphism in Pharmaceutical Solids, 1999, p. 235-238.
Brittain, Polymorphism on Pharmaceutical Solids, Chapter 5 Generation of Polymorphs, vol. 95, 1999, p. 183-226.
Bundgaard, H. "Design of prodrugs: Bioreversible derivatives for various functional groups and chemical entities". Royal Danish School of Pharmacy, 1985, p. 1-92.
Busso et al., "Circulating CD26 is Negatively Associated with Inflammation in Human and Experimental Arthritis," Am. J. Path., vol. 166, No. 2, Feb. 2005, pp. 433-442.
Byrn, Stephen R. "Solid-State Chemistry of Drugs." Academic Press, 1982, pp. 1-27.
Caira, M.R., "Crystalline polymorphism of organic compounds" Topics in Current Chemistry, Springer, Berlin, vol. 198, 1998, p. 163-208.
Campbell, R. Keith "Rationale for Dipeptidyl Peptidase 4 Inhibitors: A New Class of Oral Agents for the Treatment of Type 2 Diabetes Mellitus." The Annals of Pharmacotherapy, Jan. 2007, vol. 41, pp. 51-60.
Canadian Diabetes Association, "Pharmacologic Management of Type 2 Diabetes." Canadian Journal of Diabetes, 2003, vol. 27, Suppl. 2, pp. S37-S42.
Canadian Pharmacists Association, Compendium of Pharmaceuticals and Specialties, "Zestril" 2004, pp. 2289-2293.
Cao, C. et al., "The clinical application of linagliptin in Asians." Therapeutics and Clinical Risk Management, 2015, vol. 11, pp. 1409-1419.

Castello, R. et al., "Discoloration of Tablets Containing Amines and Lactose." Journal of Pharmaceutical Sciences, 1962, vol. 51, No. 2, pp. 106-108.
Cefalu, Animal Models of Type 2 Diabetes: Clinical Presentation and Pathophysiological Relevance to the Human Condition, ILAR Journal, vol. 47, No. 3, 2006.
Chan, J.C. et al., "Safety and efficacy of sitagliptin in patients with type 2 diabetes and chronic renal insufficiency." 2008, Diabetes, Obesity and Metabolism, vol. 10, pp. 545-555.
Charbonnel, B. et al., "Efficacy and Safety of the Dipeptidyl Peptidase-4 Inhibitor Sitagliptin Added to Ongoing Metformin Therapy in Patients With Type 2 Diabetes Inadequately Controlled With Metformin Alone." Diabetes Care, 2006, vol. 29, No. 12, pp. 2638-2643.
Chaykovska, L. et al., "Effects of DPP-4 Inhibitors on the Heart in a Rat Model of Uremic Cardiomyopathy." www.plosone.org, 2011, vol. 6, No. 11, p. e27861.
Chemgaroo, "Leaving Group." 1999, Retrieved online: http://www.chemgapedia.de/vsengine/vlu/vsc/en/ch/12/oc/vluorganik/substitution/sn_2/sn2.vlu/Page/vsc/en/ch/12/oc/substitution/sn_2/abgangsgrupen/abgangsgruppe.vscml.html.
Chemical Abstract. EP412358, 1991:185517, Findeisen.
Chemical Abstract: FR2707641, 1995:543545, Dodey.
Chemical Abstract: No. 211513-37-0—Dalcetrapib. "Propanethioic acid, 2-methyl-, S-(2-(((1-(2-ethylbutyl)cyclohexyl)carbonyl)amino)pheyl)ester". Formula: C23 H35 N O2 S. American Chemical Society. Sep. 20, 1998.
Chemical Abstract: No. 875446-37-0—Anacetrapib. "2-Oxazolidinone, 5-[3,5-bis(trifluoromethyl)phenyl]-3[[4'fluoro-2'-methoxy-5'-(1-methylethyl)-4-(trifluoromethyl)[1, 1'-biphenyl]-2-yl]methyl]-4-methyl-,(4S,5R)-" Formula: C30 H25 F10 N 03. American Chemical Society, Feb. 28, 2006.
Chemical Abstracts Accession No. 106:95577 Romanenko et al., "Synthesis and Biological Activity of 3-Methyl, 7- or 8-alkyl-7,8dialkyl, heterocyclic, and cyclohexylaminoxanthines," Zaporozh. Med. Institute (1986).
Chemical Abstracts Accession No. 1987:95577: Abstract of Romanenko et al., "Synthesis and biological activity of 3-methyl, 7- or 8-alkyl, 7,8-dialkyl, heterocyclic, and cyclohexylaminoxanthines," Zapoeozh, USSR, Farmatsevtichnii Zhurnal, 1986, (Kiev), vol. 5, 1986, pp. 41-44.
Chemical Abstracts Service, Database Accession number No. RN 668270-12-01, 2004, "1H-Purine-2,6-dione, 8-[(3R)-3-amino-1-piperidinyl]-7-(2-butyn-1-yl)-3,7-dihydro-3-methyl-1-[(4-methyl-2-quinazolinyl)methyl]".
Chemistry Review: Tradjenta, "NDA 201280, CMC Director Review Tradjenta (Linagliptin) Tablets." Center for Drug Evaluation and Research, Aug. 9, 2010, Retrieved from the internet on Nov. 1, 2013, http://www.accessdata.fda.gov/drugsatfda_docs/nda/2011/201280Orig1s000ChemR.pdf.
Cheon, et al., Biochemical Pharmacology, "Inhibition of dipeptidyl IV by novel inhibitors with pyrazolidine scaffold", 2005, vol. 70, p. 22-29.
Chiasson, J.-L. et al., "The Synergistic Effect of Miglitol Plus Metformin Combination Therapy in the Treatment of Type 2 Diabetes." Diabetes Care, 2001, vol. 24, No. 6, pp. 989-994.
Chisari, A. et al. "Sulphinyl, Sulphonyl, and Sulphonium Groups as Leaving Groups in Aromatic Nucleophilic Substitutions." Journal of the Chemical Society, Perkin Transactions II, 1982, pp. 957-959.
Chowhan, Z.T. et al., Drug-Excipient Interaction Resulting from Powder Mixing IV: Role of Lubricants and Their Effect on In Vitro Dissolution, Journal of Pharmaceutical Sciences, 1986, vol. 75, No. 6, pp. 542-545.
Clinical Journal of Chinese Medicine, vol. 3, 2008, p. 360-364.
Clinical Trial NCT00622284 (published online at clinicaltrials.gov on Feb. 22, 2008).
Clinical Trial Protocol, "A Randomised, Double-blind, Placebo-controlled, Five Parallel Groups Study Investigating the Efficacy and Safety of BI 1356 BS." Boehringer Ingelheim Pharmaceuticals, last updated on Jun. 24, 2014.
Clinical Trial results of Tradjenta Tablet, Center for Drug Evaluation and Research, 2010.

(56) References Cited

OTHER PUBLICATIONS

Clinical Trial, NCT00622284, clinicaltrials.gov, updated Feb. 22, 2008.
Clinical Trials NCT00601250, clinicaltrials.gov, Jan. 25, 2008.
Clinical trials, A Randomized, Double Blind, Active Controlled parallel Group Efficacy and Safety Study of BI 1356 Compared to Glimepiride over 2 years in Type 2 Diabetic Patients with insufficient glycemic control despite metformin therapy, https://clinicaltrials.gov/archive/NCT00622284/20120606, 2008.
Clinical Trials, No. NCT00309608, "Efficacy and Safety of BI 1356 BS in Combination with Metformin in Patients With type2 Diabetes" 2009, pp. 1-3.
Clinical Trials, No. NCT00622284, "Efficacy and Safety of BI 1356 in combination with metformin in patients with type 2 diabetes" 2012, pp. 1-5.
Clinical Trials. "View of NCT00601250 on Jan. 25, 2008: Efficacy and Safety of BI 1356 vs Placebo added to Metformin Background Therapy in Patients with Type 2 Diabetes" Clinical Trials. Gov Archive, [Online] Jan. 25, 2008 URL:http://clinicaltrials.gov/archive/NCTO0601250/2008_01_25 [retrieved on Feb. 27, 2009].
Clinical Trials. NCTO0622284. "Efficacy and safety of BI 1356 in combination with metformin in patients with type 2 diabetes" ClinicalTrials.gov (Online) No. NCT00622284, Feb. 13, 2008, p. 1-5, URL:http://clinicaltrial.gov/ct2/show/.
Clinical Trials. View of NCT00730275 updated on Aug. 7, 2008. "A study to assess the pharmacokinetics, safety and tolerability of Sitagliptin in adolescents". http://clinicaltrials.gov/archive/NCT00730275/2008_08_07.
Clinical Trials.gov, 52-week add-on to metformin comparison of saxagliptin and sulphonurea, NCT00575588, 2007.
Clinical Trials.gov, Efficacy and Safety of BI 1356 in Combination with Metformin in Patients with Type 2 Diabetes, NCT00309608, 2006.
Clinical Trials.gov, Efficacy and Safety of Lingliptin in Elderly Patients with Type 2 Diabetes, Mar. 10, 2010, NCT01084005.
Clinical Trials.gov, NCT00622284, Efficacy and Safety of BI 1356 in Combination with Metformin in Patients with Type 2 Diabetes, 2013.
Piatti, Long term Oral L-Arginine-Administration Improves Peripheral and Hepatic Insulin Sensitivity, Emerging Treatments and Technology, Diabetes Care, vol. 24, 2011, 6 pages.
Rai, Effect of Glycemic Control on apoptosis in diabetic wounds, Journal of Wound care, vol. 14, 2005, 5 pages.
Remington , The Science of Pharmacy, 22nd Ed., Pharmaceutical Dosage Forms, 2013.
Report on the deliberation results Trazenta Tablets, 2011, 91 pages.
Ristic, Diabetes, Obesity and Metabolism, Improved Glycemic Control with dipeptidyl peptidase-4 inhibition in patients in patients with type 2 diabetes, 2005, 8 pages.
Thielitz, Inhibitors of Dipeptidyl Peptidase IV and aminopeptidase N target Major Pathogenetic steps in Acne initiation, Journal of inventigative Dermatology, 2007, 10 pages.
Van Veen, Compaction of Powder blends, University Medical Center, 2003, 128 pages.
Von Eynatten, Efficacy and safety of linagliptin in type 2 diabetes subjects at high risk for renal and cardiovascular disease, vol. 12, 2013, 2 pages.
Walsh, Pharmaceutical Biotechnology, Overview of Protein structure, 2007, 5 pages.
Wertheimer, et al., "Drug Delivery Systems improve pharmaceutical profile and faciliate medication adherence", Adv. Therapy 22: 2005, p. 559-577.
Winzell, Diabetes, The High Fat diet fed Mouse, vol. 53, 2004, 5 pages.
Wufele, Combination of Insulin and Metformin in Treatment, Clinical Care, vol. 25, 2002, 8 pages.
Wu, Primacy of the 3b Approach to Control risk factors for Cardiovascular disease in type 2 diabetes patients Diabetes Mellitus and Cardio Disease, People's Military Press, 2005, 12 pages.

Cooper, Kidney Disease End Points in a Pooled Analysis of individual Patient-Level Data from a large Clinical Trials Program of the Dipeptyl Peptidase 4 Inhibitor Linagliptin in Type 2 Diabetes, vol. 66, American Journal of Kidney Diseases, 2015, 2 pages.
Gorrell, Fibroblast Activation Protein, Handbook of Proteolytic Enzymes, 3rd ed., 2013, 7 pages.
Rowe, Handbook of Pharmaceutical Excipients, Fifth Ed., Calcium Bicarbonate, 2006, 50 pages.
Roy, Pharmaceutical Impurities, PharmSciTech, Submitted Dec. 12, 2001, Accepted 2001, Published 2002, vol. 3, 2 pages.
Scheen, Lina plus metformin, Expert opinion on Drug metabolism & Toxicology, vol. 9, 2013, p. 363-377.
Wettergren, Truncated GLP-1, Inhibits Pancreatic and Gastric Functions in Man, vol. 38, 1993, p. 665-673.
Hahr, Management of diabetes mellitus in patients with chronic kidney disease, Clinical Diabetes and Endocrinology, vol. 10, 2015, 9 pages.
Duong, Population pharmacokinetics of metformin in healthy subjects and patients with type 2 diabetes, Clinical Pharmacokinetics, vol. 52, 2013, p. 373.
Bell, Prescribing for older people with chronic renal impairment, Australian Family Physician, vol. 42, 2013, 5 pages.
Munar, Drug dosing adjustments in patients with chronic kidney disease, AFP, vol. 75, 2007, 10 pages.
Laasko, Hyperglycemia and Cardiovascular Disease in Type 2 Diabetes, Diabetes, vol. 48, 1999, 6 pages.
Haffner, Mortality from coronary heart disease in subjects with type 2 diabetes and in nondiabetic subjects with and without prior myocardial infarction, The N.E. J. of Medicine, vol. 339, 1996, 6 pages.
Summary of report characteristics, Trajenta, no year.
Calles, Type 2 diabetes, Coronary Artery Disease, vol. 10, 1999, 8 pages.
Marks, Cardiovascular Risk in Diabetes, Journal of Diabetes and the complications, vol. 14, 2000, 8 pages.
Fadini, DPP-4 inhibition has no cute affect on BNP and its N-terminal pro-hormone measured by commercial immune assays, Cardiovascualr Diabetology, vol. 16, 2017, 7 pages.
Mu, Impact of DPP-4 inhibitors on plasma levels of BNP and NT-pro-BNP in type 2 diabetes mellitus, Diabetology, vol. 14, 2022, 9 pages.
McGuire, Linagliptin effects on heart failure and related outcomes in individuals with type 2 diabetes mellitus, http://shjajournals.org on Mar. 18, 2023, 11 pages.
Clifton, Do dipeptidyl Peptidase IV inhibitors cause heart failure?, Clinical therapeutics, vol. 36, 2014, 8 pages.
Shiraki, The DPP4 inhibitor linagliptin exacerbated heart failure due to energy deficiency, Pharmcology and Pharmacotherapy, downloaded from http://academic.cup.com/eurheartj/article/43/supplement_2/ehcac544268/26746435 Mar. 18, 2023.
Mu, Impact of DPP-4 inhibitors on plasma levels of BNP and NT-pro-BNP in type 2 diabetes mellitus, Diabetology and Diabetes Mellitus, vol. 14, 2022, 9 pages.
Kroller-Schuhmacher, Comparison of direct and indirect antioxidant effects of linagliptin with other gliptins, Vascular Pharmacology, vol. 56, 2012, p. 352.
Schuff, Comparison of the Direct and indirect Antioxidant Effects of DPP-4 Inhibitors, retrieved from https://professional.diabetes.org/abstract/comparison-direct-and-indirect-antioxidant-effects-dpp-4-inhitors-anti-inflammatory 2011, 1 page.
Singh, Sepsis in diabetes, Diabetes and metabolic Syndrome, Clinical Research and Reviews, vol. 5, 2011, p. 222-227.
Fink, Animal models of sepsis and its complications, Kidney International, vol. 74, 2008, p. 991-993.
Galley, Oxidative stress and mitochondrial dysfunction in sepsis, British J. of Anaesthesia, vol. 107, 2011, p. 57-64.
Baudouin, Sepsis, Springer-Verlag, vol. 88, 2008, p. 1-4.
Freeman, Efficacy and Safety of Linagliptin in Adults with type 2 diabetes, vol. 36, 2011, p. 807-842.
UK Prospective Diabetes Study Group, Intensive blood glucose control with sulphonylureas or insulin compared withconventional treatment and risk of complications in patients with type 2 diabetes, The Lancet, vol. 352, 1998, p. 837-853.

(56) References Cited

OTHER PUBLICATIONS

Scherbaum, Sepsis, Psychyrembel Worterbach Diabetologie, 2003.
Schuermann, The Didpeptidyl Peptidase-4 inhibitor linagliptin attentuates inflammation and accelerates epitheliaixation in wounds of diabetic ob/ob mice, J. of pharmacology and experimental therapeutics, 2012, 8 pages.
Arenson, Neuropathy, Aniopathy, and sepsis in the diabetic foot, J. of american Podiatry assoc., vol. 72, 1982, p. 35-40.
Andrades, Bench to bedside review, Sepsis, from the redox point of view, Clinical care, vol. 15, 2011, 8 pages.
Holt, Textbook of Diabetes, 4th Ed., 2010, 48 pages.
Lee, Recent advances in the treatment of diabetes mellitus, Korean J. of Medicine, vol. 57, 1999, p. 836-848.
The Japan Diabetes Society, Practice Guidelines of Diabetes based on Scientific basis, May 25, 2004, p. 5-19, p. 37-56, p. 67-80, p. 93-121, p. 131-153.
Toshiaki, ABC18 for new diagnostics and treatments, The medical frontline, 2004, p. 106-112.
Rinsho-Yakuri, Jpn. J. Clin. Pharmacol. Ther. Pharmacokinetics: excretion, 30(3) 1999. 2 pages.
Rosenbloom, et al., "Type 2 Diabetes mellitus in the child and adolescent", Pediatric Diabetes, 2008, p. 512-526.
Rosenstock, et al., "Efficacy and tolerability of initial combination therapy with vildagliptin and pioglitazone compared with component montherapy in patients with type 2 diabetes". Diabetes, Obesity and Metabolism, Mar. 2007, vol. 9, No. 2, p. 175-185.
Rosenstock, et al., Sitagliptin Study 019 Groups, Efficacy and safety of the dipeptidyl peptidase-4 inhibitor sitagliptin, Clinical Therapeutics, 2006, vol. 28, Issue 10, p. 1556-1568.
Rosenstock, J. et al., "Alogliptin added to insulin therapy in patients with type 2 diabetes reduces HbA1c without causing weight gain or increased hypoglycaemia". Diabetes, Obesity and Metabolishm, Dec. 2009, vol. 11. No. 12, p. 1145-1152.
Rosenstock, J. et al., "Triple Therapy in Type 2 Diabetes." Diabetes Care, 2006, vol. 29, No. 3, pp. 554-559.
Rowe, R. et al., Handbook of Pharmaceutical Excipients, Fourth Edition, Pharmaceutical Press and American Pharmaceutical Association, 2003, pp. 323-332., 373-377, 609-611.
Russell-Jones, D. et al., "Liraglutide vs insulin glargine and placebo in combination with metformin and sulfonylurea therapy in type 2 diabetes mellitus (LEAD-5 met+SU): a randomised controlled trial." Diabetologia, 2009, vol. 52, pp. 2046-2055.
Salomon, J., et al; Ultraviolet and g-Ray-Induced Reactions of Nucleic Acid Constituents. Reactions of Purines with Amines; Photochemistry and Photobiology (1974) vol. 19 pp. 21-27.
Sarafidis, P. et al., "Cardiometabolic Syndrome and Chronic Kidney Disease: What is the link?"JCMS 2006, 1: p. 58-65.
Sathananthan, A., et al., "Personalized pharmacotherapy for type 2 diabetes mellitus". Personalized Medicine 2009 Future Medicine Ltd, vol. 6, No. 4, Jul. 2009, p. 417-422.
Sauer, R, et al. "Water-soluble phosphate prodrugs of 1-Propargyl-7-styrylxanthine derivatives, A2A-selective adenosine receptor antagonists". Journal Med. Chem., vol. 43, Issue 3, Jan. 2000, p. 440-448.
Scheen, Clinical Pharmacokinetics of metformin, Clinical Pharmacokinetics, vol. 30, No. 5, 1996, p. 359-371.
Scheen, Efficacy and Safety of Jentadueto, Expert Opinion on Drug and Safety, vol. 12, No. 2, 2013, p. 275-289.
Schillinger, M. et al., "Restenosis after percutaneous angioplasty: the role of vascular inflammation." Vascular Health and Risk Management, 2005, vol. 1, No. 1, pp. 73-78.
Schmidt, D. et al., "Fibromatosis of Infancy and Childhood Histology, Ultrastructure and Clinicopathologic Correlation." Zeitschrift für Kinderchirurgie, 1985, vol. 40, No. 1, pp. 40-46.
Schnapp, G. et al., "Analysis of binding kinetics and thermodynamics of DPPIV Inhibitors and their relationship to structure." International Workshop: The aspect of time in drug design, Schloss Rauischholzhausen, Marburg, Germany, Mar. 24-27, 2014.
Schnapp, G. et al., "Comparative Enzyme Kinetic Analysis of the Launched DPP-4 Inhibitors." American Diabetes Association, Abstract 1048-P, 2014.

Schurmann, C. et al., "The Dipeptidyl Peptidase-4 Inhibitor Linagliptin Attenuates Inflammation and Accelerates Epithelialization in Wounds of Diabetic ob/ob Mice." The Journal of Pharmacology and Experimental Therapeutics, 2012, vol. 342, No. 1, pp. 71-80.
Schwartz, M. S. et al., "Type 2 Diabetes Mellitus in Childhood: Obesity and Insulin Resistance". JAOA Review Article, vol. 108, No. 9, Sep. 2008, p. 518.
Scientific Discussion for Sifrol, European Public Assessment Reports, 2005, p. 1.
Scientific Discussion on Sifrol, EMEA, 2005, p. 1-9.
Scientific Discussion, EMEA, Pramipexole, 2005, pp. 1-10.
Scientific Discussion: "Eucreas. Scientific discussion". Online Oct. 2007, p. 1-27, URL:http://www.emea.europa.eu/humandocs/PDFs/EPAR/eucreas/H-807-en6.pdf. see point 2. quality aspects pp. 2-4. (EMEA).
Sedo, A. et al; "Dipeptidyl peptidase IV activity and/or structure homologs: Contributing factors in the pathogenesis of rheumatoid arthritis?" Arthritis Research & Therapy 2005, vol. 7, pp. 253-269.
Seijin-Byou, The Journal of Adult Diseases, 2008, vol. 38, p. 438-444., abstract attached.
Seino, Alogliptin plus voglibose in Japanese patients with type 2 diabetes: a randomized, double blind, placebo-controlled trial with an open label, long term extension, Current Medical Research and Opinion, 2011, vol. 27, p. 21-29.
Shanks, N. et al., Are animal models predictive for humans?, PEHM, Philosophy, Ethics, and Humanaities in Medicine, 4(2), 2009, 1-20.
Sharkovska, Y., et al., "DPP-4 Inhibition with Linagliptin Delays the Progression of Diabetic Nephropathy in db/db Mice." 48th EASD Annual Meeting, Berlin, Abstract 35, Oct. 2012.
Sheperd, Todd M. et al., "Efective management of obesity." The Journal of Family Practice, 2003, vol. 52, No. 1, pp. 34-42.
Shigai, "How to use medicines in case of kidney injury caused by medicine" Journal of the Japanese Association of Rural Medicine, vol. 51, 2002, p. 63-67.
Shintani, Maki, et al., "Insulin Resistance and Genes" Circulatory Sciences (1997) vol. 17, No. 12 pp. 1186-1188.
Shu, L. et al., "Decreased TCF7L2 protein levels in type 2 diabetes mellitus correlate with downregulation of GIP- and GLP-1 receptors and impaired beta-cell function." Human Molecular Genetics, 2009, vol. 18, No. 13, pp. 2388-2399.
Shu, L. et al., "Transcription Factor 7-Like 2 Regulates B-Cell Survival and Function in Human Pancreatic Islets." Diabetes, 2008, vol. 57, pp. 645-653.
Silverman, G. et al., "Handbook of Grignard Reagents." 1996, Retrieved online: <http://books.google.com/books?id=82CaxfY-uNkC&printsec=frontcover&dq=intitle:Handbook+intitle:of+intitle:Grignard+intitle:Reagents&hl=en&sa=X&ei=g06GU5SdOKngsATphYCgCg&ved=0CDYQ6AEwAA#v=onepage&q&f=false>.
Singhal, D. et al., "Drug polymorphism and dosage form design: a practical perspective." Advanced Drug Delivery Reviews, 2004, vol. 56, pp. 335-347.
Slotta, On Biguanides, Chem. Institute at the Univ. of Wroclaw, vol. 62, 1929.
Sortino, M.A. et al., "Linagliptin: a thorough characterization beyond its clinical efficacy." Frontiers in Endocrinology, 2013, vol. 4, Article 16, pp. 1-9.
St. John Providence Health Center, "Preventing Obesity in Children and Teens." Retrieved from internet on Aug. 22, 2013, http://www.stjohnprovidence.org/Health I nfoLib/swarticle.aspx?type=85&id=P07863.
Stahl, Handbook of Pharmaceutical Salts, Properties, Selection and Use, 2002.
Stahl, P. H., "Handbook of Pharmaceutical Salts" C.G. Wermuth, Wiley-VCH, 2002, pp. 1-374.
Standl, E. et al., "Diabetes and the Heart." Diabetes Guidelines (DDG), 2002, pp. 1-25.
Sulkin, T.V. et al., "Contraindications to Metformin Therapy in Patients With NIDDM." Diabetes Care, 1997, vol. 20, No. 6, pp. 925-928.
Sune Negre, J. M. "New Galenic Contributions to Administration Forms". Continued Training for Hospital Pharmacists 3.2., (Publi-

(56) References Cited

OTHER PUBLICATIONS cation date unavailable), Retrieved from internet on Feb. 23, 2011, http://www.ub.es/legmh/capitols/sunyenegre.pdf.

Susman, Ada: Linagliptin Works in Diabetic Kidney Disease, Med Page Today, 2011, 2 pages.

Suzuki, Y. et al., "Carbon-Carbon Bond Cleavage of a-Hydroxybenzylheteroarenes Catalyzed by Cyanide Ion: Retro-Benzoin Condensation Affords Ketones and Heteroarenes and Benzyl Migration Affords Benzylheteroarenes and Arenecarbaldehydes." Chemical Pharmaceutical Bulletin, 1998, vol. 46(2), pp. 199-206.

Tadayyon, M. et al., "Insulin sensitisation in the treatment of Type 2 diabetes." Expert Opinion Investigative Drugs, 2003, vol. 12, No. 3, pp. 307-324.

Takai, S. et al., "Significance of Vascular Dipeptidyl Peptidase-4 Inhibition on Vascular Protection in Zucker Diabetic Fatty Rats." Journal of Pharmacological Sciences, 2014, vol. 125, pp. 386-393.

Takeda Press Release: "Voglibose (BASEN) for the prevention of type 2 diabetes mellitus: A Randomized, Double-blind Trial in Japanese Subjects with Impaired Glucose Tolerance." 2008, Retrieved online Jul. 6, 2015. https://www.takeda.com/news/2008/20080526_3621.html.

Tamm, E, et al., "Double-blind study comparing the immunogenicity of a licensed DTwPHib-CRM197 conjugate vaccine (Quattvaxem ™) with three investigational, liquid formulations using lower doses of Hib-CRM197 conjugate". Science Direct, Vaccine, Feb. 2005, vol. 23, No. 14, p. 1715-1719.

Deshpande, American Physical Therapy Assoc., Epidemiology of Diabetes related complications, 2008, vol. 88, 10 pages.

Deacon, Linagliptin, a xanthing based dipeptidyl peptidase 4 inhibitor, Informa Healthcare, vol. 19, 2010, 8 pages.

De galan, Theophylline Improves Hypoglycemia Unawareness, Diabetes, vol. 51, 2002, 7 pages.

Crowley, Drug-Excipient interactions, Pharma Tech Europe, vol. 13, 2001, 9 pages.

Eynatten, Efficacy and safety of linagliptin in type 2 diabetes-subjects, Cardiovascular diabetology, vol. 12, 2009, 1 page.

Fadini, The oral Dipeptidyl Peptidase-4 Inhibitor Sitagliptin Increases Circulating Endothelial Progenitor Cells in Patients with Type 2 Diabetes, Diabetes Care, vol. 33, 2010, 3 pages.

Abdoh, Amlodipine besylate excipients interaction in solid dosage form, Pharmaceutical Development and Technology, vol. 9, 2004, 10 pages.

Drucker, Glucagon-like peptide I stimulates insulin gene expression and increases cyclic AMP levels in a rat islet cell line, Proc. Natl. Acad. Sci, vol. 84, p. 97.

Groop, P.-H. et al., "Effects of the DPP-4 Inhibitor Linagliptin on Albuminuria in Patients with Type 2 Diabetes and Diabetic Nephropathy." 48th EASD Annual Meeting, Berlin, Abstract 36, Oct. 2012, 1 page.

Gross, Diabetic Neuropathy, Diabetes Care, vol. 28, 2005, 13 pages.

Haak, Comibination of Linaglptin and metformin, Clinical Med insights, 2015, 10 pages.

Herrington, Metformin, Effective ans safe in renal Disease? Int. Urol. Nephrol. vol. 40, 2008, 7 pages.

Hu, Diabetes Mellitus and Heart Disease, People's Military Press, 2005, 12 pages.

Hu, Research and Application, Biomedical Info in Translational Research, 2008, 20 pages.

Bruni, Drug Excipient compatibility, Journal of Thermal Analysis and Calorimetry, vol. 68, 2002, 13 pages.

Bruni, Drug Excipient Compatibility Studiesm J. of Thermal Analysis, 2018, 1 page.

Deutsche Evidenzbasierte Diabetes-Leitlinien, Diabetes and Herz, 2002 1 page.

Ahren, Dipetidyl Peptidase-4 Inhibitors, Diabetes Care, vol. 30, 2007, 7 pages.

Ahren, Emerging Dipeptyl peptidase-4 inhibitors for the treatment of diabetes, Expert Opinion on Emerging Drugs, vol. 13, 2008, 20 pages.

Falanga, Lancet, Wound healing and impairment in the diabetic foot, vol. 366, 2005, 7 pages.

Gohel, A review of coprocessed Directly compressible excipients, J. Pharm Pharmaceutical Sci, 2005 p. 76-93.

Graefe-Mody, Evaluation of the Potential for steady state phamracokinetic and pharmacodynamic interactions between the DPP-4 inhibitor linagliptin and metformin, Current Medical Research and Opinion, vol. 25, 2009, 10 pages.

Hasanato, Diagnostic Efficacy of random albumin creatinine ration, Saudi Med, J., 2016, vol. 37,6 pages.

Heise, Pharmacokinetics, pharmacodynamics, and tolerablity of mutiple does of linagliptin, Diabetes, Obesity and Metabolism, vol. 11, 2009, 0 pages.

Januvia Medication Guide, 2010, 4 pages.

Johansen, Diabetes Care, C-peptide Levels in latent Automimmune Diabetes in Adults treated with Linagliptin vs. Glimepiride, vol. 37, 2014 p. e11-e12.

Kaji, Dipeptidyl peptidase-4 inhibitor attenuates hepatic fibrosis via suppression of activated hepatic stellate cell in rats, J. Gastro, 2012, 11 pages.

Katdare, Excipient Development for Pharmaceutical Biotechnology and Drug Delivery Systems, Ten of the most common Neutralizers Used, 2006, 4 pages.

Kern, Linagliptin Improves Insulin Sensitivity, PLOSONE, vol. 7. 2012, 10 pages.

Kosugi, eNOS Knockout Mice with advanced diabetic neuropathy have less benefir from Renin-Angiostatin Blockade than from Aldosterone Receptor Antagonists, Amer. J. of Pathology, vol. 176, 2010, 11 pages.

Lee, Drug delivery system and pharmaceutical preparation, 2003. 13 pages.

Lehrke, Safety and Efficacy of linagliptin in patients with Type 2 diabetes, Journal of Diabetes, vol. 30, 2016 p. 1375-1384.

Levien, Diabetes Spectrum, New Drugs in Development for the Treatment of Diabetes, vol. 22, 2009, 18 pages.

Li, Glucagen like Peptide 1 Receptor Signaling Modulates b cell apoptosis, Journal of Biological Chem, 2003, p. 471-478.

Lide, CRC Handbook of Chem and Physics, Disassociation Constants of Organic Acids and Bases, 2002, 82nd Ed, 3 pages.

Lu, "High prevlaence of albuminuria in population based patients diagnosed with type 2 diabetes in the Shanghai downtown", Diabetes Research and Clinical Practice (2007) 184-192.

Laugesen, Latent Autoimmune diabetes of the adult: current knowledge and uncertainty, Diabetic Meds, vol. 10, 2015., 10 pages.

Lovshin, Incretin based therapies for type 2 diabetes mellitus, Nature, vol. 5, 2009, 8 pages.

MacDonald, No Fraud, no conspiracy, no error, France and Merck say reformulated Euthyrox is safe, Pharmatechnolgist, 2017, 3 pages.

Mark, A novel and Selective Xanthine Based Competitive DPP-IV Inhibitor, Diabetes, vol. 56, 2007, 2 pages.

McGill, Long term Efficacy and Safety of Linaglip in patients with Type 2 diabetes, Clinical Care, vol. 35, 2013, p. 237-244.

Mcintosh, Dipeptidyl Synthase IV inhibitors, Regulatory Peptides, vol. 128, 2005. p. 159-165.

Mclennan, Molecular aspects of wound healing in diabetes, Dept. of Endocrinology, Univ of Sydney, vol. 14, 2006, 5 pages.

Menielly, Diabetes in Elderly adults, J. of Gerontology, vol. 56A, 2001, 9 pages.

Merck Index, 15th Ed., Linagliptin, 2013. 2 pages.

Ohlden, New data from Boehringer INgelheim's Ongoing Linagliptin Trial Programme Shows Promising Safety and Efficacy results, Newswire, 2020, 7 pages.

Okruhlicova, Cell Research, Ultrastructure and Histchemistry of rat capilary endothelial cells in response to diabetes, vol. 15, 2005, 7 pages.

Owens, Efficacy and Safety of linagliptin in person with type 2 diabetes, Diabetic Meds, vol. 28, 2021. 2 pages.

Pearson, Variation in TCF7L2Influences Therapeutic Response to Sulfonylreas, Diabetes, vol. 56, 2007, 5 pages.

Peticao, Diagnosis and Classification of Diabetes Mellitus, Diabetes Care, vol. 37, 2014, 10 pages.

(56) References Cited

OTHER PUBLICATIONS

Ennis, Handbook of Pharmaceutical Granulation Technology, Theory of Granulation, 2010.
EU Clinical Trial Register, "A multicenter, international, rendomized, parallel group, double-blind, placebo-controlled, cardiovascular safety and renal microvascular outcome study with linagliptin, 5 mg once daily in patients with type 2 diabetes mellitus at high vascular risk." Aug. 19, 2015.
Eucreas Scientific Discussion, 2007, p. 1-27, www.emea.europa.eu/humandocs/PD/Fs/EPAR/eucreas/H-807-en6.pdf, Anonymous.
European Search Report for EP 08 15 9141 mailed Apr. 6, 2009 (European counterpart of U.S. Appl. No. 12/143,128).
Eyjolfsson, Reynir "Lisinopril-Lactose Incompatibility." Drug Development and Industrial Pharmacy, 1998, vol. 24, No. 8, pp. 797-798.
Fantus, George, "Metformin's contraindications: needed for now." Canadian Medical Association Journal, 2005, vol. 173, No. 5, pp. 505-507.
Federal register, Department of Health and Human Services, vol. 62, 1997, 4 pages.
Feng, J. et al., "Discovery of Alogliptin: A Potent, Selective, Bioavailable, and Efficacious Inhibitor of Dipeptidyl Peptidase IV." Journal of Medicinal Chemistry, 2007, vol. 50, No. 10, pp. 2297-2300.
Ferreira, L. et al., "Effects of Sitagliptin Treatment on Dysmetabolism, Inflammation, and Oxidative Stress in an Animal Model of Type 2 Diabetes (ZDF Rat)." Mediators of Inflammation, 2010, vol. 2010, pp. 1-11.
Ferry, Robert Jr., "Diabetes Causes." eMedicine Health, MedicineNet.com, 2013, Retrieved from internet on Aug. 22, 2013, <http://www.onhealth.com/diabetes_health/page3.htm#diabetes_causes>.
Fiorucci, et al. Trends in Molecular Medicine, Targeting farnesoid X receptor for liver and metabolic disorders, 13(7), 2007, p. 298-309.
Flatt, P.R. et al., "Dipeptidyl peptidase IV (DPP IV) and related molecules in type 2 diabetes." Frontiers in Bioscience, 2008, vol. 13, pp. 3648-3660.
Florez, J. et al. "TCF7L2 Polymorphisms and Progression to Diabetes in the Diabetes Prevention Program." The New England Journal of Medicine, 2006, vol. 355, No. 3, pp. 241-250.
Forst, T. et al., "The Novel, Potent, and Selective DPP-4 Inhibitor BI 1356 Significantly Lowers HbA1c after only 4 weeks of Treatment in Patients with Type 2 Diabetes." Diabetes, Jun. 2007, Poster No. 0594P.
Forst, T. et al., "The oral DPP-4 inhibitor linagliptin significantly lowers HbA1c after 4 weeks of treatment in patients with type 2 diabetes mellitus." Diabetes, Obesity and Metabolism, 2011, vol. 13, pp. 542-550.
Freeman, Initial Combination therapy for patients with type 2 diabetes mellitus, Drugs in Context, 2013, p. 212256., 6 pages.
Fuguchi, Therapeutic Effects and Adverse Reactions to Oral Hypoglycemic Agents, Journal of the Nippon Hospital Pharmacists Assoc, 1976, vol. 1, p. 226-229, abstract only.
Fukushima et al., Drug for Treating Type II Diabetes (6), "action-mechanism of DPP-IV inhibitor and the availability thereof" Mebio, 2009, vol. 26, No. 8, pp. 50-58.
Gall, "Prevalence of micro-and macroalbuminuria, arterial hypertension, retinopathy and large vessel disease in European type 2 (non-insulin dependent) diabetic patients", Diabetologia (1991) 655-661.
Gallwitz, B. "Sitagliptin with Metformin: Profile of a Combination for the Treatment of Type 2 Diabetes". Drugs of Today, Oct. 2007, 43(10), p. 681-689.
Gallwitz, B. et al., "2-year efficacy and safety of linagliptin compared with glimepiride in patients with type 2 diabetes inadequately controlled on metformin: a randomised, double-blind, non-inferiority trial." Lancet, 2012, vol. 380, pp. 475-483.
Gallwitz, B. et al., "Saxagliptin, a dipeptidyl peptidase IV inhibitor for the treatment of type 2 diabetes". IDRUGS, vol. 11, No. 12, Dec. 2008, p. 906-917.
Gallwitz, B. et al., DPP IV inhibitors for the Treatment of Type 2 Diabetes; Diabetes Frontier (2007) vol. 18, No. 6 pp. 636-642.
Gallwitz, B., "Safety and efficacy of linagliptin in type 2 diabetes patients with common renal and cardiovascular risk factors." Therapeutic Advances in Endocrinology and Metabolism, 2013, vol. 4, No. 3, pp. 95-105.
Gallwitz, linagliptin-A novel Dipeptidyl Peptidase Inhibitor for Type 2 Diabetes Therapy, Clinical Medicine Indights: Endocrinology and Diabetes, 2012, vol. 5, p. 1-11.
Galvus (Vildagliptin) Scientific Discussion, EMEA, 2007, pp. 1-34.
Garber, A. J. et al., "Effects of Vildagliptin on Glucose Control in Patients with Type 2 Diabetes Inadequately Controlled with a Sulphonylurea". Diabetes, Obesity and Metabolism (2008) vol. 10 pp. 1047-1055.
Garber, A.J. et al., "Simultaneous glyburide/metformin therapy is superior to component monotherapy as an initial pharmacological treatment for type 2 diabetes." Diabetes, Obesity and Metabolism, 2002, vol. 4, pp. 201-208.
Garber, A.J. et al., "Update: Vildaglitin for the treatment of Type 2 diabetes" Expert Opinion on Investigational Drugs, 200801GB, vol. 17, No. 1, Jan. 2008, p. 105-113.
Garcia-Soria, et al., "The dipeptidyl peptidase-4 inhibitor PHX1149 improves blood glucose control in patents with type 2 diabetes mellitus". Diabetes, Obesity and Metabolism, Apr. 2008, vol. 10, No. 4, p. 293-300.
Geka, 2001, vol. 67, No. 11, p. 1295-1299.
Gennaro, Alfonso R. Remington Farmacia, 2003, Spanish copy: p. 828, English copy: pp. 711-712, Preformulation, Chapter 38.
Gennaro, Alfonso R., Remington Farmacia, 19th Edition, Spanish copy, 1995, p. 2470.
Gennaro, Alfonso, R; Remington: The Science and Practice of Pharmacy: Oral Solid Dosage Forms; Mack Publishing Company, Philadelphia, PA (1995) vol. II, 19th Edition, Ch. 92 pp. 1615-1649.
Gennaro, Alfonso; Remington: The Science and Practice of Pharmacy, Twentieth Edition, 2000, Chapter 45, pp. 860-869.
Giron, D.; Thermal Analysis and Calorimetric Methods in the Characterisation of Polymorphs and Solvates; Thermochimica Acta (1995) vol. 248 pp. 1-59.
Glucophage® Prescribing Information, 2001.
Glucotrol XL (glipizide), package insert, Pfizer, Apr. 1, 2002.
Goldstein, L.A., et al., "Molecular cloning of seprase: a serine integral membrane protease from human melanoma." Biochimica et Biophysica Acta, vol. 1361, 1997, No. 1, pp. 11-19.
Gomez-Perez, et al., "Insulin Therapy:current alternatives", Arch. Med. Res. 36: p. 258-272 (2005).
Goodarzi, M.O. et al., "Metformin revisited: re-evaluation of its properties and role in the pharmacopoeia of modern antidiabetic agents." Diabetes, Obesity and Metabolism, 2005, vol. 7, pp. 654-665.
Graefe-Mody, et al; Evaluation of the Potential for Steady-State Pharmacokinetic and Phamacodynamic Interactions Between the DPP-4 Inhibitor Linagliptin and Metformin in Healthy Subjects; Currents Medical Research and Opinion (2009) vol. 25, No. 8 pp. 1963-1972.
Graefe-Mody, U. et al., "Effect of Renal Impairment on the Pharmacokinetics of the Dipeptidyl Peptidase-4 Inhibitor Linagliptin." Diabetes, Obseity and Metabolism, 2011, pp. 939-946.
Greene, T.W, et al., "Protection for the Amino Group". Protective Groups in Organic Synthesis, 3rd edition, 1999, p. 494-653.
Greischel, et al., Drug Metabolism and Deposition, "The Dipeptidyl Peptidase-4 Inhibitor Linagliptin Exhibits Time- and Dpse-Dependent Localization in Kidney, Liver, and Intestine after Intravenous Dosing: Results from High Resolution Autoradiography in Rats", 2010, vol. 38, No. 9, p. 1443-1448.
Groop, Effects of The DPP-4inhibitor linagliptin on albuminuria in patients with type 2 diabetes, www.abstractsonline.com, 2013, 1 page.
Guglielmi, C. et al., "Latent autoimmune diabetes in the adults (LADA) in Asia: from pathogenesis and epidemiology to therapy." Diabetes/Metabolism Research and Reviews, 2012, vol. 28, Supplement 2, pp. 40-46.
Gupta, V. et al., "Choosing a Gliptin." Indian Journal of Endocrinology and Metabolism, 2011, vol. 15, No. 4, pp. 298-308.

(56) References Cited

OTHER PUBLICATIONS

Gwaltney, S. "Medicinal Chemistry Approaches to the Inhibition of Dipeptidyl Peptidase IV", Current Topics in Medicinal Chemistry, 2008, 8, p. 1545-1552.
Gwaltney, S.L. II et al., "Inhibitors of Dipeptidyl Peptidase 4." Annual Reports In Medicinal Chemistry, 2005, vol. 40, pp. 149-165.
Jibiinkoka-Tenbo, Vision of Otorhinolaryngology, How to use antimicrobial drug in a patient with impairment of renal function, vol. 44, No. 3, 2001, p. 217-220.
Johansen, Cardiovascular safety with linagliptin on patients with type 2 diabetes mellitus, Cardiovascular Diabetology, 2012, vol. 11, p. 1-10.
Johansen, O. E. et al., "Cardiovascular safety with linagliptin in patients with type 2 diabetes mellitus: a pre-specified, prospective, and adjudicated meta-analysis of a phase 3 programme." Cardiovascular Diabetology, Biomed Central, 2012, vol. 11, No. 3, pp. 1-10.
Johansen, O.E. et al., "b-cell Function in Latnet Autoimmune Diabetes in Adults (LADA) Treated with Linagliptin Versus Glimepiride: Exploratory Results from a Two Year Double-Blind, Randomized, Controlled Study." www.abstractsonline.com, Jun. 10, 2012, XP-002708003.
John Hopkins Children's Center, "Liver Disorders and Diseases." Retrieved online May 26, 2014 <http://www.hopkinschildrens.org/non-alcoholic-fatty-liver-disease.aspx>.
Jones, R.M. et al., "GPR119 agonists for the treatment of type 2 diabetes". Expert Opinion on Therapeutic Patents 2009 Informa Healthcare for GBR LNKSD—DOI: 10.1517/13543770903153878, vol. 19, No. 10, Oct. 2009, p. 1339-1359.
Kanada, S. et al., "Safety, tolerability, pharmacokenetics and pharmacodynamics of multiple doses of BI 1356 (proposed tradename Ondero), a dipeptidyl peptidase 4 inhibitor, in Japanese patients with type 2 diabetes" Diabetes, vol. 57, No. Suppl. 1, Jun. 2008, p. A158-A159 and 68th Annual Meeting of the American Diabetes Association: San Francisco, CA, Jun. 6-10, 2008.
Karaliede et al., Diabetes Care, Endothelial Factors and Diabetic Nephropathy, 2011, 34, Suppl 2, p. 291-296.
Kaur, Development of new incretin drugs: Promising Therapies, Indian Journal Pharmacology, 2006, vol. 38, Issue 2, p. 100-106.
Kawamori, Linagliptin monotherapy provides superior glycaemic control v. placebo or voglibose with comparable safety in Japanese patients with type 2 diabetes, a randomized , placebo and active comparator -controlled doiuble blind study, 2011, Diabetes, Obesity and Metabolism, p. 348-357.
Kelly. T., "Fibroblast activation protein-cx and dipeptidyl peptidase IV (CD26)P: Cell-surface proteases that activate cell signaling and are potential targets for cancer therapy". Drug Resistance Update 8, 2005, vol. 8. No. 1-2, pp. 51-58.
Kendall, D. M. et al., "Incretin Mimetics and Dipeptidyl Peptidase-IV Inhibitors: A Review of Emerging Therapies for Type 2 Diabetes." Diabetes Technology & Therapeutics, 2006, vol. 8, No. 3, pp. 385-398.
Kharkevich, D. A., "Educational Literature" Pharmacology (1987) Third Edition, Meditsina Press, Moscow pp. 47-48.
Kibbe, A., Editor. Handbook of Pharmaceutical Excipients, Third Edition, Copovidon-pp. 196-197, Date of Revision: Dec. 16, 2008. Mannitol-pp. 424-425, Date of Revision: Feb. 19, 2009, Published in 2009.
Kidney Disease (Nephropathy), Retrieved online May 13, 2013. www.diabetes.org/living-with-diabetes/complications/kidney-disease-nephropathy.html <http://www.diabetes.org/living-with-diabetes/complications/kidney-disease-nephropathy.html>.
Kim, Comparison of DPP-4 Inhibitors, The Journal of Korean Diabetes, http:dx.doi.org/10.4093/jkd.2013.14.3.111. 6 pages.
Kim, D. et al., "(2R)-4-Oxo-4-(3-(Trifluoremethyl)-5,6-dihydro[1,2,4]triazolo[4,3-a]pyrazin-7(8H)-yl-1-(2,4,5-trifluorophenyl)butan-2-amine: A Potent, Orally Active Dipeptidyl Peptidase IV inhibitor for the Treatment of Type 2 Diabetes." Journal Med. Chem, 2005, 48, p. 141-151.
Kim, Kwang-Rok et al., "KR-62436, 6-{2-{2-(5-cyano4,5-dihydropyrazol-1-yl)-2-oxoethylamino}ethylamino} nicotinonitrile, is a novel dipeptidyl peptidase-IV (DDP-IV inhibitor with anti-hyperglycemic activity" European Journal of Pharmacology 518, 2005, p. 63-70.
Kiraly, K. et al., "The dipeptidyl peptidase IV (CD26, EC 3.4.14.5) inhibitor vildagliptin is a potent antihyperalgesic in rats by promoting endomorphin-2 generation in the spinal cord." European Journal of Pharmacology, 2011, vol. 650, pp. 195-199.
Kirpichnikov, D. et al., "Metformin: An Update." Annals of Internal Medicine, 2002, vol. 137, No. 1, pp. 25-33.
Kishore, Preeti MD., "Complications of Diabetes Mellitus." Merck Manual Consumer Version, 2016, pp. 1-7.
Kleeman, Pharmaceutical Substances, Synthesesm Patents, Applications, p. 1196-1997, 1999.
Klein, T. et al., "Linagliptin alleviates hepatic steatosis and inflammation in a mouse model of non-alcoholic steatohepatitis." Medical Molecular Morphology, 2014, vol. 47, pp. 137-149.
Knorr, M. et al., "Comparison of Direct and Indirect Antioxidant Effects of Linagliptin (BI 1356, Ondero) with other Gliptins— Evidence for Anti-Inflammatory Properties of Linagliptin". Free Radical Biology and medicine, Elsevier Science, U.S. vol. 49, Oct. 23, 2010, p. S197.
Knowler, W.C. et al., "Reduction in the Incidence of Type 2 Diabetes with Lifestyle Intervention or Metformin." The New England Journal of Medicine, 2002, vol. 346, No. 6, pp. 393-403.
Komori, Kiyoshi., "Treatment of Diabetes in Patients for Whom Metforming Treatment is Not Appropriate" Modern Physician (2008) vol. 28, No. 2 pp. 163-165.
Konstantinou, D. M. et al., "Pathophysiology-based novel pharmacotherapy for heart failure with preserved ejection fraction." Pharmacology & Therapeutics, 2013, vol. 140, No. 2, pp. 156-166.
Korom, S. et al; Inhibition of CD26/dipeptidyl peptidase IV activity in vivo prolongs cardiac allograft survival in rat recipients 1,2, Transplantation, May 27, 1997, vol. 63, No. 10, pp. 1495-1500.
Kroller-Schön, S. et al., "Glucose-independent Improvement of Vascular Dysfunction in Experimental Sepsis by Dipeptidyl Peptidase-4 Inhibition." Cardiovascular Research, 2012, vol. 96, No. 1, pp. 140-149.
Kumar, V. et al., "Maillard Reaction and Drug Stability." Maillard Reactions in Chemistry, Food, and Health, 1994, No. 151, pp. 20-27.
Kuno, Y. et al., "Effect of the type of lubricant on the characteristics of orally disintegrating tablets manufactured using the phase transition of sugar alcohol." European Journal of Pharmaceutics and Biopharmaceutics, 2008, vol. 69, pp. 986-992.
Kurozumi, Efficacy of a-glucosidase inhibitors combined with dipeptylpeptidase-4 inhibitor for glucose fluctuation in patients with type 2 diabetes mellitus by continuous glucose monitoring, Journal of Diabetes Investigation, 2013, vol. 4, p. 393-398.
Lachman, L. et al., "The Theory and Practice of Industrial Pharmacy." Varghese Publishing House, Third Edition, 1987, pp. 190-194.
Lakatos, P. L. et al., "Elevated serum dipeptidyl peptidase IV (CD26, EC 3.4.14.5) activity in patients with primary biliary cirrhosis." Journal of Hepatol, 1999, vol. 30, p. 740.
Lakey, Technical Aspects of Islet Preparation, Translp, Int.m 2003, vol. 16, p. 613-632.
Lambier, A.M. et al., Dipeptidyl-Peptidase IV from Bench to Bedside: An Update on Structural Properties, Functions, and Clinical Aspects of the Enzyme DPP IV. Critical Reviews in Clinical Laboratory Sciences, 2003, 40(3), p. 209-294.
Lee Jones, K. et al., "Effect of Metformin in Pediatric Patients With Type 2 Diabetes." Diabetes Care, 2002, vol. 25, No. 1, pp. 89-94.
Leibovitz, E. et al., "Sitagliptin pretreatment in diabetes patients presenting with acute coronary syndrome: results from the Acute Coronary Syndrome Israeli Survey (ACSIS)." Cardiovascular Diabetology, 2013, vol. 12, No. 1, pp. 1-7.
Levien, T.L. et al., "New drugs in development for the treatment of diabetes", Diabetes Spectrum, American Diabetes Association, US, vol. 22, No. 2, Jan. 1, 2009, pp. 92-106.
Lieberman, H. et al., "Pharmaceutical Dosage Forms." Marcel Dekker, Inc., 1980, vol. 1, p. 38.

(56) References Cited

OTHER PUBLICATIONS

Lim, S. et al., "Effect of a Dipeptidyl Peptidase-IV Inhibitor, Des-Fluoro-Sitagliptin, on Neointimal Formation after Balloon Injury in Rats." Plos One, 2012, vol. 7, No. 4, pp. 1-11.
Linagliptin Monograph, Published by VACO PBM-SHG US Veteran's Administration, 2011, pp. 1-17.
Lindsay, J.R. et al., "Inhibition of dipeptidyl peptidase IV activity by oral metformin in Type 2 diabetes." Diabetic Medicine, 2005, vol. 22, pp. 654-657.
Lovshin, J.A. et al., "Incretin-based therapies for type 2 diabetes mellitus." Nature Reviews Endocrinology, 2009, vol. 5, pp. 262-269.
Luo, Theory and Practice of Modern Physical Pharmacy, Shangai Scientific And Technical Literature Publishing House, 2005, p. 294.
Lyssenko, V. et al., "Mechanisms by which common variants in the TCF7L2 gene increase risk of type 2 diabetes." The Journal of Clinical Investigation, 2007, vol. 117, No. 8, pp. 2155-2163.
March, J. "Advanced Organic Chemistry: Reactions, Mechanisms, and Structure". Fourth Edition, 1992, pp. 652-653.
Mathieu, C. et al., "Antihyperglycaemic therapy in elderly patients with type 2 diabetes: potential tole of incretin mimetics and DPP-4 inhibitors." International Journal of Clinical Practice, 2007, vol. 61, Suppl. 154, pp. 29-37.
Matsumiya, Teruhiko, et al., "Therapeutic Drugs for Clinicians" Diagnosis and Treatment (2008) vol. 96, No. 2 pp. 389-390.
Matsuyama, Glucagen like peptide: a ptotent glucagonostatic hormone, Diabetes Research, 1988, p. 281-288.
Yasuda, et al. "E3024 3-but-2-ynyl-5-methyl-2-piperazin-1-yl-3,5-dihydro-4H-imidazol [ 4,5-d]pyridazin-4-one tosylate, is a move, selective and competitive dipeptidyl peptidase-IV inhibitor". European Journal of Pharmacology, vol. 548, No. 1-3, Oct. 24, 2006, p. 181-187. Abstract.
Yasuda, N. et al., "Metformin Causes Reduction of Food Intake and Body Weight Gain and Improvement of Glucose Intolerance in Combination with Dipeptidyl Peptidase IV Inhibitor in Zucker fa/fa Rats." The Journal of Pharmacology and Experimental Therapeutics, 2004, vol. 310, No. 2, pp. 614-619.
Yokoyama< "Prevalence of albumineria and renal insufficiency and associated clinical factors in type 2 diabetes: the Japan Diabetes clinical data Management study(JDDM15)" Nephrol Dial Transplant (2009) 24: 1212-1219 Advance Access Pub 2008.
Yoshikawa, Seiji et al: Chemical Abstract of Japanese Patent No. WO 2003/104229 Preparation of purinone derivatives as dipeptidylpeptidase IV (DPP-IV) inhibitors, 2003.
Yoshioka, S. et al., "Stability of Drugs and Dosage Forms." Kluwer Academic Publishers, 2002, pp. 30-33.
Youssef, S. et al., "Purines XIV. Reactivity of 8-Promo-3,9-dimethylxanthine Towards Some Nucleophilic Reagents." Journal of Heterocyclic Chemistry, 1998, vol. 35, pp. 949-954.
Zaman, Comparison Between Effect of Vildagliptin and Linagliptin on Glycaemic control, renal function, liver funstion and lipid profile in patients of T2DM Inadequately controlled with combo of Metformin and Glimepiride, Journal of Dental and Medical Sciences, vol. 16, Issue 9, 2017. p. 27-31.
Zander, M. et al., "Additive Glucose-Lowering Effects of Glucagon-Like Peptide-1 and Metformin in Type 2 Diabetes." Diabetes Care, 2001, vol. 24, No. 4, pp. 720-725.
Zeeuw, D. et al., "Albuminuria, a Therapeutic Target for Cardiovascular Protection in Type 2 Diabetic Patients With Nephropathy." Circulation, 2004, vol. 110, No. 8, pp. 921-927.
Zejc, Alfred, et al; "Badania Nad Piperazynowymi Pochodnymi Dwumetyloksantyn" Acta Polon Pharm, XXXV (1976) Nr. 4 pp. 417-421.
Zeng, "Efficacy and Safety of linagliptin added to metformin and sulphonylurea in Chinese patients with type 2 diabetes: a subanalysis of data from a randomised clinical trial", Current Medical Research and Opinion, 2013, 8 pages.
Zerilli, T. et al., "Sitagliptin Phosphate: A DPP-4 Inhibitor for the Treatment of Type 2 Diabetes Mellitus." Clinical Therapeutics, 2007, vol. 29, No. 12, pp. 2614-2634.

Zhang, Classification and Treatment Prinicples of Diabetes, Beijing Medical Univ and China Union Medical Univ. Joint Publishing House. 1st ed., 1998, p. 939.
Zhimei, Xiao et al., "Study progression of oral drugs for treatment of type II diabetes." Drug Evaluation, 2004, vol. 1, No. 2, pp. 138-143.
Zhong, Qing et al; "Glucose-dependent insulinotropic peptide stimulates proliferation and TGF-? release from MG-63 cells," Peptides 24 (2003) 611-616.
Zhu, G. et al., "Stabilization of Proteins Encapsulated in Cylindrical Poly(lactide-co-glycolide) Implants: Mechanism of Stabilization by Basic Additives." Pharmaceutical Research, 2000, vol. 17, No. 3, pp. 351-357.
Zimdahl, H. et al., "Influence of TCF7L2 gene variants on the therapeutic response to the dipeptidylpeptidase-4 inhibitor linagliptin." Diabetologia, 2014, vol. 57, pp. 1869-1875.
Zimmer et al; Synthesis of 8-Substituted Xanthines and their Oxidative Skeleton Rearrangement to 1-Oxo-2,4,7,9-tetraazaspiro[4,5]dec-2-ene-6,8,10-triones; Euripean Journal Organic Chemistry (1999) vol. 9 pp. 2419-2428.
Drug Data Report, 1994, Source, Smith Kline Beechman, Treatments for Septic Shock, p. 459.
Horie, Biomedcentral, Design, statistical analysis and sample size calculation of a phase IIb/III study of linagliptin vs. voglibose and placebo, 2009.
International Search report for PCT/EP2019/069126, mailed Oct. 2, 2019.
Press, Synthesis of 5,6 Dimethoxyquinazolin-2(1-H) ones, J. Heterocyclic Chwm, 1986.
Adams, Pub Pharmafile, 2011, Boehringer-lilly launch diabetes drug tradjenta in US.
Excerpt from Orange Book of Product Tradjenta, Feb. 5, 2011.
Publication Boehringer Ingelheim and Lilly's New type 2 Diabetes Treatment tradjenta, 2015, p. 1-7.
Smithies, The Jackson Lab, Mouse Strain Datasheet, 2019, p. 1-2.
Who drug information, International nonproprietary Names for Pharmaceutical Substances, vol. 23, 2009, 1 page.
Pradham, Wound-healing abnormalities in Diabetes, Dept. of surgertm Harvard, Touch Briefings, 2007.
Basi, Diabetes Care, vol. 31, 2008, 1 page.
Sampanis, Hippokratia, Management of Hyperglcemia in patients with diabetes mellitus and chronic renal failure, vol. 12, p. 22-27, 2008.
US Court of Appeals for the Federal Circuit, *Boehringer Ingelheim Pharmaceuticals, Inc.* v. *Mylan Pharmaceuticals, Inc.*, Decided Mar. 16, 2020, retrieved online http;///www.cafc.uscourts.gov/sites/default/files/opinions-orders/19-1172.Opinion.3-16-2020_1551193.pdf (last visited May 29, 2020.)
Ahren, Vascular Health and Risk Management, Novel combination treatment of type 2 diabetes DPP-4 inhibition plus metformin, 2008, p. 383-394.
Linagliptin, Pub Chem, Clinical Trial Search of Japan, https://pubchem.ncbi.nlm.nih.gov/compound/10096344 dated Jun. 25, 2020.
Aschner, Emerging Treatments and Technologies, Effect of the Dipetttidyl Peptidase-4 Inhibitor Sitagliptin as Monotherapy on Glycemic Control in Patients with Type 2 Diabetes, vol. 29, 2006.
Huettner, Diabetes, Novel and Selective Xanthine, Jun. 2007 Supplement vol. 56,.
Heizmann, Xanthines as scaffold for molecular diversity, Molecular diversity, vol. 2, 1996, p. 171-174.
Hanrinwon, Pharmaceutical Subcommittee, Pharmaceutics, p. 284-288, 1995.
Schafer, Impaired glucagen like peptide 1 induced insulin secretions in carriers of transcription, Diabetologica, vol. 50, 2007.
Encyclopedia of Pharma Technology, Swarbrick, 3rd Ed., vol. 1, Absorption of Solid Surfaces, 2007.
Clinical Trials, NCT006002472, Bi 1356 In combination with Metformin submitted Feb. 27, 2014.
Boehringer Ingelheim Press Release: Boehringer Ingelheim's diabetes Pipeline continues to advance as the company announces conclusion of robust Phase III pivotal trials programme for linalgiptin, Small Molecules, Published Sep. 28, 2009, 2 pages.
Nationale Versorgungs-Leitlinie, Diabetes Mellitus, 2004.

(56) References Cited

OTHER PUBLICATIONS

Kibbe, Handbook of Pharmaceutical Excipients, 3rd Edition, 2009, p. 104-107.
Sung, Study on the preparation of tablets by direct compression method, Kisti, 2006.
Wade, Organic Chem, 6th Edition, 2006, p. 918, 943-956.
News Article, https:/www.in-phamratechnologist.com-Article-France-and-maerck-say-reformulated-Euthyrox-is-safe.)-Sep. 17, 2017, 1 page.
Brosius, Mouse Models of Diabetic Neuropathy, JASN, vol. 20, 2009, 5 pages.
Schmeider, Telmisartan in incipient and overt renal disease, J. Nephrol, vol. 24, 2011, 10 pages.
Stedman's Medical Dictionary, 27th edition, Def. of nephropathy, 1999, 1 page.
Clarivate Analytics on STN: Confirmation of the public accessibility of Schmeider before May 31, 2011.
Anonymous, New England Journal of Medicine, The effect of intensive treatment of diabetes on the development and progession of long term complicationsin insulin dependent mellitus, vol. 329, 1993.
Hanrimwon, Pharmaceutics Subcommitee, 2000, p. 321-322.
Eckhardt, 8-(3-(R)-Aminopiperidin-1-yl)-7-but-2-ynyl--3-methyl-1-(4-methyl-quinazolin-2-ylmethyl)-3,7-dihydropurine-2,6-dione (BO1356), Journal of Medicinal Chem., vol. 50, 2007, p. 6450-5453.
Rabinovitch, Thyophylline protects against diabetes in BB rats, Diabetologica, vol. 33, 1990.
International Search Report for PCT/EP2019/069131 mailed Oct. 8, 2019.
Clinical Trials.gov, for BI1356 for Patients in Combination wtih Metormin in Patients with Type 2 Diabetes.2014.
Bell, Diabetes Care, The frequent, forgotten, and and often fatal complication of diabetes, vol. 26, 2003, 9 pages.
International Search Report for PCT/EP2019/EP069131 mailed Jan. 28, 2021.
Isoda, Certificate of experimental Results, Analytical Research Development, 2021.
Luo, Shanghai Scientific and Technical Lit Publishing House, Theory and Practice of Modern Physical Pharmacy, vol. 4, 2005, p. 294.
Forst, ADA, Novel, Potent, Selective, DPP-4 inhibitor BI 1356 Significantly lowers HbA1c after only 4 weeks of treatment, 2007.
Park, Stability evalustion test for linagliptin formulation , CKD formuation lab, 2018.
The 4th Edition, Experimental Chem., Course 1, Society of Japan, 1990, p. 184-186.
Snyder, Use of Insulin and Oral hypoglycemic medication in patients with diabetes mellitus and advanced kidney disease, Diabetic Medication in Kidney Disease, Seminars in Dialysis, vol. 17, 2004, p. 365-370.
Xie, Hypoglycemic Drugs, New Practical Pharmacy, 2007, p. 832-934.
Akiyama, Sulphostin, a potent Inhibitor for dipeptiyl peptidase IV, The Journal of Antibiotics, vol. 54, No. 9, 2001, p. 744-746.
Artunc, Expert opinion relating to Euro patent Ep2640371, May 11, 2022, 5 pages.
Wong, Endothelial Dysfunction, J. Cardiovasc Pharmacol, vol. 55, 2010, 8 pages.
Groop, Linagliptin and its effects on hyperglycemia, Diabetes and obes Metab vol. 10, 2017, 10 pages.
Wang, A modest decease in endothelial NOS in mice, PNAS vol. 108, 2011, 7 pages.
Du, Hyperglycemia inhibits endothelial nitric oxide synthase oxide activity, JCI, vol. 108, 2001, 9 pages.
Craven, Impaired nitric oxide release by glomeruli from diabetic rats, Metabolism, vol. 44, 1995, 4 pages.
Excerpts of Diabetologie in Klinik and Praxis, 5th Edition, 2003, pp. 384 and 434.

Nippon Boehringer Ingelheim Co., Ltd., Press Release, Linagliptin Showing improvement in Albuminuria, Jun. 18, 2012.
Japanese Society Of Nephrology, Clinical Practice Guidebook, 2012, 145 pages.
Lee, Common foot diseases that primary care physicians should know about, Korean Journal of Family Medicine, vol. 26, 2005, p. 127-137.
Product information for Digosin Tab, CJ Health Care, 2014, 1 page.
Nationale Versorgungs-Leitlinie, Diabetes Mellitus, 2004., 15 pages.
Rosenstock, Effect of linagliptin v. placebo, JAMA, vol. 321, 2018, 11 pages.
Rosenstock, Cardiovascular safety of linagliptin in type 2 diabetes, Cardiovascular Diabetology, vol. 14, 2015, 15 pages.
The 13th Ed., Manual of Japanese Pharmacopoeia, 1996, 6 pages.
Pschryrembe, Clinical Dictionary, excerpt of Diabetes Mellitus, 2013, 2 pages.
Lee, Radical Approach to Diabetic Neuropathy, Kidney International, vol. 72, 2007, p. 67-70.
Rungby, inhibition of dipeptidyl peptidase 4 by BI 1356, a new drug for the treatment of beta cell failure in type 2 diabetes, Expert Opin. Invest. Drugs, vol. 18, 2009, p. 835-838.
Kendall, Emerging Treatments in Diabetes Care, Effects of Exenatide on Glycemic Control over 30 weeks in Patients with Type 2 Diabetes, vol. 28, 2005, 9 pages.
Donnelly, BMJ, Vascular complications of diabetes, 2000, 5 pages.
American Diabetes Assoc., Diagnosis and Classification of Diabetes Mellitus, vol. 29, 2006, 6 pages.
Dittberner, S. et al., "Determination of the absolute bioavailability of BI 1356, a substance with non-linear pharmacokinetics, using a population pharmacokinetic modeling approach." Abstracts of the Annual Meeting of the Population Approach Group in Europe, 2007, 1 page.
Vickers, 71st Scientific Session of the American Diabetes Association, "The DPP-4 inhibitor linagliptin is weight neutral in the DIO rat but inhibits the weight gain of DIO animals withdrawn from exenatide", vol. 60, Jul. 2011, 1 page.
Ferreira, Triple Combination therapy with sitagliptin, metformin and rosiglitazone improves glycaemic control in patiens with type 2 diabetes, Diabetologixa, 2008, Suppl 1., 2 pages.
Glucophage (metformin hydrocholoride tablets) revised label, 2003, 1 page.
Pink Sheet Daily, Boehringer/Lilly's Linagliptin Approved, 2011 1 page.
Makino, Decreased CirculatingCD-34 cells, Diabetic Medicine, 2009, 3 pages.
Cade, Diabetes Related Microvascular Diseases in the Physical Therapy Setting, Journal of the American Physical Therapy Assoc., 2008, 16 pages.
Byrn, Pharmaceutical Solids, A Strategic Approach to Regulatory Considerations, Pharmaceutical Research, 1995, vol. 12, 10 pages.
Herman, The DP-IV inhibitor MK-0431 enhances active GLP-1 and reduces Glucose following an OGTT in Type 2 Diabetics, American Diabetes Asociation, 2004, 1 page.
Abdoh, Amlodipine Besylate-Excipients Interaction in Solid Dosage Form, Phamra Dev. and Strategy, 2018, 15-24.
Fuchs, Journal of Pharmacy and Pharmacology, Concentration-dependent plasma protein binding of the novel dipeptidyl peptidase 4 inhibitor BI 1356 due to saturable binding to its target in plasma of mice, rats and humans, 2009, 8 pages.
Fowler, Microvascular and Macrovascular Complications of Diabetes, Diabetes Foundation, vol. 26, 2008, 6 pages.
Florez, Genetic Susteptibility to Type 2 Diabetes, J. of Diabetes, vol. 3, 2009, 7 pages.
The Japan Diabetes Society, Guidelines for treatment of Diabetes, Feb. 14, 2006, p. 21-33, 41-55, 62-76.
Yamaguchi, Today's Therapeutic Guidelines, 2006, p. 518-520.
Sakura, Trends in development on oral diabetic agents and new developments of treatment, Clinical Endocrinology, vol. 3, 2011, p. 51-55.
Yoshimoto, Structure of DPP-4 and Antidiabetic Therapeutic Agents, Current Diabetology, vol. 3, p. 51-55.
Kawamori, Investigation of Diabetes, Soten Lmtd., 2004, p. 15-19.
Shigeta, MR Training Manual, Elsevier, 2004, p. 44-54, p. 67-74.

(56) References Cited

OTHER PUBLICATIONS

Ono, Diabetes and islet tranplantation, Japanese J. of clinical Pathology, vol. 54, 2006, p. 379-385.
Suzuki, Prospects of ISlet transplantation, Pharma medica, vol. 24, 2006, p. 67-71.
Shimada, MR Training Manual, Cardiovascular System, Elsevier, 2003, p. 2-58.
Kazunaga, Guidelines for Required dose Response, Pharmaceutical Examination, 1994, 1 page.
Ministry of Health, Clinical Pharmacokinetics Examination of Druge, vol. 796, 2001, 1 page.
Uematsu, Text of clinical Pharmacology, Nancodo, 1997, p. 45-51.
National Library of Medicine, Searching result of information for Clinical Trial NCT00309608 for Linagliptin from Clinicaltrials.gov, Mar. 31, 2006.
Boehringer Ingelheim Japan, Interview Form for Trazenta Tablets 5 mg, Apr. 2022, 18 version.
Katakami, Action and usage of oral hypoglycemic agents, Clinica, vol. 31, 2004, p. 398-399.
Sanwa Kagaku Kenkyusho, Package Insert fo Seibule tablets 25mg, 50 mg, 75mg, Aug. 2021.
Funabashi, Basic concept for metabolic syndrome, Pharma medica, vol. 22, 2004, p. 11-16, 21-24.
Kita, Satin based anti-arteriosclerotic drugs, vol. 32, 2000, p. 932-936.
Viatris Pharmaceuticals, Package Insert for Lipitor, 10mg. Nov. 2022.
Sun Pharma Japan Limited, Package insert for Lopresor Tablet, 20mg, 40mg, Oct. 2021.
Sumitomo Pharma Co., Package insert for AmlodinTablets, 2.5mg, 5mg, 10mg, and Amlodin MD Tablets, 2.5mg, 5mg, 10mg, Dec. 2022.
Pfizer Lab Division, Inc., Drug Label for Altace Ramipril Casules, Feb. 2022.
Novartis Pharma, K.K. Package Insert for Diovan Tablets, 20mg, 40mg, 80mg, 16omg, Apr. 2020.
Boehringer Ingelheim Japan, Package insert for Micardis Tablets, 20mg, 40mg, 80mg, Jul. 2020.
Viatros Pharmaceuticals, Co., Ltd., Interview form for Lipitor Tablets, 5mg, 10mg, Dec. 2022.
Hotchkiss, The pathophysiology and Treatment of Sepsis, The New England J. of Medicine, vol. 348, 2003, 13 pages.
Russell, Treatment of Sepsis, New England J. of Medicine, vol. 355, 2006, 15 pages.
Dedov, Russian Federation Ministry of Health, Sugar Glabetes, 8th edition, vol. 20, 2017, 22 pages.
Graefe-Mody, The novel DPP-4 inhibitor BI 1356 (proposed tradename Ondero) and metformin can be safely co-administered, Abstract, Diabetes, online, 2008, retrieved from internet, URL: http://professional.diabetes.org/Content/posters/2008/p553-P.pdf>retrieved on Dec. 21, 2009.
Wang, BI-1356, dipeptyl-peptidase IV inhibitor, antidiabetic agent, Drugs of the future, Prous science, vol. 33, No. 6, 2008, p. 473-477.
Pei, From the bench to the bedside, dipeptidyl peptidase IV inhibitors, a new class of oral antihyperglycemic agents, Current Opinion in drug discovery and development, vol. 11, 2008, p. 512-532.
Nathan, Management of hypoglycemia in type 2 diabetes, Diabetes care, vol. 29, 2006, 10 pages.
Ristic, Improved glycemic contol with dipeptyl peptidase 4 inhibitionin patients with type 2 diabetes, Diabetes, Obesity and metabolism, vol. 7, 2005, 8 pages.
Maedler, Sulfonylurea Induced b-cell Apoptosis in Clutured Human islets, The j. of CLinical Endocrinology & Metabolism, vol. 1, 2005, 6 pages.
Kendall, Effects of Exenatide on Glycemic control over 30 weeks in patients with type 2 diabetes treated with metformin and a Sulfonylurea, Diabetes Care, vol. 28, 2005, 9 pages.
Meneilly, Diabetes in Elderly adults, J. of Gerontology, vol. 56A, 2001, 9 pages.
Herrington, Metformin: effective and safe in renal disease?, Int. Urol. Nephrol., vol. 10, 2008, 7 pages.
Ashford, Bioavailability-physiochemical and dosage form factors, Aulton's Pharmaceutics, 3rd Edition, 2007, p. 286-289.
Yu, Evalution of USP Apparatus 3 Dissolution Testing of Immediate Release Products, AAPS PharmScience, vol. 4, Issue 1, 2002, p. 1-5.
Mueller, Eugen Excerpt on biguanides, Methoden der Organisichen Chemie, 1952, p. 215-2019.
Bailey, fixed dose single table anti-diabetic combinations, Diabetes, Obesity and metabolism, vol. 11, 2009, p. 527-533.
Merck & Co, Januet Leaflet, 2008, Evidence of date of Disclosure, p. 1-24.
Supplementary Appendix of Gallwitz, Lancet, vol. 380, published online Jun. 28, 2012, p. 475-483.
Dedova, Alogorithims of Specialized Medical care for diabetes, 8th edition, Sugar Glabetes, vol. 1S, 2017, 31 pages.
Groop, linagliptin lowers albuminaria on top of recommended standard treatment for diabetic nephropathy, Annual meeting Science Session American Diabetes Assoc., Jun. 6, 2012, Abstract, 1 page.
Wingard, Heart Disease and Diabetes, Diabetes in America, Chapter 19, 1995, p. 429-448.
Greer, Myocardial infarction and heart failure in the db/db diabetic mouse, Amer. J. Physio. Heart Circ. Physiol., vol. 290, 2006, p. H146-H153.
King, Microvascular and Macrovascular Complications of Diabetes, Amer. J. of Diabetes Complications, vol. 69, 2005, Article 87.
Japan Council for Quality Health Care, Guidlines for Treatment Chronic Heart Failure, https://minds.jcqhc.or.jp/n/med//4/me00/49/G0000132/0003 edited 2005.
International Search Report and Written Opinion for PCT/EP2009/067772 mailed Apr. 14, 2010.
International Search Report and Written Opinion for PCT/EP2010/050103 mailed Mar. 22, 2010.
International Search Report and Written Opinion for PCT/EP2010/051093 mailed Jul. 14, 2010.
International Search Report and Written Opinion for PCT/EP2010/051817 dated Jun. 8, 2010.
International Search Report and Written Opinion for PCT/EP2010/064691 mailed Apr. 6, 2011.
International Search Report and Written Opinion for PCT/EP2010068349 mailed Feb. 4, 2011.
International Search Report and Written Opinion for PCT/EP2011/054169 mailed Aug. 4, 2011.
International Search Report and Written Opinion for PCT/EP2011/057163 mailed Jun. 27, 2011.
International Search Report and Written Opinion for PCT/EP2011/057256 mailed Jul. 22, 2011.
International Search Report and Written Opinion for PCT/EP2011/060449 mailed Sep. 27, 2011.
International Search Report and Written Opinion for PCT/EP2011/070156 dated Jan. 17, 2012.
International Search Report and Written Opinion for PCT/EP2012/053910 mailed May 14, 2012.
International Search Report and Written Opinion for PCT/EP2012/063852 mailed Sep. 6, 2012.
International Search Report and Written Opinion for PCT/EP2012/077024 mailed Feb. 19, 2013.
International Search Report and Written Opinion for PCT/EP2013/054524 mailed on Apr. 24, 2013.
International Search Report and Written Opinion for PCT/EP2013/059828 mailed Aug. 6, 2013.
International Search Report and Written Opinion for PCT/EP2013/059831 mailed on Aug. 9, 2013.
International Search Report and Written Opinion for PCT/EP2013/060311 mailed Aug. 9, 2013.
International Search Report and Written Opinion for PCT/EP2013/060312 mailed on Sep. 4, 2013.
International Search Report and Written Opinion for PCT/EP2013/070978 mailed on Oct. 31, 2013.
International Search Report and Written Opinion for PCT/EP2014/055113 mailed May 16, 2014.

(56) References Cited

OTHER PUBLICATIONS

International Search Report and Written Opinion for PCT/EP2014/062398 mailed Aug. 20, 2014.
International Search Report and Written Opinion for PCT/EP2015/054114 mailed May 12, 2015.
International Search Report and Written Opinion for PCT/EP2015/074030 mailed Feb. 4, 2016.
International Search Report and Written Opinion for PCT/EP2017/064007, mailed Jun. 8, 2017.
International Search Report and Written Opinon for PCT/EP2007/054204 mailed Aug. 3, 2007.
International Search Report for PCT/EP03/12821 mailed Mar. 30, 2004.
International Search Report for PCT/EP03/13648 mailed Apr. 5, 2004.
International Search Report for PCT/EP2002/01820 mailed May 7, 2002.
International Search Report for PCT/EP2003/12821 mailed Mar. 30, 2004.
International Search Report for PCT/EP2003/13648 mailed Apr. 5, 2004.
International Search Report for PCT/EP2005/001427 mailed May 23, 2005.
International Search Report for PCT/EP2005/055711 dated Mar. 29, 2006.
International Search Report for PCT/EP2007/054204 mailed Mar. 8, 2007.
International Search Report for PCT/EP2007/058181 mailed Nov. 28, 2007.
International Search Report for PCT/EP2008/060738 mailed Nov. 5, 2008.
International Search Report for PCT/EP2009/060170 mailed Oct. 28, 2009.
International Search Report for PCT/EP2010/064691 mailed Jan. 20, 2011.
International Search Report for PCT/EP2013/060309 mailed Aug. 9, 2013.
International Search Report for PCT/EP2013/070979 mailed Nov. 26, 2013.
International Search Report for PCT/EP2014/060160 mailed Nov. 8, 2014.
Inukai, T., "Treatment of Diabetes in Patients for Whom Metformin Treatment is Not Appropriate." Modern Physician, 2008, vol. 28, No. 2, pp. 163-165.
Inzucchi, Silvio E., "Oral Antihyperglycemic Therapy for Type 2 Diabetes." The Journal of the American Medical Association, 2002, vol. 287, No. 3, pp. 360-372.
Isomaa, B. et al., "Cardiovascular Morbidity and Mortality Associated With the Metabolic Syndrome." Diabetes Care, 2001, vol. 24, No. 4, pp. 683-689.
Isomaa, Chronic Comlications in patients with slowly progressing atutoimmune type 1 diabetes, Diabetes Care, vol. 22, 1999, p. 1347-1353.
Iwamoto, Yasuhiko, "Insulin Glargine." Nippon Rinsho, 2002, vol. 60, Suppl. 9, pp. 503-515.
Janumet dosing instructions, Highlights of Prescribing information, 2008.
Janumet Prescribing Information, revised Jan. 2008.
Januvia Prescribing Information and Product Label, 2006.
Januvia, 25mg, 50mg, 100 mg, Summary of Product Characteristics, 2015, www.medicines.org.uk/EMC <http://www.medicines.org.uk/EMC>.
"Betahistine diHCL CF 16 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG, P3_RVG1:H,EN,57626>.
"Betahistine diHCL CF 8 mg, tabletten," Dutch Medicines Evaluation Board, Dated Apr. 13, 1988, Retrieved online from: <http://db.cbg-meb.nl/ords/f?p=111:3:0:SEARCH:NO::P0_DOMAIN,P0_LANG,P3_RVG1:H,EN,56227>.

"Sifrol 0,088 mg, tabletten," Dutch Medicines Evaluation Board, Dated Oct. 14, 1997, Retrieved online from: <http://db.cbg-meb.nl/ords/f?p=111:3:0:SEARCH:NO:P0_DOMAIN,P0_LANG,P3_RVG1:H,EN,70120>.
"Sifrol 0, 18 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70121>.
"Sifrol 0,35 mg, tabletten," Dutch Medicines Evaluation Board, Dated Nov. 16, 1999, Retrieved online from: <http://db.cbg-meb.nl/ords/f?p=111:3:0:SEARCH:NO::P0_DOMAIN,P0_LANG,P3_RVG1:H,EN,70673>.
"Sifrol 0,70 mg, tabletten," Dutch Medicines Evaluation Board, Dated Oct. 14, 1997, Retrieved online from: <http://db.cbg-meb.nl/ords/f?p=111:3:0:SEARCH:NO:P0_DOMAIN,P0_LANG,P3_RVG1:H,EN,70122>.
"Sifrol 1,1 mg, tabletten," Dutch Medicines Evaluation Board, Dated Oct. 14, 1997, Retrieved online from: <http://db.cbg-meb.nl/ords/f?p=111:3:0:SEARCH:NO::P0_DOMAIN,P0_LANG,P3_RVG1:H,EN,70124>.
Abstract for AU 2003280680, Jun. 18, 2004.
Abstract for AU 2009224546, Sep. 17, 2009.
Abstract in English for DE10109021, 2002.
Abstract in English for DE19705233, Aug. 13, 1998.
Abstract in English for DE2205815, 1972.
Abstract in English for EP0023032, 1981.
Abstract in English for JP 2002/348279, Dec. 4, 2002.
Abstract in English for JP 2003/286287, Oct. 10, 2003.
Abstract in English for KR20070111099, Nov. 11, 2007.
ACTOS Prescribing Information, 1999, pp. 1-26.
Adebowale, K.O. et al., "Modification and properties of African yam bean (*Sphenostylis stenocarpa* Hochst. Ex A. Rich.) Harms starch I: Heat moisture treatments and annealing." Food Hydrocolloids, 2009, vol. 23, No. 7, pp. 1947-1957.
Ahmed, Materials Formulation of Low Dose Medicines, Americal Pharma review, vol. 3, 2000, 1 page.
Ahren, B. et al., "Twelve- and 52-Week Efficacy of the Dipeptidyl Peptidase IV Inhibitor LAF237 in Metformin-Treated Patients With Type 2 Diabetes." Diabetes Care, 2004, vol. 27, No. 12, pp. 2874-2880.
Ahren, Bo "Novel combination treatment of type 2 diabetes DPP-4 inhibition + metformin." Vascular Health and Risk Management, 2008, vol. 4, No. 2, pp. 383-394.
Ahren, Bo, et al; Improved Meal-Related b-Cell Function and Insulin Sensitivity by the Dipeptidyl Peptidase-IV Inhibitor Vildagliptin in Metformin-Treated Patients with Type 2 Diabetes Over 1 Year; Diabetes Care (2005) vol. 28, No. 8 pp. 1936-1940.
Ahren, Bo; "DPP-4 inhibitors", Best practice and research in clinical endocrinology and metabolism—New therapies for diabetes 200712 GB LNKD—DOI:10.1016/J. Beem.2007.07.005, vol. 21, No. 4, Dec. 2007, pp. 517-533.
Al-Masri, I.M. et al., "Inhibition of dipeptidyl peptidase IV (DPP IV) is one of the mechanisms explaining the hypoglycemic effect of berberine." Journal of Enzyme Inhibition and Medicinal Chemistry, 2009, vol. 24, No. 5, pp. 1061-1066.
Alter, M. et al., "DPP-4 Inhibition on Top of Angiotensin Receptor Bockade Offers a New Therapeutic Approach for Diabetic Nephropathy." Kidney and Blood Pressue Research, 2012, vol. 36, No. 1, pp. 119-130.
American Association of Clinical Endocrinologists, "Medical Guidelines for Clinical Practice for the Management of Diabetes Mellitus." Endocrine Practice, 2007, col. 13, Suppl. 1, pp. 1-68.
American Diabetes Association, "Standards of Medical Care in Diabetes-2008." Diabetes Care, Jan. 2008, vol. 31, Supplement 1, pp. S12-S54.
Announcement of the approval of Novel oral Diabetes Drug Januvia, Press Release, 2006.
Anstee, Quentin M. et al. "Mouse models in non-alcholic fatty liver disease and steatohepatitis research" (2006) International Journal of Expermental Pathology, vol. 87, pp. 1-16.
Approval material for Tradjenta tablet, Trial 1218.2, Center for Drug Eval. and Research, 2011.

(56) References Cited

OTHER PUBLICATIONS

Aronow, Congestive Heart Failure, Treatment of Heart Failure in Older Persons with Coexisting Conditions, vol. 9, No. 3, 2003, p. 142-147.

Augeri, D.J. "Discovery and Preclinical Profile of Saxagliptin (GMB-477118): A Highly Potent, Long-Acting, Orally Active Dipeptidyl Peptidase IV Inhibitor for the Treatment of Type 2 Diabetes". Journal Med. Chem, 2005, vol. 48, No. 15, p. 5025-5037.

Augusti, D.V. et al., "Quantitative determination of the enantiomeric composition of thalidomide solutions by electrospray ionizatiotandem mass spectrometry". Chem Comm, 2002, p. 2242-2243.

Augustyns, K. et al., The Unique Properties of Dipeptidyl-peptidase IV (DPP IV/CD 26) and the Therapeutic Potential of DPP-IV Inhibitors, Current Medicinal Chemistry, vol. 6, No. 4, 1999, pp. 311-327.

Aulinger, B.A. et al., "Ex-4 and the DPP-IV Inhibitor Vildagliptin have Additive Effects to Suppress Food Intake in Rodents". Abstract No. 1545-P. 2008.

Aulton, Michael E., Pharmaceutics: The Science of Dosage Form Design, Second Edition, 2002, pp. 441-448.

Baetta, R. et al., "Pharmacology of Dipeptidyl Peptidase-4 Inhibitors." Drugs, 2011, vol. 71, No. 11, pp. 1441-1467.

Balaban, Y.H. et al., "Dipeptidyl peptidase IV (DDP IV) in NASH patients" Annals of Hepatology, vol. 6, No. 4, Oct. 1, 2007, pp. 242-250, abstract.

Balbach, S. et al., "Pharmaceutical evaluation of early development candidates the 100 mg-approach." International Journal of Pharmaceutics, 2004, vol. 275, pp. 1-12.

Balkan, B. et al., "Inhibition of dipeptidyl peptidase IV with NVP-DPP728 increases plasma GLP-1 (7-36 amide) concentrations and improves oral glucose tolerance in obses Zucker rates". Diabetologia, 1999, 42, p. 1324-1331.

Banker, Gilbert S., "Prodrugs." Modern Pharmaceutics Third Edition, Marcel Dekker, Inc., 1996, p. 596.

Barrara, Granulation, Handbook of Powder Technology, vol. 11, 2015, 2 pages.

Bastin, R.J. et al., "Salt Selection and Optimization Procedures for Pharmaceutical New Chemical Entities". Organic Process Research and Development, 2000, vol. 4, p. 427-435.

Beauglehole, Anthony R., "N3-Substituted Xanthines as Irreversible Adenosine Receptor Antagonists." Ph.D. Thesis, Deakin University, Australia, 2000, pp. 1-168.

Beljean-Leymarie et al., Hydrazines et hydrazones hétérocycliques. IV. Synthèses de dérivés de l'hydrazine dans la série des imidazo[4,5-d]pyridazinones-4, Can. J. Chem., vol. 61, No. 11, 1983, pp. 2563-2566.

Berge, S. et al., "Pharmaceutical Salts." Journal of Pharmaceutical Sciences, 1977, vol. 66, No. 1, pp. 1-19.

Bergmann, Decrease of serum dipeptidylpeptidase activity in severs sepsis patients, Clinica Chimica Acta 2002., p. 123-126.

Bernstein, Joel "Polymorphism in Molecular Crystals." Oxford University Press, 2002, p. 9.

Blech, S. et al., "The Metabolism and Disposition of the Oral Dipeptidyl Peptidase-4 Inhibitor, Linagliptin, in Humans", Drug Metabolism and Disposition, 2010, vol. 38, No. 4, p. 667-678.

*Boehringer Ingelheim Pharmceuticals, Inc. v. HEC Pharm Co., Ltd., et al.*, No. 15-cv-5982, United States District Court for the District of New Jersey, Dec. 8, 2016.

Mayo Clinic Staff: "Nonalchoholic fatty liver disease: Prevention" [retrieved on Nov. 30, 2012]. retrieved from the Internet: ,URL: http://www.mayoclinic.com/health/nonalcoholic-fatty-liver-disease/DS00577DSECTION=prevention>.

McNay, David E.G. et al., "High fat diet causes rebound weight gain." Molecular Metabolism, 2013, vol. 2, pp. 103-108.

Medicine Department of Pharmacy, Pharmaceutical Subcommitte, Book Publishing Harwinton, 1996, p. 283.

Medline Plus, "Obesity" 2013, Retrieved from internet on Aug. 22, 2013, http://www.nlm.nih.gov/medlineplus/obesity.html.

Meece, J. "When Oral Agents Fail: Optimizing Insulin Therapy in the Older Adult". Consultant Pharmacist, The Society, Arlington, VA US. Vol. 24, No. Suppl B, Jun. 1, 2009, p. 11-17.

Mendes, F.D, et al. "Recent advances in the treatment of non-alcoholic fatty liver disease". Expert Opinion on Investigational Drugs, vol. 14, No. 1, Jan. 1, 2005, p. 29-35.

Merck Manual of Diagnosis and Therapy: "Obesity." 1999, 17th Edition, Chapter 5, pp. 58-62.

Merck manual, 18th Edition, published Apr. 25, 2007, p. 594-598, Japanese Edition.

Merck: "Initial Therapy with Janumet (sitagliptin/metformin) provided significantly greater blood sugar lowering compared to metformin alone in patients with type 2 diabetes". Webwire.com, Jun. 8, 2009, p.1-4. http://www.webwire.com/ViewPressRel.asp?ald=96695.

Methocel Cellulose Ethers in Aqueous Systems for tablet coating: retrieved from Internet: http;//msdssearch.dow.com/PublishedLiteratureDOWCOM/dh_004a/0901b8038004ab56.pdf?filepath=198-00755.pd?fromPage=GetDoc, published2002. Retrieved Dec. 8, 2017, 3 pages.

Mettler Toledo "interpreting DSC curves Part 1: Dynamic Measurements" Jan. 2000. Available from www.masointechnology.ie.x/Usercom_11.pdf, 28 pages.

Mikhail, Investigating Drugs, Incretin Mimetics and dipeptidyl peptidase 4 inhibitors in clinical trials for the treatment of Type 2 diabetes, vol. 17, 2008, p. 845-853.

Mikhail, Nasser, "Incretin mimetics and dipeptidyl peptidase 4 inhibitors in clinical trials for the treatment of type 2 diabetes." Expert Opinion on Investigational Drugs, 2008, vol. 17, No. 6, pp. 845-853.

MIMS Jan. 2009, "Sitagliptin." pp. 152-153.

Mojsov, Insulintropin: Glucagin like peptide: Lab of Molecular Endocrinology, vol. 79, 1987, p. 616-619.

Morhenn, "Keratinacyte proliferation n wound healing and skin diseases", Immunology Today, vol. 9, Issue 4, 1988, p. 104.

Moritoh, Y. et al., "Combination treatment with alogliptin and voglibose increases active GLP-1 circulation, prevents the development of diabetes and preserves pancreatic beta-cells in prediabetic db/db mice." Diabetes, Obesity and Metabolism, 2010, vol. 12, pp. 224-233.

Nabors, Lyn O'Brien "Alternative Sweeteners." Marcel Dekker, Inc., 2001, pp. 235, 339-340.

Nachaegari, Coprocessed Excipients for Solid Dosage Forms, Pharmaceutical technology, 2004, 8 pages.

Naik, R. et al., "Latent Autoimmune Diabetes in Adults." The Journal of Clinical Endocrinology and Metabolism, 2009, vol. 94, No. 12, pp. 4635-4644.

Nar, Herbert "Analysis of Binding Kinetics and Thermodynamics of DPP-4 Inhibitors and their Relationship to Structure." 2nd NovAliX Conference: Biophysics in drug discovery, Strasbourg, France, Jun. 9-12, 2015.

Nathan, D. et al., "Management of Hyperglycemia in Type 2 Diabetes: A Consensus Algorithm for the Initiation and Adjustment of Therapy." Diabetes Care, Aug. 2006, vol. 29, No. 8, pp. 1963-1972.

National Program for Care Guidelines, "Type 2 Diabetes mellitus." 2002, First Edition, pp. 1-50.

Nauck, M. A. et al., "Efficacy and Safety of the Dipeptidyl Peptidase-4 Inhibitor, Sitagliptin, Compared with the Sulfonylurea, Glipizide, in Patients with Type 2 Diabetes Inaduately Controlled on Metformin alone: A Randomized, Double-Blind, Non-Inferiority Trial." Dlabetes Obesity and Metabolism, 2007, vol. 9, No. 2, pp. 194-205.

Nielsen, L., "Incretin Mimetics and DPP-IV Inhibitors for the Treatment of Type 2 Diabetes." Drug Discovery Today, 2005, vol. 10, No. 10, pp. 703-710.

Nihon Ijinpo, Japan Medicinal Journal, 2001, No. 4032, p. 137.

Novartis AG, Investor Relations Release, "Galvus, a new oral treatment for type 2 diabetes, receives positive opinion recommending European Union approval." Securities and Exchange Commission, Form 6-K, 2007, pp. 1-4.

Nursten, The Mailard Reaction, Chemistry, Biochemistry, and Implications, Chapter 10, 2018, p. 1-8.

O'Farrell, et al., "Pharmacokinetic and Pharmacodynamic Assessments of the Dipeptidyl Peptidase-4 Inhibitor PHX1149: Double-

(56) References Cited

OTHER PUBLICATIONS

Blind, Placebo-controlled, Single-and Multiple-Dose Studies in Healthy Subjects". Clinical Therapeutics, Excerpta Medica, Princeton, NJ, vol. 29, No. 8, 2007, p. 1692-1705.
Office Action for U.S. Appl. No. 10/695,597 mailed May 2, 2008.
Okano, Renal Clearance, New General Pharmaceutics, Revised 3rd Edition, 1987 p. 213-215.
Oz, Helieh S., "Methionine Deficiency and Hepatic Injury in a Dietary Steatohepatitis Model." Digestive Diseases and Sciences, 2008, vol. 53, No. 3, pp. 767-776.
Patani George A. et al: "Bioisoterism : A Rational Approach in Drug Design", Chemical Reviews, 1996, vol. 96, No. 8, pp. 3147-3176.
Pearson, E. R. et al., "Variation in TCF7L2 Influences Therapeutic Response to Sulfonylureas." Diabetes, 2007, vol. 56, pp. 2178-2182.
Pei, Z.: "From the bench to the bedside: Dipeptidyl peptidase IV inhibitors, a new class of oral antihyperglycemic agents" Current Opinion in Drug Discovery and Development, Current Drugs, London, GB vol. 11, No. 4, Jul. 1, 2008 pp. 512-532.
Pham, New Onset Diabetes Mellitus After Solid Organ Transplantation, Endocrinology and Metabolism Clinics of North America, 2007, p. 873-890.
Pharmaceutical Manufacturing and Storage (Concepts and Design, Inc.) 2009.
Pietruck, F. et al., "Rosiglitazone is a safe and effective treatment option of new-onset diabetes mellitus after renal transplantation." Transplant International, 2005, vol. 18, pp. 483-486.
Pilgaard, K. et al., "The T allele of rs7903146 TCF7L2 is associated with impaired insulinotropic action of incretin hormones, reduced 24 h profiles of plasma insulin and glucagon, and increased hepatic glucose production in young healthy men." Diabetologia, 2009, vol. 52, pp. 1298-1307.
Plummer, C.J.G. et al., "The Effect of Melting Point Distributions on DSC Melting Peaks." Polymer Bulletin, 1996, vol. 36, pp. 355-360.
Portincasa, Current Pharmacological Treatment of Nonalcoholic Fatty Liver, Current Medicinal Chem, 2006, p. 2889-2900.
Pospisilik, et al; Dipeptidyl Peptidase IV Inhibitor Treatment Stimulates ?—Cell Survival and Islet Neogenesis in Streptozotocin-Induced Diabetic Rats; Diabetes, vol. 52, Mar. 2003 pp. 741-750.
Poudel, Resham R., "Latent autoimmune diabetes of adults: From oral hypoglycemic agents to early insulin." Indian Journal of Endocrinology and Metabolism, 2012, vol. 16, Supplement 1, pp. S41-S46.
Pratley, R. et al., "Inhibition of DPP-4: a new therapeutic approach for the treatment of type 2 diabetes." Current Medical Research and Opinion, 2007, vol. 23, No. 4, pp. 919-931.
Pregelatinized Starch, Drugs.com, derived from https://drugs.com/inactive/pregelatinized-starch-136.html, accessed Nov. 17, 2017.
Prescribing Information, Package insert for Leprinton tablets 100mg, Manufacturer: Tatsumi Kagaku Co., Ltd., Mar. 2003, pp. 1-3.
Priimenko, B. A., et al; Synthesis and Pharmacological Activity of Derivates of 6,8-Dimethyl Imidazo(1,2-f) Xanthine-(Russ.); Khimiko-Farmatsevticheskii zhurnal (1984) vol. 18, No. 12 pp. 1456-1461.
Rademecker, Regis et al., "Lipodystrophy Reactions to Insulin." American Journal of Clinical Dermatology, 2007, vol. 8, pp. 21-28.
Rask-Madsen, C. et al., "Podocytes lose their footing." Nature, 2010, vol. 468, pp. 42-44.
Rhee et al: "Nitrogen-15-Labeled Deoxynucleosides. 3. Synthesis of [3-15N]-2'-Deoxyadenosine" J. Am. Chem. Soc. 1990, 112, 8174-8175.
Tanaka, S. et al; "Suppression of Arthritis by the Inhibitors of Dipeptidyl Peptidase IV," In. J. Immunopharmac., vol. 19, No. 1, pp. 15-24, 1997.
Tang, Protection of DPP-4 inhibitors on cardiovascular, Drug Evaluation, vol. 9, 2012, p. 6-9,.
Targher, G. et al., "Prevalence of Nonalcoholic Fatty Liver Disease and Its Association With Cardiovascular Disease Among Type 2 Diabetic Patients." Diabetes Care, 2007, vol. 30, No. 5, pp. 1212-1218.
Taskinen, M.-R. et al., "Safety and efficacy of linagliptin as add-on therapy to metformin in patients with type 2 diabetes: a randomized, double-blind, placebo-controlled study." Diabetes, Obesity and Metabolism, 2011, vol. 13, pp. 65-74.
The Textbook of Pharmaceutics, Pharmaceutical Subcommittee Hanrimwon, 2005, p. 1-6.
The textbooks of Pharmaceutics, Department of Pharmacy, Pharmaceutical Committee, 1996.
The Textbooks of Pharmaceutics, Department of Pharmacy, Pharmaceutical Subcommitee, 2000.
Third Party Observation for application No. EP20070728655, May 13, 2013.
Thomas, (R)-8-Amino-piperidin-1-yl)-7-but-2-ynyl-3-methyl-1-(4-methyl-quinazolin-2-ylmethyl)-3,7-dihydro-purine-2,6-dione(BI1236, a Novel Xanthine based Dipeptidyl Peptidase 4 inhibitor, has a Superior Potency and longer duration of action compared with other dipeptyl Peptidase-4 inhibitors, The Journal of Pharmacology and Experimental Therapeutica, vol. 325, 2008, p. 175-182.
Thomas, L. et al., "BI 1356, a novel and selective xanthine beased DPP-IV inhibitor, exhibits a superior profile when compared to sitagliptin and vildagliptin." Diabetologia, 2007, vol. 50, No. Suppl. 1, p. S363.
Thomas, L., "Chronic treatment with the Dipeptidyl Peptidase-4 Inhibitor BI 1356[9R)-8-(3-Amino-piperidin-1-yl)-7-but-2-ynyl-3-methyl-1(4-methyl-quinazolin-2-ylmethyl)-3,7-dihydro-purine-2,6-dione] Increases Basal Glucagon-Like Peptide-1 and Improves Glycemic Control in Diabetic Rodent Models" The Journal of Pharmacology and Experimental Therapeutics, Feb. 2009, vol. 328, No. 2, pp. 556-563,.
Thomas, Leo et al: "(R)-8-(3-Amino-piperidin-1-yl)-7-but-2-ynyl-3-methyl-1-(4-methyl-quinazolin-2-ylmethyl)-3,7-dihydro-purine-2,6-dione (BI 1356), a Novel Xanthine-Based Dipeptidyl Peptidase 4 Inhibitor . . . "Journal of Pharmacology and Experimental Therapeutics, 2008, vol. 325, No. 1, p. 177.
Thornber, C.W., "Isosterism and Molecular Modification in Drug Design." Chemical Society Reviews, 1979, pp. 563-580.
Tiwari, Linagliptin, A dipeptyl peptidase-4 inhibitor for the treatment of type 2 diabetes, Current Opinion in Ivestigational Drugs, vol. 10, 2009, p. 1091-1104.
Tounyoubyou, "Symposium-19: Future Perspectives on Incretion Therapy in Diabetes." 2008, vol. 51, Suppl. 1, p. S-71, S19-2.
Tradjenta, Highlights of Prescribing Information (revised Sep. 2012).
Tribulova, N. et al. "Chronic Disturbances in NO Production Results in Histochemical and Subcellular Alterations of the Rat Heart." Physiol. Res., 2000, vol. 49, No. 1, pp. 77-88.
Tsujihata, et al., "TAK-875, an orally available G protein-Coupled receptor 40/Free fatty acid receptor 1 Agonist, Enhances Glucose Dependent Insulin Secretion and improves both Postprandial and Fasting hyperglycemia in type 2 Diabetic rats", J. Pharm Exp. 2011, vol. 339, No. 1, p. 228-237.
Tsuprykov, O. et al., Linagliptin is as Efficacious as Telmisartan in Preventing Renal Disease Progression in Rats with 5/6 Nephrectomy, 73rd Annual Meeting Science Session, ADA, Chicago, Jun. 2013.
Turner, R.C. et al., "Glycemic Control With Diet, Sulfonylurea, Metformin, or Insulin in Patients With Type 2 Diabetes Mellitus Progressive Requirement for Multiple Therapies (UKPDS 49)" The Journal of the American Medical Association, 1999, vol. 281, No. 21, pp. 2005-2012.
U.S. Appl. No. 15/235,575, filed Aug. 12, 2016, Inventor: Klaus DUGI. (The cited pending U.S. application is stored in the USPTO IFW system (MPEP 609.04(a)(II)(C)).
Uhlig-Laske, B. et al., "Linagliptin, a Potent and Selective DPP-4 Inhibitior, is Safe and Efficacious in Patients with Inadequately Controlled Type 2 Diabetes Despite Metformin Therapy". 535-P Clinical Therapeutics/New Technology—Pharmacologic Treatment of Diabetes or Its Complications, Posters, vol. 58, Jun. 5, 2009, p. A143.
United Healthcare, "Diabetes." Retrieved from internet on Aug. 22, 2013, http://www.uhc.com/source4women/health_topics/diabetesirelatedinformation/
d0f0417b073bf110VgnVCM1000002f1Ob10a _. htm.

(56) References Cited

OTHER PUBLICATIONS

Van Heek, M. et al., "Ezetimibe, a Potent Cholesterol Absorption Inhibitor, Normalizes Combined Dyslipidemia in Obese Hyperinsulinemic Hamsters." Diabetes, 2001, vol. 50, pp. 1330-1335.
Vichayanrat, A. et al., "Efficacy and safety of voglibose in comparison with acarbose in type 2 diabetic patients." Diabetes Research and Clinical Practice, 2002, vol. 55, pp. 99-103.
Mllhauer, E.B., "1-[[3-Hydroxy-1-adamantyl)amino]acetyl]-1-cyano-(S)-pyrrolidine: A Potent, Selective, and Orally Bioavailable Dipeptidyl Peptidase IV Inhibitor with Antihyperglycemic Properties" Journal Med. Chem, 2003, 46, p. 2774-2789.
Villhauer, E.B., et al., "1-{2-{5-Cyanopyridin-2-yl)amino}-ethylamino}acetyl-1-1(S)-pyrrolidine-carbonitrile: A Potent, Selective, and Orally Bioavailable Dipeptidyl Peptidase IV Inhibitor with Antihyperglycemic Properties". Journal of Medical Chemistry, 2002, vol. 45, No. 12, p. 2362-2365.
Vincent, S.H. et al., "Metabolism And Excretion of the Dipeptidyl Peptidase 4 Inhibitor [14C]Sitagliptin in Humans." Drug Metabolism And Disposition, 2007, vol. 35, No. 4, pp. 533-538.
Wang, Y. et al., "BI-1356. Dipeptidyl-Peptidase IV Inhibitor, Antidiabetic Agent." Drugs of the Future, 2008, vol. 33, No. 6, pp. 473-477.
Waterman, Accelerating aging-Prediction of Chemical Stability of Pharmaceuticals, International Journal of Pharmaceutics, 2005, vol. 293, p. 101-125.
Weber, Ann E., "Dipeptidyl Peptidase IV Inhibitors for the Treatment of Diabetes." Journal of Medicinal Chemistry, 2004, vol. 47, pp. 4135-4141.
WebMD, Autoimmune Diseases: What Are They? Who Gets Them? "What Are Autoimmune Disorders?" 2015, pp. 1-3. Retrieved online Jul. 9, 2015. http://www.webmd.com/a-to-z-guides/autoimmune-diseases.
Westerhuis, Optimisation of the composition and production of mannitol cellulose tablets International Journal of Pharmaceutics, 1996, p. 143, 151-162.
White, Cardiovascular Events in patients receiving alogliptin, Diabetes Pro, 2010, vol. 59, p. 391.
White, John R. Jr., "Dipeptidyl Peptidase-IV Inhibitors: Phamacological Profile and Clinical Use". Clinical Diabetes, Apr. 2008, vol. 26, No. 2, pp. 53-57.
Wikipedia, "Linagliptin" Sep. 12, 2015. <https://en.wikipedia.org/w/index.php?title=Linagliptin&oldid=333469979>.
Wikipedia, Annulation. Jun. 23, 2008, http://en.wikipedia.org/wiki/Annelation.
Wikipedia, Polyvinylpyrrolidone, https:en.wikipedia.org/wiki/ access date May 15, 2018.
Wikipedia, the free encyclopedia, The carbonyl group, 2017, 1 page.
Williams-Herman, D. et al., "Efficacy and safety of initial combination therapy with sitagliptin and metformin in patients with type 2 diabetes: a 54-week study". Current Medical Research and Opinion, Informa Healthcare, GB, vol. 25, No. 3, Jan. 2009, p. 569-583.
Wirth, D. et al., "Maillard Reaction of Lactose and Fluoxetine Hydrochloride, a Secondary Amine." Journal of Pharmaceutical Sciences, 1998, vol. 87, No. 1, pp. 31-39.
Witteles, R. M. et al., "Dipeptidyl Peptidase 4 Inhibition Increases Myocardial Glucose Uptake in Nonischemic Cardiomyopathy." Journal of Cardiac Failure, 2012, vol. 18, No. 10, pp. 804-809.
Wolff, M.E.: "Burger's Medicinal Chemistry and Drug Discovery" Fifth Edition, vol. 1: Principles and Practice, pp. 975-977, 1994, John Wiley & Sons, Inc.,.
World Health Organization (WHO). "Addendum 1 to "The use of stems in the selection of International Nonproprietary names (INN) for pharmaceutical substances"" Online Jun. 19, 2007, pp. 1-3, retrieved from URL: http://www.who.int/medicindedocs/index/assoc/s1414e/s1414e.pdf.
Wu, Reactive Impurities in Excipients-Profiling, American Association of Pharmaceutical Scientists, 2011, vol. 12, No. 4, p. 1248-1263.
X-Ray Diffraction. The United States Pharmacopeia, 2002, USP 25 NF20, p. 2088-2089.
Yale, Jean-Francois, "Oral Antihyperglycemic Agents and Renal Disease: New Agents, New Concepts." Journal of the American Society of Nephrology, 2005, vol. 16, Suppl. 1, pp. S7-S10.
Yamagishi, S. et al., "Pleiotropic Effects of Glucagon-like Peptide-1 (GLP-1)-Based Therapies on Vascular Complications in Diabetes." Current Pharmaceutical Design, 2012, vol. 17, pp. 4379-4385.
Yamazaki, Comparison of Efficacies of a Dipeptidyl Peptidase IV Inhibitor and a-Glucosodase Inhibitors in Oral Carbohydrate and Meal Tolerance Tests and their Effects of their tolerance in mice, J. Pharmacol Science, 2007, p. 29-38.
Yap, W.S. et al., "Review of management of type 2 diabetes mellitus." Journal of Clinical Pharmacy and Therapeutics, 1998, vol. 23, pp. 457-465.

\* cited by examiner

MEDICAL USE OF PHARMACEUTICAL COMBINATION OR COMPOSITION

FIELD OF THE INVENTION

The present invention relates to a certain DPP-4 inhibitor (preferably linagliptin) for use in combination with metformin (particularly in the form of metformin hydrochloride) in CKD (chronic kidney disease) patients, particularly in patients having CKD up to stage 3 and/or having estimated glomerular filtration rate (eGFR; mL/minute/1.73 m$^2$) levels down to 45, or even down to 30, such as in patients with CKD of moderate stage (CKD stage 3, eGFR 30-60), particularly of mild-to-moderate stage (CKD stage 3a) such as having eGFR levels 45-59 or of moderate-to-severe stage such as having eGFR levels 30-44 (CKD stage 3b), optionally in combination with one or more other active substances.

BACKGROUND OF THE INVENTION

Type 2 diabetes mellitus is a common chronic and progressive disease arising from a complex pathophysiology involving the dual endocrine effects of insulin resistance and impaired insulin secretion with the consequence not meeting the required demands to maintain plasma glucose levels in the normal range. This leads to chronic hyperglycaemia and its associated micro- and macrovascular complications or chronic damages, such as e.g. diabetic nephropathy, retinopathy or neuropathy, or macrovascular (e.g. cardio- or cerebrovascular) complications, and/or cognitive function impairment. The vascular disease component plays a significant role, but is not the only factor in the spectrum of diabetes associated disorders. The high frequency of complications leads to a significant reduction of life expectancy. Diabetes is currently the most frequent cause of adult-onset loss of vision, renal failure, and amputation in the Industrialized World because of diabetes induced complications and is associated with a two to five fold increase in cardiovascular disease risk. The elevated risk for macrovascular disease is primarily related to increased risk for atherothrombosis that leads to increased morbidity and premature mortality from cardiovascular (CV) disease and an important predictor for CV diseases is renal impairment, nephropathy and/or chronic kidney disease (CKD) which often co-exists.

The treatment of type 2 diabetes typically begins with diet and exercise, followed by oral antidiabetic monotherapy, and although conventional monotherapy may initially control blood glucose in some patients, it is however associated with a high secondary failure rate. The limitations of single-agent therapy for maintaining glycemic control may be overcome, at least in some patients, and for a limited period of time by combining multiple drugs to achieve reductions in blood glucose that cannot be sustained during long-term therapy with single agents. Available data support the conclusion that in most patients with type 2 diabetes current monotherapy will fail and treatment with multiple drugs will be required. But, because type 2 diabetes is a progressive disease, even patients with good initial responses to conventional combination therapy will eventually require an increase of the dosage or further treatment with an additional oral or non-oral antidiabetic drug (often finally with insulin therapy) because the blood glucose level is very difficult to maintain stable for a long period of time. Although existing combination therapy has the potential to enhance glycemic control, it is not without limitations (especially with regard to long term efficacy). Further, traditional therapies may show an increased risk for side effects, such as hypoglycemia or weight gain, which may compromise their efficacy and acceptability.

Thus, for many patients, these existing drug therapies result in progressive deterioration in metabolic control despite treatment and do not sufficiently control metabolic status especially over long-term and thus fail to achieve and to maintain glycemic control in advanced, progressed or late stage type 2 diabetes, including diabetes with inadequate glycemic control despite conventional oral and/or non-oral antidiabetic medication.

Therefore, although intensive treatment of hyperglycemia can reduce the incidence of chronic damages, many patients with diabetes remain inadequately treated, partly because of limitations in long term efficacy, safety/tolerability and dosing inconvenience of conventional antihyperglycemic therapies.

In addition, obesity, overweight or weight gain (e.g. as side or adverse effect of some conventional antidiabetic medications) further complicates the treatment of diabetes and its microvascular or macrovascular, and/or cognitive, complications.

This high incidence of therapeutic failure is a major contributor to the high rate of long-term hyperglycemia-associated complications or chronic damages (including micro- and macrovascular complications such as e.g. diabetic nephrophathy, retinopathy or neuropathy, or cerebro- or cardiovascular complications such as e.g. myocardial infarction, stroke or vascular mortality or morbidity) in patients with diabetes.

Oral antidiabetic drugs conventionally used in therapy (such as e.g. first-, second- or third-line, and/or mono- or (initial or add-on) combination therapy) may include, without being restricted thereto, metformin, sulphonylureas, thiazolidinediones, glinides and α-glucosidase inhibitors.

Non-oral (typically injected) antidiabetic drugs conventionally used in therapy (such as e.g. first-, second- or third-line, and/or mono- or (initial or add-on) combination therapy) may include, without being restricted thereto, GLP-1 or GLP-1 analogues, and insulin or insulin analogues.

However, the use of these conventional antidiabetic or antihyperglycemic agents can be associated with various adverse effects. For example, metformin can be associated with lactic acidosis or gastrointestinal side effects; sulfonylureas, glinides and insulin or insulin analogues can be associated with hypoglycemia and weight gain; thiazolidinediones can be associated with edema, bone fracture, weight gain and heart failure/cardiac effects; and alpha-glucosidase blockers and GLP-1 or GLP-1 analogues can be associated with gastrointestinal adverse effects (e.g. dyspepsia, flatulence or diarrhea, or nausea or vomiting).

In addition to morbidity associated with each of these side effects, they could also have adverse cardiovascular implications. For example, hypoglycaemia and weight gain are postulated as contributors to adverse CV mortality outcomes.

Hypoglycemic episodes have also been identified detrimental to cognitive skills and are associated with a greater risk of cognitive impairment or dementia. The risk of hypoglycemia is further increased in the elderly with comorbidities and multiple medication use.

Therefore, it remains a need in the art to provide efficacious, safe and tolerable antidiabetic therapies.

In particular, a certain amount of people with type 2 diabetes mellitus have chronic kidney disease (CKD). For these individuals, the current standard of care is intensive glycemic control and treatment with angiotensin-converting enzyme (ACE) inhibitors or angiotensin II receptor blockers (ARBs).

Despite such treatment, type 2 diabetes patients with chronic kidney disease (particularly having residual albuminuria) still have substantial risk for cardio-renal morbidity and mortality, an unmet need that is driving a search for novel therapies for diabetic kidney disease.

Accordingly, it remains a need in the art to provide efficacious, safe and tolerable antidiabetic therapies both for diabetic patients such as who have not previously been treated with an antidiabetic drug (drug-naïve patients) and, particularly, for patients with advanced or late stage type 2 diabetes mellitus, including patients with inadequate glycemic control on conventional oral and/or non-oral antidiabetic drugs, such as e.g. metformin, sulphonylureas, thiazolidinediones, glinides and/or α-glucosidase inhibitors, and/or GLP-1 or GLP-1 analogues, and/or insulin or insulin analogues; particularly in patients with (chronic) renal disease, renal dysfunction or renal impairment, including in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) having eGFR levels 45-59, or even of moderate-to-severe stage having eGFR levels 30-44 (CKD stage 3b).

Particularly, it is a need for therapies for diabetic patients with moderate-to-severe microvascular burden, such as advanced kidney disease.

Further, within the therapy of type 2 diabetes, it is a need for treating the condition effectively, avoiding the (micro- and/or macrovascular) complications inherent to the condition, and delaying or modifying disease progression, e.g. in order to achieve a long-lasting therapeutic benefit.

Furthermore, it remains a need that antidiabetic treatments not only prevent and/or treat the long-term complications often found in advanced stages of diabetes disease, but also are a therapeutic option in those diabetes patients who have developed or are at-risk of developing such complications (e.g. chronic kidney disease/diabetic nephropathy, renal impairment and/or albuminuria).

There is a need that antidiabetic treatments prevent and/or treat preferably both microvascular (renal) complications and macrovascular (CV) complications together, preferably within one therapy.

There is also a need to provide a therapeutic option in those diabetes patients who have developed or are at-risk of developing both microvascular (renal) complications and macrovascular (CV) complications.

Also, there is a need that antidiabetic treatments prevent and/or treat accelerated cognitive decline (which may be associated with micro- and/or macrovascular complications), preferably together with both microvascular (renal) complications and macrovascular (CV) complications, preferably within one therapy.

Moreover, it remains a need to provide prevention or reduction of risk for adverse effects associated with conventional antidiabetic therapies.

SUMMARY OF THE INVENTION

The present invention relates to use of a certain DPP-4 inhibitor (preferably linagliptin) in combination with metformin (particularly in the form of metformin hydrochloride) in CKD (chronic kidney disease) patients, particularly in patients having CKD up to stage 3 and/or having estimated glomerular filtration rate (eGFR; mL/minute/1.73 m$^2$) levels down to 45, or even down to 30, such as in patients with CKD of moderate stage (CKD stage 3, eGFR 30-60), particularly of mild-to-moderate stage (CKD stage 3a) such as having eGFR levels 45-59 or of moderate-to-severe stage such as having eGFR levels 30-44 (CKD stage 3b), optionally in combination with one or more other active substances.

The present invention relates to certain medical uses of a combination or a pharmaceutical composition comprising a certain DPP-4 inhibitor (preferably linagliptin) and metformin (particularly in the form of metformin hydrochloride), such as e.g. for treating and/or preventing metabolic diseases, especially type 2 diabetes mellitus and/or conditions related thereto (e.g. diabetic complications), including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45, or even down to 30, such as in patients with (chronic) renal impairment of moderate stage (CKD stage 3, eGFR 30-60), particularly of mild-to-moderate stage (CKD stage 3a) such as having eGFR levels 45-59 or of moderate-to-severe stage such as having eGFR levels 30-44 (CKD stage 3b); optionally in combination with one or more other active substances.

The present invention further relates to the medical use of a combination or a pharmaceutical composition comprising a certain DPP-4 inhibitor (preferably linagliptin) and metformin (particularly in the form of metformin hydrochloride), for treating and/or preventing chronic kidney disease (CKD) such as e.g. up to stage 3 and/or having estimated glomerular filtration rate (eGFR; mL/minute/1.73 m$^2$) levels down to 45, or even down to 30, such as of moderate stage (CKD stage 3, eGFR 30-60), particularly of mild-to-moderate stage (CKD stage 3a) such as having eGFR levels 45-59 or of moderate-to-severe stage such as having eGFR levels 30-44 (CKD stage 3b); optionally in combination with one or more other active substances (such as e.g. antidiabetic and/or an angiotensin-converting enzyme (ACE) inhibitor or an angiotensin II receptor blocker (ARB)).

The present invention yet further relates to a certain DPP-4 inhibitor (preferably linagliptin) in combination with metformin (particularly in the form of metformin hydrochloride) (and optionally in combination with one or more other active agents) for use in therapy, prophylaxis, treatment or prevention of diabetic (preferably type 2 diabetes) patients (preferably for use in cardio- and/or renoprotective therapy preferably of type 2 diabetes in human patients), including in patients (preferably type 2 diabetes patients) with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45, or even down to 30, such as in patients with (chronic) renal impairment of moderate stage (CKD stage 3, eGFR 30-60), particularly of mild-to-moderate stage (CKD stage 3a) such as having eGFR levels 45-59 or of moderate-to-severe stage such as having eGFR levels 30-44 (CKD stage 3b); optionally in combination with one or more other active substances.

Further, the present invention relates to a certain DPP-4 inhibitor (preferably linagliptin) for use in combination with metformin (particularly in the form of metformin hydrochloride), such as e.g. such as e.g. for treating type 2 diabetes and treating, decreasing, delaying the onset and/or delaying the progression of diabetic nephropathy, chronic kidney disease, albuminuria (e.g. micro- or macro-albuminuria), renal impairment, retinopathy, neuropathy, learning or memory or cognitive impairment or decline, neurodegenerative or cognitive disorders such as dementia, and/or macrovascular complications such as cardio- or cerebrovascular events such as stroke or myocardial infarction, in patients with type 2 diabetes and micro- or macroalbuminuria, with or without renal function impairment, such as patients with CKD (chronic kidney disease), particularly patients having CKD up to stage 3 and/or having estimated glomerular filtration rate (eGFR; mL/minute/1.73 m$^2$) levels down to 45, or even down to 30, such as patients with CKD of moderate stage (CKD stage 3, eGFR 30-60), particularly of mild-to-moderate stage (CKD stage 3a) such as having eGFR levels 45-59 or of moderate-to-severe stage such as having eGFR levels 30-44 (CKD stage 3b), optionally in combination with one or more other active substances.

The present invention relates to a DPP-4 inhibitor (preferably linagliptin) in combination with metformin (particularly in the form of metformin hydrochloride), for use in treating and/or preventing (including slowing the progression or delaying the onset) of metabolic diseases, particularly diabetes (especially type 2 diabetes mellitus) and/or conditions related thereto (e.g. diabetic complications, particularly diabetic chronic kidney disease); including in patients with (chronic) renal disease, renal dysfunction or renal impairment (impairment of renal function), particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or even of moderate-to-severe stage such as having eGFR levels 30-44 (CKD stage 3b), with or without residual albuminuria (micro- or macroalbuminuria), optionally in combination with one or more other active substances.

Accordingly, the present invention further relates to a DPP-4 inhibitor (preferably linagliptin, preferably in a daily dose of 5 mg, administered 5 mg once daily or 2.5 mg twice daily) for use in combination with metformin (particularly in the form of metformin hydrochloride) in treating and/or preventing (including slowing the progression or delaying the onset) of metabolic diseases, particularly diabetes (especially type 2 diabetes mellitus) and/or conditions related thereto (e.g. diabetic complications, such as one or more selected from diabetic chronic kidney disease, nephropathy, micro- or macroalbuminuria, renal impairment, retinopathy, neuropathy, learning or memory or cognitive impairment or decline, neurodegenerative or cognitive disorders such as dementia, and/or macrovascular complications such as cardio- or cerebrovascular events such as stroke and/or myocardial infarction); including in patients with (chronic) renal disease, renal dysfunction or renal impairment (impairment of renal function), particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or even of moderate-to-severe stage such as having eGFR levels 30-44 (CKD stage 3b), with or without residual albuminuria (micro- or macroalbuminuria), optionally in combination with one or more other active substances (such as selected from other antidiabetics and/or ACE inhibitors or ARBs), particularly wherein the maximum daily dose of metformin (particularly in the form of metformin hydrochloride) administered to patients of mild-to-moderate stage (CKD stage 3a, such as having eGFR levels 45-59) is 2000 mg, and/or particularly wherein the maximum daily dose of metformin (particularly in the form of metformin hydrochloride) administered to patients of moderate-to-severe stage (CKD stage 3b, such as having eGFR levels 30-44) is 1000 mg.

Also, the present invention relates to a pharmaceutical combination or composition comprising a DPP-4 inhibitor (preferably linagliptin), metformin (particularly in the form of metformin hydrochloride) and optionally one or more pharmaceutically acceptable auxiliaries, for use in treating and/or preventing (including slowing the progression or delaying the onset) of metabolic diseases, particularly diabetes (especially type 2 diabetes mellitus) and/or conditions related thereto (e.g. diabetic complications, particularly diabetic chronic kidney disease), including in patients with (chronic) renal disease, renal dysfunction or renal impairment (impairment of renal function), particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or of moderate-to-severe stage such as having eGFR levels 30-44 (CKD stage 3b), with or without residual albuminuria (micro- or macroalbuminuria); optionally in combination with one or more other active substances.

Also, the present invention relates to a combination therapy comprising using a DPP-4 inhibitor (preferably linagliptin) and metformin (particularly in the form of metformin hydrochloride) for treating and/or preventing (including slowing the progression or delaying the onset) of metabolic diseases, particularly diabetes (especially type 2 diabetes mellitus) and/or conditions related thereto (e.g. diabetic complications, particularly diabetic chronic kidney disease), including in patients with (chronic) renal disease, renal dysfunction or renal impairment (impairment of renal function), particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or of moderate-to-severe stage such as having eGFR levels 30-44 (CKD stage 3b), with or without residual albuminuria (micro- or macroalbuminuria); optionally in combination with one or more other active substances.

The present invention further relates to a certain DPP-4 inhibitor (preferably linagliptin) in combination with metformin (particularly in the form of metformin hydrochloride), and optionally in combination with one or more other active agents, for use in therapy or treatment of diabetes (preferably type 2 diabetes) in (human) patients in need thereof, preferably for use in cardio- and/or renoprotective therapy preferably of type 2 diabetes in human patients, such as e.g. including treating type 2 diabetes and/or preventing diabetic complications such as decreasing, protecting against, delaying the onset, slowing progression and/or
reducing the risk of (cardio)vascular and/or renal morbidity and/or mortality, such as e.g.
  i) treating, preventing or delaying the progression of chronic kidney disease (diabetic nephropathy); and/or
  ii) treating, decreasing, preventing, protecting against, delaying the progression, delaying the occurrence and/or reducing the risk of albuminuria (e.g. micro- or macro-albuminuria) and/or renal impairment; and/or
  iii) preventing, protecting against, reducing the risk of and/or delaying the occurrence of a cardio- or cerebrovascular disease, complication or event selected from: cardiovascular (CV) death (including fatal stroke, fatal myocardial infarction and sudden death), non-fatal stroke, non-fatal myocardial infarction (MI) (silent MI may be excluded) and, optionally, hospitalization for unstable angina pectoris; and/or
  iv) preventing, protecting against, reducing the risk of, delaying the progression and/or delaying the occurrence of a renal microvascular disease, complication or event selected from: renal death, end-stage renal disease and loss in estimated glomerular filtration rate (e.g. eGFR≥50% from baseline); and/or
  v) decreasing, preventing, protecting against, delaying (e.g. occurrence or progression) and/or reducing the risk of (accelerated) cognitive decline or cognitive impairment or dementia;
including in patients (preferably type 2 diabetes patients) with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45, or even down to 30, such as in patients with (chronic) renal impairment of moderate stage (CKD stage 3, eGFR 30-60), particularly of mild-to-moderate stage (CKD stage 3a) such as having eGFR levels 45-59 or of moderate-to-severe stage such as having eGFR levels 30-44 (CKD stage 3b); optionally in combination with one or more other active substances; wherein such patients may be with or at-risk of further (major) (micro- and/or macro-)vascular diseases, complications or events, e.g. such patients may be at high vascular risk.

Other aspects of the present invention become apparent to the skilled person from the foregoing and following remarks (including the examples and claims).

DETAILED DESCRIPTION OF THE INVENTION

Within the scope of the present invention it has now been found that certain DPP-4 inhibitors as defined herein as well as combinations or pharmaceutical compositions of these DPP-4 inhibitors with metformin (particularly in the form of metformin hydrochloride) as well as their use have particularly useful properties or effects, which make them suitable for the purpose of this invention and/or for fulfilling one or more of the needs mentioned herein.

For example, combinations or pharmaceutical compositions of these DPP-4 inhibitors with metformin (particularly in the form of metformin hydrochloride) are useful for improving glycemic control and/or for treating and/or preventing (including slowing the progression or delaying the onset) of metabolic diseases, particularly diabetes (especially type 2 diabetes mellitus) and/or conditions related thereto (e.g. diabetic complications, particularly diabetic chronic kidney disease, or diabetic nephropathy, micro- or macroalbuminuria and/or renal impairment), such as in drug naïve type 2 diabetes patients and/or in patients with advanced or late stage type 2 diabetes, including patients with insufficient glycemic control despite a therapy with an oral and/or a non-oral antidiabetic or antihyperglycemic drug and/or with indication on insulin; including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or even of moderate-to-severe stage such as having eGFR levels 30-44 (CKD stage 3b), with or without residual albuminuria, especially including in patients with (chronic) renal impairment of mild-to-moderate stage (CKD stage 3a) such as having estimated glomerular filtration rate [eGFR] 45-59 mL/minute/1.73 m$^2$ or creatinine clearance [CrCl] 45-59 mL/min, optionally in combination with one or more other active substances.

For example, patients having chronic kidney disease (CKD) such as e.g. up to stage 3 and/or having estimated glomerular filtration rate (eGFR; mL/minute/1.73 m$^2$) levels down to 45 or even down to 30 are amenable to the combination therapy according to the present invention comprising using linagliptin (in a total daily dose of 5 mg) in combination with metformin (e.g. up to maximum total daily dose of 1000 mg metformin hydrochloride (such as e.g. for CKD 3a patients) or 2000 mg metformin hydrochloride (such as e.g. for CKD 3b patients)), preferably using a tablet containing 2.5 mg linagliptin and 500 mg, 850 mg or 1000 mg metformin hydrochloride (in immediate release form) each administered twice daily, or using a tablet containing 5 mg linagliptin and 1000 mg metformin hydrochloride (in extended release form) administered once daily, or using a tablet containing 2.5 mg linagliptin and 750 mg or 1000 mg metformin hydrochloride (in extended release form) each administered as two tablets once daily.

In an embodiment, the maximum daily dose of metformin (particularly in the form of metformin hydrochloride) administered to patients of mild-to-moderate stage (CKD stage 3a, such as having eGFR levels 45-59) may be 2000 mg, which may be given as two divided doses, such as e.g. 1000 mg twice daily; (the starting dose may be at most half of the maximum dose).

In an embodiment, the maximum daily dose of metformin (particularly in the form of metformin hydrochloride) administered to patients of moderate-to-severe stage (CKD stage 3b, such as having eGFR levels 30-44) may be 1000 mg, which may be given as two divided doses, such as e.g. 500 mg twice daily; (the starting dose may be at most half of the maximum dose).

For patients with severe or very severe stage of renal impairment (CKD stage 4, such as having eGFR levels<30; or CKD stage 5, such as having eGFR levels<15, end-stage renal disease), metformin is contraindicated.

The combination therapy according to the present invention using linagliptin (in a total daily dose of 5 mg) in combination with metformin is also useful for patients in need of >1000 mg metformin daily (e.g. 850 mg or 1000 mg metformin hydrochloride BID) for sufficient glycemic control and having chronic kidney disease (CKD), such as e.g. up to stage 3 and/or having estimated glomerular filtration rate (eGFR; mL/minute/1.73 m$^2$) levels down to 45 (or, in certain instances, even down to 30); preferably by using a tablet containing 2.5 mg linagliptin and 850 mg or 1000 mg metformin hydrochloride (in immediate release form) each administered twice daily, or using a tablet containing 2.5 mg linagliptin and 750 mg or 1000 mg metformin hydrochloride (in extended release form) each administered as two tablets once daily.

For further example, patients in need of >1000 mg metformin daily (e.g. 1000 mg metformin hydrochloride BID) for sufficient glycemic control but with dose limitation for metformin due to renal impairment (e.g. maximum total daily dose of 1000 mg metformin hydrochloride), such as having moderate renal impairment, e.g., in certain instances, patients with (chronic) renal impairment of mild-to-moderate stage (CKD stage 3a) such as having eGFR levels 45-59 mL/minute/1.73 m$^2$, or especially of moderate-to-severe stage (CKD stage 3b) such as having eGFR levels 30-44 mL/minute/1.73 m$^2$, benefit from the combination therapy according to the present invention comprising using linagliptin (in a total daily dose of 5 mg) in combination with metformin (e.g. up to maximum total daily dose of 1000 mg metformin hydrochloride), preferably using a tablet containing 2.5 mg linagliptin and 500 mg metformin hydrochloride, administered twice daily.

Accordingly, patients with dose limitation for metformin due to renal impairment (e.g. maximum total daily dose of 2000 mg metformin hydrochloride), e.g. with (chronic) renal impairment of mild-to-moderate stage (CKD stage 3a) such as having eGFR levels 45-59 mL/minute/1.73 m$^2$, benefit from the combination therapy according to the present invention comprising using linagliptin (in a total daily dose of 5 mg) in combination with metformin (e.g. up to maximum total daily dose of 2000 mg metformin hydrochloride), preferably using a tablet containing 2.5 mg linagliptin and 1000 mg metformin hydrochloride, administered twice daily.

Accordingly, patients with dose limitation for metformin due to renal impairment (e.g. maximum total daily dose of 1000 mg metformin hydrochloride), e.g. with (chronic) renal impairment of moderate-to-severe stage (CKD stage 3b) such as having eGFR levels 30-44 mL/minute/1.73 m$^2$, benefit from the combination therapy according to the present invention comprising using linagliptin (in a total daily dose of 5 mg) in combination with metformin (e.g. up to maximum total daily dose of 1000 mg metformin hydrochloride), preferably using a tablet containing 2.5 mg linagliptin and 500 mg metformin hydrochloride, administered twice daily.

In an embodiment, patients on linagliptin (in a total daily dose of 5 mg) in combination with metformin (up to maximum total daily dose of 2000 mg metformin hydrochloride), using a tablet containing 2.5 mg linagliptin and 850 mg, administered twice daily, or a tablet containing 2.5 mg linagliptin and 1000 mg metformin hydrochloride, administered twice daily, can maintain these treatments until they reach an eGFR of 45 mL/min/1.73 m$^2$ (this would not be the case for patients using another major DPP-4 inhibitor (gliptin) other than linagliptin, requiring dose adjustment of the DPP-4 inhibitor component leading to change in the treatment scheme, except for linagliptin).

In a further embodiment, patients with an eGFR between 45 and 59 mL/min/1.73 m$^2$ (CKD stage 3a) already on the maximum dose of metformin (e.g. maximum total daily dose of 2000 mg metformin hydrochloride) can use linagliptin (in a total daily dose of 5 mg) in combination with metformin (e.g. maximum total daily dose of 2000 mg metformin hydrochloride), preferably using a tablet containing 2.5 mg linagliptin and 1000 mg metformin hydrochloride, administered twice daily, when additional therapy is deemed necessary.

In a further embodiment, patients on linagliptin (in a total daily dose of 5 mg) in combination with metformin (e.g. up to maximum total daily dose of 1000 mg metformin hydrochloride), using a tablet containing 2.5 mg linagliptin and 500 mg, administered twice daily, can maintain these treatments until they reach an eGFR of 30 mL/min/1.73 m$^2$ (this would not be the case for patients using another major DPP-4 inhibitor (gliptin) other than linagliptin, requiring dose adjustment of the DPP-4 inhibitor component leading to change in the treatment scheme, except for linagliptin).

In a further embodiment, patients with an eGFR between 30 and 44 mL/min/1.73 m$^2$ (CKD stage 3b) already on the maximum dose of metformin (e.g. maximum total daily dose of 1000 mg metformin hydrochloride) can use linagliptin (in a total daily dose of 5 mg) in combination with metformin (e.g. maximum total daily dose of 1000 mg metformin hydrochloride), preferably using a tablet containing 2.5 mg linagliptin and 500 mg metformin hydrochloride, administered twice daily, when additional therapy is deemed necessary.

In a yet further embodiment, patients with an eGFR between 45 and 59 mL/min/1.73 m$^2$ (CKD stage 3a) who are not receiving metformin can up-titrate to the maximum dose of metformin (e.g. up to maximum total daily dose of 2000 mg metformin hydrochloride) and can then start to use linagliptin (in a total daily dose of 5 mg) in combination with metformin (e.g. up to maximum total daily dose of 2000 mg metformin hydrochloride), preferably using a tablet containing 2.5 mg linagliptin and 850 mg or 1000 mg metformin hydrochloride, administered twice daily.

In a yet further embodiment, patients with an eGFR between 30 and 44 mL/min/1.73 m$^2$ (CKD stage 3b) who are not receiving metformin can up-titrate to the maximum dose of metformin (e.g. up to maximum total daily dose of 1000 mg metformin hydrochloride) and can then start to use linagliptin (in a total daily dose of 5 mg) in combination with metformin (e.g. up to maximum total daily dose of 1000 mg metformin hydrochloride), preferably using a tablet containing 2.5 mg linagliptin and 500 mg metformin hydrochloride, administered twice daily.

In a still yet further embodiment, patients with an eGFR between 45 and 59 mL/min/1.73 m$^2$ (CKD stage 3a) who are not receiving metformin can use linagliptin (in a total daily dose of 5 mg) in combination with metformin (e.g. up to maximum total daily dose of 2000 mg metformin hydrochloride), preferably using a tablet containing 2.5 mg linagliptin and 850 mg or 1000 mg metformin hydrochloride, administered twice daily, to start treatment.

In a still yet further embodiment, patients with an eGFR between 30 and 44 mL/min/1.73 m$^2$ (CKD stage 3b) who are not receiving metformin can use linagliptin (in a total daily dose of 5 mg) in combination with metformin (e.g. up to maximum total daily dose of 1000 mg metformin hydrochloride), preferably using a tablet containing 2.5 mg linagliptin and 500 mg metformin hydrochloride, administered twice daily, to start treatment.

It has been found that 2.5 mg linagliptin/500 mg metformin hydrochloride BID combination therapy is at least as effective as 1000 mg metformin BID monotherapy, thereby offering an alternative for patients intolerant to such high dose of metformin or with dose limit for metformin due to renal impairment.

The combination therapy according to this invention using a DPP-4 inhibitor (particularly linagliptin) and metformin (e.g. 2.5 mg linagliptin/500 mg metformin hydrochloride BID) is more effective for patients with (chronic) renal impairment, such as of mild-to-moderate stage (CKD stage 3a) or even of moderate-to-severe stage (CKD stage 3b), than metformin alone.

Accordingly, a particular embodiment of the combination therapy according to the present invention for patients with (chronic) renal impairment (CKD) relates to 2.5 mg linagliptin/500 mg metformin hydrochloride BID.

A more particular embodiment of the combination therapy according to the present invention relates to 2.5 mg linagliptin/500 mg metformin hydrochloride administered twice daily to patients with (chronic) renal impairment of moderate-to-severe stage such as having eGFR levels 30-44 (CKD stage 3b).

Further, the combination therapy according to this invention using a DPP-4 inhibitor (particularly linagliptin) and metformin (optionally in combination with one or more further active agents) has beneficial potential on cardio-renal morbidity and/or mortality (cardio- and/or renoprotection) in diabetic kidney disease patients as described herein (especially in type 2 diabetes patients with advanced CKD and/or over long-term treatment):

For example, the combination therapy according to the present invention using a DPP-4 inhibitor (particularly linagliptin) and metformin (optionally in combination with one or more further active agents)
  i) prevents, protects against, reduces the risk of and/or delays the occurrence of a cardio- or cerebrovascular disease, complication or event selected from: cardiovascular (CV) death (including fatal stroke, fatal myocardial infarction and sudden death), non-fatal stroke, non-fatal myocardial infarction (MI) (silent MI may be excluded) and, optionally, hospitalisation for unstable angina pectoris; and/or
  ii) prevents, protects against, reduces the risk of, delays the progression and/or delays the occurrence of a renal microvascular disease, complication or event selected from: renal death, end-stage renal disease and loss in estimated glomerular filtration rate (e.g. eGFR 50% from baseline).

For further example, the combination therapy according to the present invention using a DPP-4 inhibitor (particularly linagliptin) and metformin (optionally in combination with one or more further active agents)
  i) prevents, protects against, reduces the risk of, delays the progression and/or delays the occurrence of a renal microvascular disease, complication or event selected from: renal death, end-stage renal disease and loss in estimated glomerular filtration rate (e.g. eGFR 50% from baseline).

For yet further example, the combination therapy according to the present invention using a DPP-4 inhibitor (particularly linagliptin) and metformin (optionally in combination with one or more further active agents)
  i) decreases, prevents, protects against, delays (e.g. occurrence or progression) and/or reduces the risk of (accelerated) cognitive decline or cognitive impairment or dementia.

For yet further example, the combination therapy according to the present invention using a DPP-4 inhibitor (particularly linagliptin) and metformin (optionally in combination with one or more further active agents)
  i) treats, decreases, prevents, protects against, delays (e.g. occurrence or progression) and/or reduces the risk of diabetic nephropathy.

For yet further example, the combination therapy according to the present invention using a DPP-4 inhibitor (particularly linagliptin) and metformin (optionally in combination with one or more further active agents)
  i) treats, decreases, prevents, protects against, delays (e.g. occurrence or progression) and/or reduces the risk of albuminuria (e.g. micro- or macroalbuminuria).

For yet further example, the combination therapy according to the present invention using a DPP-4 inhibitor (particularly linagliptin) and metformin (optionally in combination with one or more further active agents)
  i) treats, decreases, prevents, protects against, delays (e.g. occurrence or progression) and/or reduces the risk of renal impairment.

Accordingly, a combination therapy according to the present invention using a DPP-4 inhibitor (particularly linagliptin) and metformin is particularly useful for treating and/or preventing (including delaying the onset or slowing the progression) of metabolic diseases, particularly diabetes (especially type 2 diabetes mellitus) and/or conditions related thereto (e.g. diabetic complications, particularly diabetic chronic kidney disease, or diabetic nephropathy, micro- or macroalbuminuria and/or renal impairment), in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or even of moderate-to-severe stage such as having eGFR levels 30-44 (CKD stage 3b), with or without albuminuria, especially including in patients with (chronic) renal impairment of mild-to-moderate stage (CKD stage 3a) having eGFR levels 45-59;
  optionally in combination with one or more other active substances, such as e.g. any of those mentioned herein,
    such as e.g. optionally in combination with one or more other antidiabetics such as selected from a sulphonylurea, a thiazolidinedione (e.g. pioglitazone), a glinide, an alpha-glucosidase blocker, GLP-1 or a GLP-1 analogue, and insulin or an insulin analogue, and/or an angiotensin converting enzyme (ACE) inhibitor or an angiotensin receptor blocker (ARB).

Further, the combination therapy according to the present invention using a DPP-4 inhibitor (particularly linagliptin) and metformin is particularly useful for treating and/or preventing (including delaying the onset or slowing the progression) of renal microvascular disease, such as selected from (diabetic) chronic kidney disease (CKD), diabetic nephropathy, albuminuria (e.g. micro- or macro-albuminuria), renal impairment, renal death, end-stage renal disease and/or loss in estimated glomerular filtration rate (e.g. eGFR>=50% from baseline), in patients (particularly in type 2 diabetes patients) with (chronic) renal disease, renal dysfunction or renal impairment, particularly in patients having chronic kidney disease (CKD, particularly advanced CKD), such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR particularly of mild-to-moderate stage (CKD stage 3a) such as having eGFR levels 45-59, or even of moderate-to-severe stage such as having eGFR levels 30-44 (CKD stage 3b), with or without albuminuria, especially including in patients with (chronic) renal impairment of mild-to-moderate stage (CKD stage 3a) having eGFR levels 45-59;
optionally in combination with one or more other active substances, such as e.g. any of those mentioned herein, such as e.g. optionally in combination with one or more other antidiabetics such as selected from a sulphonylurea, a thiazolidinedione (e.g. pioglitazone), a glinide, an alpha-glucosidase blocker, GLP-1 or a GLP-1 analogue, and insulin or an insulin analogue, and/or an angiotensin converting enzyme (ACE) inhibitor or an angiotensin receptor blocker (ARB); particularly over long-term treatment.

An embodiment of patients with (chronic) renal impairment (CKD) as described herein relates to type 2 diabetes patients having impaired renal function such as indicated herein with micro- or macroalbuminuria (e.g. urine albumin creatinine ratio (UACR) 30-3000 mg/g creatinine).

Another embodiment of patients with (chronic) renal impairment (CKD) as described herein relates to type 2 diabetes patients having impaired renal function such as indicated herein without micro- or macroalbuminuria (e.g. urine albumin creatinine ratio (UACR) 30-3000 mg/g creatinine).

A sub-embodiment of patients with (chronic) renal impairment (CKD) as described herein relates to type 2 diabetes patients having impaired renal function of moderate-to-severe stage (CKD 3b) with any albuminuria (e.g. urine albumin creatinine ratio (UACR)>=30 mg/g creatinine).

Another sub-embodiment of patients with (chronic) renal impairment (CKD) as described herein relates to type 2 diabetes patients having impaired renal function of up to mild-to-moderate stage (CKD 3a) with macro-albuminuria (e.g. urine albumin creatinine ratio (UACR)>200 mg/g creatinine).

A further embodiment of patients with (chronic) renal impairment (CKD) as described herein relates to type 2 diabetes patients at early stages of prevalent renal microvascular complications, such as e.g. having microalbuminuria (e.g. 30-200 or 30-300 mg/g creatinine) and/or early impaired renal function (eGFR, and/or early CKD stage).

Another further embodiment of patients with (chronic) renal impairment (CKD) as described herein relates to type 2 diabetes patients at advanced stages of prevalent renal microvascular complications, such as e.g. having macroalbuminuria (e.g. >200 or >300 mg/g creatinine) and/or advanced impaired renal function (eGFR, and/or advanced CKD stage).

A further embodiment of patients with (chronic) renal impairment (CKD) as described herein relates to type 2 diabetes patients having micro- or macroalbuminuria; optionally with or without renal function impairment.

A yet further embodiment of patients with (chronic) renal impairment (CKD) as described herein relates to type 2 diabetes patients having microalbuminuria, with renal function impairment.

A yet further embodiment of patients with (chronic) renal impairment (CKD) as described herein relates to type 2 diabetes patients having macroalbuminuria, with renal function impairment.

A further embodiment of patients with (chronic) renal impairment (CKD) as described herein relates to type 2 diabetes patients having impaired renal function such as indicated herein, with or without micro- or macroalbuminuria, and having a previous macrovascular disease (e.g. myocardial infarction, coronary artery disease, stroke, carotid artery disease or peripheral artery disease).

In a further embodiment, the patients as described herein are treated with a DPP-4 inhibitor (particularly linagliptin) and metformin (particularly in the form of metformin hydrochloride) on top of or in add-on combination with one or more other (conventional) antidiabetics and/or an angiotensin converting enzyme (ACE) inhibitor or an angiotensin receptor blocker (ARB).

In a further embodiment, the patients as described herein may be with or at-risk of further (major) (micro- and/or macro-)vascular diseases, complications or events, such as e.g. such patients may be at high vascular risk.

For example, such patients at high vascular risk may have:
both
albuminuria (e.g. micro- or macro-albuminuria)
and
previous macrovascular (e.g. cardio- or cerebrovascular) disease (such as e.g. myocardial infarction, coronary artery disease, (ischemic or haemorrhagic) stroke, carotid artery disease and/or peripheral artery disease), and/or
either
(mild or moderate) renal impairment (e.g. CKD stage 1, 2 or 3, such as CKD stage 1, 2 (mild) or 3a (mild-moderate), preferably eGFR≥45-75 mL/min/1.73 m$^2$) with macro-albuminuria,
or
(moderate [or severe]) renal impairment (e.g. CKD stage 3 [or 4], such as CKD stage 3b (moderate-severe) [or 4 (severe), preferably eGFR 15-45 mL/min/1.73 m$^2$]), with or without any albuminuria (such as e.g. with or without micro- or macro-albuminuria).

In more detail, such a patient at high vascular risk (e.g. at high risk of CV events) may be a patient (preferably diabetic, particularly type 2 diabetes patients) as follows:
with
albuminuria (such as e.g. urine albumin creatinine ratio (UACR)≥30 mg/g creatinine or ≥30 mg/l (milligram albumin per liter of urine) or ≥30 µg/min (microgram albumin per minute) or ≥30 mg/24 h (milligram albumin per 24 hours)) and
previous macrovascular disease, such as e.g. defined as one or more of a) to f):
a) previous myocardial infarction,
b) advanced coronary artery disease,
c) high-risk single-vessel coronary artery disease,
d) previous ischemic or haemorrhagic stroke,
e) presence of carotid artery disease,
f) presence of peripheral artery disease,
and/or
with
impaired renal function (e.g. with or without CV co-morbidities), such as e.g. defined by:
impaired renal function (e.g. as defined by MDRD formula) with an eGFR [15 or] 30-45 mL/min/1.73 m$^2$ with any urine albumin creatinine ratio (UACR), and/or
impaired renal function (e.g. as defined by MDRD formula) with an eGFR≥45-75 mL/min/1.73 m$^2$ with an urine albumin creatinine ratio (UACR)>200 mg/g creatinine or >200 mg/l (milligram albumin per liter of urine) or >200 µg/min (microgram albumin per minute) or >200 mg/24 h (milligram albumin per 24 hours).

The present invention relates to a combination or a pharmaceutical composition comprising a certain DPP-4 inhibitor (particularly linagliptin) and metformin (particularly in the form of metformin hydrochloride) such as for simultaneous, separate or sequential use in the therapies or treatments described herein.

The present invention also relates to a fixed or free combination or pharmaceutical composition comprising, consisting essentially of or made of
- a certain DPP-4 inhibitor (particularly linagliptin) and metformin (particularly in the form of metformin hydrochloride) each as defined herein,
- and optionally one or more pharmaceutically acceptable auxiliaries (such as e.g. including excipients, stabilizers, carriers or the like), for medical uses as described herein,
- such as e.g. for improving glycemic control and/or for use in treating and/or preventing (including slowing the progression and/or delaying the onset) of metabolic diseases, especially type 2 diabetes mellitus and/or conditions related thereto (e.g. diabetic complications, such as e.g. diabetic chronic kidney disease, diabetic nephropathy, micro- or macroalbuminuria, renal impairment, diabetic retinopathy and/or diabetic neuropathy, and/or a macrovascular complication), such as e.g.
- either as first line therapy, i.e. in type 2 diabetes patients who have not previously treated with an antihyperglycemic agent (drug-naïve patients),
- or as second or third line therapy, i.e. in type 2 diabetes patients with insufficient glycemic control despite therapy with one or two conventional antihyperglycemic agents selected from metformin, sulphonylureas, thiazolidinediones (e.g. pioglitazone), glinides, alpha-glucosidase blockers, GLP-1 or GLP-1 analogues, and insulin or insulin analogues;
- including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or even of moderate-to-severe stage such as having eGFR levels 30-44 (CKD stage 3b);
- optionally in combination with one or more other active substances, such as e.g. any of those mentioned herein,
- such as e.g. optionally in combination with one conventional antihyperglycemic agent selected from sulphonylureas, thiazolidinediones (e.g. pioglitazone), glinides, alpha-glucosidase blockers, GLP-1 or GLP-1 analogues, and insulin or insulin analogues, and/or angiotensin converting enzyme (ACE) inhibitors or an angiotensin receptor blockers (ARBs).

The present invention also relates to medical uses as described herein of a pharmaceutical composition comprising a fixed dose combination formulation of a DPP-4 inhibitor and metformin (particularly in the form of metformin hydrochloride) and optionally one or more pharmaceutically acceptable auxiliaries.

In one embodiment, the present invention also relates to a fixed or free combination or pharmaceutical composition comprising or consisting essentially of a DPP-4 inhibitor (particularly linagliptin), metformin (particularly in the form of metformin hydrochloride) and optionally one or more pharmaceutically acceptable auxiliaries, for use in treating and/or preventing (including slowing the progression and/or delaying the onset) of metabolic diseases, especially type 2 diabetes mellitus and/or conditions related thereto (e.g. diabetic complications), such as e.g.
- either as first line therapy, i.e. in type 2 diabetes patients who have not previously treated with an antihyperglycemic agent (drug-naïve patients),
- or as second or third line therapy, i.e. in type 2 diabetes patients with insufficient glycemic control despite therapy with one or two conventional antihyperglycemic agents selected from metformin, sulphonylureas, thiazolidinediones, glinides, alpha-glucosidase blockers, GLP-1 or GLP-1 analogues, and insulin or insulin analogues;
- including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) having eGFR levels 45-59, or even of moderate-to-severe stage having eGFR levels 30-44 (CKD stage 3b);
- optionally in combination with one or more other active substances,
- such as e.g. optionally in combination with one or more other antidiabetics such as selected from sulphonylureas, thiazolidinediones (e.g. pioglitazone), glinides, alpha-glucosidase blockers, GLP-1 or GLP-1 analogues, and insulin or insulin analogues, and/or an angiotensin converting enzyme (ACE) inhibitor or an angiotensin receptor blocker (ARB).

In a particular embodiment, the present invention relates to a combination or pharmaceutical composition comprising a DPP-4 inhibitor (particularly linagliptin), metformin (particularly in the form of metformin hydrochloride) and optionally one or more pharmaceutically acceptable auxiliaries, for use in treating and/or preventing (including slowing the progression and/or delaying the onset) of metabolic diseases, especially type 2 diabetes mellitus and/or conditions related thereto (e.g. diabetic complications, such as e.g. diabetic chronic kidney disease, diabetic nephropathy, micro- or macroalbuminuria, renal impairment, diabetic retinopathy and/or diabetic neuropathy, and/or a macrovascular complication such as a cardio- or cerebrovascular event), in type 2 diabetes patients with insufficient glycemic control despite mono-therapy with metformin;
- wherein the patients have (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) having eGFR levels 45-59, or even of moderate-to-severe stage having eGFR levels 30-44 (CKD stage 3b).

In another particular embodiment, the present invention also relates to a combination or pharmaceutical composition comprising a DPP-4 inhibitor (particularly linagliptin), metformin (particularly in the form of metformin hydrochloride) and optionally one or more pharmaceutically acceptable auxiliaries, for use in combination with a sulphonylurea in treating and/or preventing (including slowing the progression and/or delaying the onset) of metabolic diseases, especially type 2 diabetes mellitus and/or conditions related thereto (e.g. diabetic complications, such as e.g. diabetic chronic kidney disease, diabetic nephropathy, micro- or macroalbuminuria, renal impairment, diabetic retinopathy and/or diabetic neuropathy, and/or a macrovascular complication such as a cardio- or cerebrovascular event), in type 2 diabetes patients with insufficient glycemic control despite dual combination therapy with metformin and a sulphonylurea;

wherein the patients have (chronic) renal disease, renal dysfunction or renal impairment, particularly patients having chronic kidney disease (CKD) such as e.g. up to stage 3 and/or having estimated glomerular filtration rate (eGFR; mL/minute/1.73 m$^2$) levels down to 45 or even down to 30, such as patients with (chronic) renal impairment of moderate stage (CKD stage 3, eGFR 30-60), particularly of mild-to-moderate stage (CKD stage 3a) having eGFR levels 45-59 or even of moderate-to-severe stage having eGFR levels 30-44 (CKD stage 3b).

In another particular embodiment, the present invention also relates to a combination or pharmaceutical composition comprising a DPP-4 inhibitor (particularly linagliptin), metformin (particularly in the form of metformin hydrochloride) and optionally one or more pharmaceutically acceptable auxiliaries, for use in combination with a thiazolidinedione (e.g. pioglitazone) in treating and/or preventing (including slowing the progression and/or delaying the onset) of metabolic diseases, especially type 2 diabetes mellitus and/or conditions related thereto (e.g. diabetic complications, such as e.g. diabetic chronic kidney disease, diabetic nephropathy, micro- or macroalbuminuria, renal impairment, diabetic retinopathy and/or diabetic neuropathy, and/or a macrovascular complication such as a cardio- or cerebrovascular event), in type 2 diabetes patients with insufficient glycemic control despite dual combination therapy with metformin and a thiazolidinedione (e.g. pioglitazone); wherein the patients have (chronic) renal disease, renal dysfunction or renal impairment, particularly patients having chronic kidney disease (CKD) such as, e.g., up to stage 3 and/or having estimated glomerular filtration rate (eGFR; mL/minute/1.73 m$^2$) levels down to 45 or even down to 30, such as patients with (chronic) renal impairment of moderate stage (CKD stage 3, eGFR 30-60), particularly of mild-to-moderate stage (CKD stage 3a) having eGFR levels 45-59 or even of moderate-to-severe stage having eGFR levels 30-44 (CKD stage 3b).

In another particular embodiment, the present invention also relates to a combination or pharmaceutical composition comprising a DPP-4 inhibitor (particularly linagliptin), metformin (particularly in the form of metformin hydrochloride) and optionally one or more pharmaceutically acceptable auxiliaries, for use in combination with an insulin (e.g. basal insulin) in treating and/or preventing (including slowing the progression and/or delaying the onset) of metabolic diseases, especially type 2 diabetes mellitus and/or conditions related thereto (e.g. diabetic complications, such as e.g. diabetic chronic kidney disease, diabetic nephropathy, micro- or macroalbuminuria, renal impairment, diabetic retinopathy and/or diabetic neuropathy, and/or a macrovascular complication such as a cardio- or cerebrovascular event), in type 2 diabetes patients with insufficient glycemic control despite dual combination therapy with metformin and an insulin (e.g. basal insulin);

wherein the patients have (chronic) renal disease, renal dysfunction or renal impairment, particularly patients having chronic kidney disease (CKD) such as e.g. up to stage 3 and/or having estimated glomerular filtration rate (eGFR; mL/minute/1.73 m$^2$) levels down to 45 or even down to 30, such as patients with (chronic) renal impairment of moderate stage (CKD stage 3, eGFR 30-60), particularly of mild-to-moderate stage (CKD stage 3a) having eGFR levels 45-59 or even of moderate-to-severe stage having eGFR levels 30-44 (CKD stage 3b).

In another particular embodiment, the present invention also relates to a combination or pharmaceutical composition comprising a DPP-4 inhibitor (particularly linagliptin), metformin (particularly in the form of metformin hydrochloride) and optionally one or more pharmaceutically acceptable auxiliaries, for use in treating and/or preventing (including slowing the progression and/or delaying the onset) of metabolic diseases, especially type 2 diabetes mellitus and/or conditions related thereto (e.g. diabetic complications), in drug-naïve type 2 diabetes patients (e.g. as first line therapy), such as e.g. as early or initial combination therapy;

wherein the patients have (chronic) renal disease, renal dysfunction or renal impairment, particularly patients having chronic kidney disease (CKD) such as, e.g., up to stage 3 and/or having estimated glomerular filtration rate (eGFR; mL/minute/1.73 m$^2$) levels down to 45 or even down to 30, such as patients with (chronic) renal impairment of moderate stage (CKD stage 3, eGFR 30-60), particularly of mild-to-moderate stage (CKD stage 3a) having eGFR levels 45-59 or even of moderate-to-severe stage having eGFR levels 30-44 (CKD stage 3b).

The present invention further provides the use of a combination or pharmaceutical composition comprising a DPP-4 inhibitor (particularly linagliptin), metformin (particularly in the form of metformin hydrochloride) and optionally one or more pharmaceutically acceptable auxiliaries, for the manufacture of a medicament for treating and/or preventing metabolic diseases, particularly type 2 diabetes mellitus and/or conditions related thereto (e.g. diabetic complications), e.g. as first, second or third line therapy as described herein, including in the patients as described herein.

The present invention further relates to a pharmaceutical package comprising a pharmaceutical composition as defined herein and optionally instructions for its use, optionally in combination with one or more other active substances, in the treatment and/or prevention of metabolic diseases, particularly type 2 diabetes mellitus and/or conditions related thereto (e.g. diabetic complications), such as e.g. in drug-naïve patients or in patients with insufficient glycemic control despite therapy with one or two conventional antihyperglycemic agents selected from metformin, sulphonylureas, thiazolidinediones, glinides, alpha-glucosidase blockers, GLP-1 or GLP-1 analogues, and insulin or insulin analogues; preferably in patients with (chronic) renal disease, renal dysfunction or renal impairment, particularly in patients having chronic kidney disease (CKD) such as, e.g., up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or even of moderate-to-severe stage such as having eGFR levels 30-44 (CKD stage 3b).

The present invention further relates to a medicament for use in the treatment and/or prevention of metabolic diseases, particularly type 2 diabetes mellitus and/or conditions related thereto (e.g. diabetic complications), such as e.g. in drug-naïve patients or in patients with insufficient glycemic control despite therapy with one or two conventional antihyperglycemic agents selected from metformin, sulphonylureas, thiazolidinediones, glinides, alpha-glucosidase blockers, GLP-1 or GLP-1 analogues, and insulin or insulin analogues; preferably in patients with (chronic) renal disease, renal dysfunction or renal impairment, particularly in patients having chronic kidney disease (CKD) such as, e.g., to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or even of moderate-to-severe stage such as having eGFR levels 30-44 (CKD stage 3b); said medicament comprising a pharmaceutical composition comprising a DPP-4 inhibitor (particularly linagliptin), metformin (particularly in the form of metformin hydrochloride) and optionally one or more pharmaceutically acceptable auxiliaries; optionally in combination with one or more other active substances, such as e.g. any of those mentioned herein, such as e.g. for separate, sequential, simultaneous, concurrent or chronologically staggered use of the active ingredients.

The present invention further provides a method of treating and/or preventing metabolic diseases, particularly type 2 diabetes mellitus and/or conditions related thereto (e.g. diabetic complications), such as e.g. in drug-naïve patients (e.g. as first line therapy) or in patients with insufficient glycemic control despite therapy with one or two conventional antihyperglycemic agents selected from metformin, sulphonylureas, thiazolidinediones, glinides, alpha-glucosidase blockers, GLP-1 or GLP-1 analogues, and insulin or insulin analogues (e.g. as second or third line therapy); preferably in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) such as having eGFR levels 45-59, or even of moderate-to-severe stage such as having eGFR levels 30-44 (CKD stage 3b); said method comprising administering to a subject in need thereof (particularly a human patient) an effective amount of a pharmaceutically composition comprising a DPP-4 inhibitor (particularly linagliptin), metformin (particularly in the form of metformin hydrochloride) and optionally one or more pharmaceutically acceptable auxiliaries, optionally alone or in combination, such as e.g. separately, sequentially, simultaneously, concurrently or chronologically staggered, with an effective amount of one or more other active substances, such as e.g. any of those mentioned herein.

In a particular embodiment, the present invention provides a method of treating and/or preventing metabolic diseases, particularly type 2 diabetes mellitus and/or conditions related thereto (e.g. diabetic complications), in drug-naïve patients (e.g. as first line therapy); including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) having eGFR levels 45-59, or even of moderate-to-severe stage having eGFR levels 30-44 (CKD stage 3b); said method comprising administering to a subject in need thereof (particularly a human patient) an effective amount of a pharmaceutically composition of a DPP-4 inhibitor (particularly linagliptin) and metformin (particularly in the form of metformin hydrochloride) such as described herein.

In another particular embodiment, the present invention provides a method of treating and/or preventing metabolic diseases, particularly type 2 diabetes mellitus and/or conditions related thereto (e.g. diabetic complications), in patients with insufficient glycemic control despite mono-therapy with metformin (e.g. as second line therapy); including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) having eGFR levels 45-59, or even of moderate-to-severe stage having eGFR levels 30-44 (CKD stage 3b); said method comprising administering to a subject in need thereof (particularly a human patient) an effective amount of a pharmaceutically composition of a DPP-4 inhibitor (particularly linagliptin) and metformin (particularly in the form of metformin hydrochloride) such as described herein.

In another particular embodiment, the present invention provides a method of treating and/or preventing metabolic diseases, particularly type 2 diabetes mellitus and/or conditions related thereto (e.g. diabetic complications), in patients with insufficient glycemic control despite dual combination therapy with metformin and a thiazolidinedione (e.g. as third line therapy); including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) having eGFR levels 45-59, or even of moderate-to-severe stage having eGFR levels 30-44 (CKD stage 3b); said method comprising administering to a subject in need thereof (particularly a human patient) an effective amount of a pharmaceutically composition of a DPP-4 inhibitor (particularly linagliptin) and metformin (particularly in the form of metformin hydrochloride) such as described herein, and a thiazolidinedione.

In another particular embodiment, the present invention provides a method of treating and/or preventing metabolic diseases, particularly type 2 diabetes mellitus and/or conditions related thereto (e.g. diabetic complications), in patients with insufficient glycemic control despite dual combination therapy with metformin and a sulphonylurea (e.g. as third line therapy); including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) having eGFR levels 45-59, or even of moderate-to-severe stage having eGFR levels 30-44 (CKD stage 3b); said method comprising administering to a subject in need thereof (particularly a human patient) an effective amount of a pharmaceutically composition of a DPP-4 inhibitor (particularly linagliptin) and metformin (particularly in the form of metformin hydrochloride) such as described herein, and a sulphonylurea.

In a further embodiment, the present invention provides a method of treating and/or preventing metabolic diseases, particularly type 2 diabetes mellitus and/or conditions related thereto (e.g. diabetic complications), in patients with insufficient glycemic control despite dual combination therapy with metformin and insulin or insulin analog; including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) having eGFR levels 45-59, or even of moderate-to-severe stage having eGFR levels 30-44 (CKD stage 3b); said method comprising administering to a subject in need thereof (particularly a human patient) an effective amount of a pharmaceutically composition of a DPP-4 inhibitor (particularly linagliptin) and metformin (particularly in the form of metformin hydrochloride) such as described herein, and insulin or insulin analog.

In a further embodiment, the present invention provides a method of treating and/or preventing metabolic diseases, particularly type 2 diabetes mellitus and/or conditions related thereto (e.g. diabetic complications), in patients treated with insulin or insulin analog;
  including in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45 or even down to 30, such as in patients with (chronic) renal impairment of moderate stage (CKD stage 3, eGFR 30-60), particularly of mild-to-moderate stage (CKD stage 3a) having eGFR levels 45-59, or even of moderate-to-severe stage having eGFR levels 30-44 (CKD stage 3b); said method comprising administering to a subject in need thereof (particularly a human patient) an effective amount of a pharmaceutically composition of a DPP-4 inhibitor (particularly linagliptin) and metformin (particularly in the form of metformin hydrochloride) such as described herein, thereby replacing said insulin or insulin analog (i.e. switching from insulin therapy to a BI 1356 & metformin combination according to this invention).

Examples of metabolic disorders or diseases amenable by the therapy of this invention may include, without being limited to, type 1 diabetes, type 2 diabetes, diabetic complications (e.g. as described herein), impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyperNEFA-emia, fasting or postprandial hyperlipidemia such as postprandial lipemia (e.g. postprandial hypertriglyceridemia), hypertension, atherosclerosis, endothelial dysfunction, osteoporosis, chronic systemic inflammation, non alcoholic fatty liver disease (NAFLD), retinopathy, neuropathy, nephropathy, polycystic ovarian syndrome, and/or metabolic syndrome.

The present invention further relates to a certain DPP-4 inhibitor (preferably linagliptin) in combination with metformin (particularly in the form of metformin hydrochloride), and optionally in combination with one or more other active agents, for use in at least one of the following methods:
  preventing, slowing the progression of, delaying the onset of or treating a metabolic disorder or disease, such as e.g. type 1 diabetes mellitus, type 2 diabetes mellitus, impaired glucose tolerance (IGT), impaired fasting blood glucose (IFG), hyperglycemia, postprandial hyperglycemia, postabsorptive hyperglycemia, latent autoimmune diabetes in adults (LADA), overweight, obesity, dyslipidemia, hyperlipidemia, hypercholesterolemia, hypertriglyceridemia, hyperNEFA-emia, postprandial lipemia (e.g. postprandial hypertriglyceridemia), hypertension, atherosclerosis, endothelial dysfunction, osteoporosis, chronic systemic inflammation, non alcoholic fatty liver disease (NAFLD), retinopathy, neuropathy, nephropathy, polycystic ovarian syndrome, and/or metabolic syndrome;
  improving and/or maintaining glycemic control and/or for reducing of fasting plasma glucose, of postprandial plasma glucose, of postabsorptive plasma glucose and/or of glycosylated hemoglobin HbA1c, or preventing, reducing the risk of, slowing the progression of, delaying the onset of or treating worsening or deterioration of glycemic control, need for insulin therapy or elevated HbA1c despite treatment;
  preventing, slowing, delaying the onset of or reversing progression from pre-diabetes, impaired glucose tolerance (IGT), impaired fasting blood glucose (IFG), insulin resistance and/or from metabolic syndrome to type 2 diabetes mellitus;
  preventing, reducing the risk of, slowing the progression of, delaying the onset of or treating of complications of diabetes mellitus such as micro- and macrovascular diseases, such as nephropathy, micro- or macroalbuminuria, proteinuria, retinopathy, cataracts, neuropathy, learning or memory or cognitive impairment or decline, neurodegenerative or cognitive disorders (e.g. dementia), cardio- or cerebrovascular diseases, tissue ischaemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy, heart failure, heart rhythm disorders, vascular restenosis, and/or stroke;
  reducing body weight and/or body fat and/or liver fat and/or intra-myocellular fat or preventing an increase in body weight and/or body fat and/or liver fat and/or intra-myocellular fat or facilitating a reduction in body weight and/or body fat and/or liver fat and/or intra-myocellular fat;
  preventing, slowing, delaying the onset of or treating the degeneration of pancreatic beta cells and/or the decline of the functionality of pancreatic beta cells and/or for improving, preserving and/or restoring the functionality of pancreatic beta cells and/or stimulating and/or restoring or protecting the functionality of pancreatic insulin secretion;
  preventing, slowing, delaying the onset of or treating non alcoholic fatty liver disease (NAFLD) including hepatic steatosis, non-alcoholic steatohepatitis (NASH) and/or liver fibrosis (such as e.g. preventing, slowing the progression, delaying the onset of, attenuating, treating or reversing hepatic steatosis, (hepatic) inflammation and/or an abnormal accumulation of liver fat);

preventing, slowing the progression of, delaying the onset of or treating type 2 diabetes with failure to conventional antidiabetic mono- or combination therapy;

achieving a reduction in the dose of conventional antidiabetic medication (e.g. of a sulphonylurea or an insulin) required for adequate therapeutic effect;

reducing the risk for adverse effects associated with conventional antidiabetic medication (e.g. hypoglycemia or weight gain, such as associated with e.g. insulin or sulphonylurea medication); and/or maintaining and/or improving the insulin sensitivity and/or for treating or preventing hyperinsulinemia and/or insulin resistance;

in a patient in need thereof (such as e.g. a patient as described herein), particularly in patients with (chronic) renal disease, renal dysfunction or renal impairment, particularly in patients having chronic kidney disease (CKD) such as e.g. up to stage 3 and/or having estimated glomerular filtration rate (eGFR; mL/minute/1.73 m$^2$) levels down to 45, or even down to 30, such as in patients with (chronic) renal impairment of moderate stage (CKD stage 3, eGFR 30-60), particularly of mild-to-moderate stage (CKD stage 3a) such as having eGFR levels 45-59 or of moderate-to-severe stage such as having eGFR levels 30-44 (CKD stage 3b.

Such therapy according to this invention (e.g. as described hereinabove or hereinbelow in further detail) may include treatment with such certain DPP-4 inhibitor (preferably linagliptin, optionally in combination with one or more other active agents) over a lengthy period, such as described in more detail (duration of treatment) herein.

In certain embodiments, the therapy or prophylaxis according to the present invention (e.g. such as described hereinabove and hereinbelow) may include duration of treatment with a certain DPP-4 inhibitor, particularly linagliptin (preferably 5 mg per day, administered orally, in combination with metformin (and optionally in combination with one or more other active substances, e.g. such as those described herein) over a lengthy period (such as e.g. at least 1-6 years, >/=2 years, or 3-7 years such as 3-4 years, 3-5 years, 3-6 years, 4-5 years, 4-6 years, 5-6 years or 5-7 years, preferably at least 48 months, more preferably at least 3 years); such as e.g. to provide a long term effect or improvement on (cardio)vascular and/or renal (microvascular) safety, morbidity and/or mortality (e.g. including effect on cognitive impairment) according to the present invention; such as e.g. in patients (e.g. diabetic patients, especially type 2 diabetes patients) as described herein.

For example, the therapy or prophylaxis according to the present invention (e.g. such as described hereinabove and hereinbelow) may include duration of treatment with a certain DPP-4 inhibitor, particularly linagliptin (preferably 5 mg per day, administered orally), in combination with metformin (and optionally in combination with one or more other active substances, e.g. such as those described herein) over a lengthy period, preferably at least 48 months, more preferably at least 3 years (such as e.g. at least 3-4 years, or at least 5-6 years).

In the monitoring of the treatment of diabetes mellitus the HbA1c value, the product of a non-enzymatic glycation of the haemoglobin B chain, is of exceptional importance. As its formation depends essentially on the blood sugar level and the life time of the erythrocytes the HbA1c in the sense of a "blood sugar memory" reflects the average blood sugar level of the preceding 4-12 weeks. Diabetic patients whose HbA1c level has been well controlled over a long time by more intensive diabetes treatment (i.e. <6.5% of the total haemoglobin in the sample) are significantly better protected from diabetic microangiopathy. The available treatments for diabetes can give the diabetic an average improvement in their HbA1c level of the order of 1.0-1.5%. This reduction in the HbA1C level is not sufficient in all diabetics to bring them into the desired target range of <7.0%, preferably <6.5% and more preferably <6% HbA1c.

Within glycemic control, in addition to improvement of the HbA1c level, other recommended therapeutic goals for type 2 diabetes mellitus patients are improvement of fasting plasma glucose (FPG) and of postprandial plasma glucose (PPG) levels to normal or as near normal as possible. Recommended desired target ranges of preprandial (fasting) plasma glucose are 90-130 mg/dL (or 70-130 mg/dL) or <110 mg/dL, and of two-hour postprandial plasma glucose are <180 mg/dL or <140 mg/dL.

Within the meaning of this invention, inadequate or insufficient glycemic control means in particular a condition wherein patients show HbA1c values above 6.5%, in particular above 7.0%, even more preferably above 7.5%, especially above 8%. An embodiment of patients with inadequate or insufficient glycemic control include, without being limited to, patients having a HbA1c value from 6.5 to 10% (or, in another embodiment, from 7.5 to 10%; or, in another embodiment, from 7.5 to 11%, or, in another embodiment, from 6.5 to 8.5% or, in another embodiment, from 6.5 to 7.5%). A special sub-embodiment of inadequately controlled patients refers to patients with poor glycemic control including, without being limited, patients having a HbA1c value≥9%.

In an embodiment, diabetes patients within the meaning of this invention may include patients who have not previously been treated with an antidiabetic drug (drug-naïve patients). Thus, in an embodiment, the therapies described herein may be used in naïve patients. In certain embodiments of the therapies of this invention, the DPP-4 inhibitor (preferably linagliptin) may be used alone or in combination with one or more other antidiabetics in such patients. In another embodiment, diabetes patients within the meaning of this invention may include patients pre-treated with conventional antidiabetic background medication, such as e.g. patients with advanced or late stage type 2 diabetes mellitus (including patients with failure to conventional antidiabetic therapy), such as e.g. patients with inadequate glycemic control on one, two or more conventional oral and/or non-oral antidiabetic drugs as defined herein, such as e.g. patients with insufficient glycemic control despite (mono-)therapy with metformin, a thiazolidinedione (particularly pioglitazone), a sulphonylurea, a glinide, GLP-1 or GLP-1 analogue, insulin or insulin analogue, or an α-glucosidase inhibitor, or despite dual combination therapy with metformin/sulphonylurea, metformin/thiazolidinedione (particularly pioglitazone), sulphonylurea/α-glucosidase inhibitor, pioglitazone/sulphonylurea, metformin/insulin, pioglitazone/insulin or sulphonylurea/insulin. Thus, in an embodiment, the therapies described herein may be used in patients experienced with therapy, e.g. with conventional oral and/or non-oral antidiabetic mono- or dual or triple combination medication as mentioned herein. In certain embodiments of the therapies of this invention, in such patients the DPP-4 inhibitor (preferably linagliptin) may be used on top of or added on the existing or ongoing conventional oral and/or non-oral antidiabetic mono- or dual or triple combination medication with which such patients are pre-treated or experienced.

For example, a diabetes patient (particularly type 2 diabetes patient, with insufficient glycemic control) of this invention may be treatment-naïve or pre-treated with one or more (e.g. one or two) conventional antidiabetic agents selected from metformin, thiazolidinediones (particularly pioglitazone), sulphonylureas, glinides, α-glucosidase inhibitors (e.g. acarbose, voglibose), and insulin or insulin analogues, such as e.g. pre-treated or experienced with:

metformin, α-glucosidase inhibitor, sulphonylurea or glinide monotherapy, or metformin plus α-glucosidase inhibitor, metformin plus sulphonylurea, metformin plus glinide, α-glucosidase inhibitor plus sulphonylurea, or α-glucosidase inhibitor plus glinide dual combination therapy.

In certain embodiments relating to such treatment-naïve patients, the DPP-4 inhibitor (preferably linagliptin) may be used as monotherapy, or as initial combination therapy such as e.g. with metformin, a thiazolidinedione (particularly pioglitazone), a sulphonylurea, a glinide, an α-glucosidase inhibitor (e.g. acarbose, voglibose), GLP-1 or GLP-1 analogue, or insulin or insulin analogue; preferably as monotherapy.

In certain embodiments relating to such patients pre-treated or experienced with one or two conventional antidiabetic agents, the DPP-4 inhibitor (preferably linagliptin) may be used as add-on combination therapy, i.e. added to an existing or background therapy with the one or two conventional antidiabetics in patients with insufficient glycemic control despite therapy with the one or more conventional antidiabetic agents, such as e.g. as add-on therapy to one or more (e.g. one or two) conventional antidiabetics selected from metformin, thiazolidinediones (particularly pioglitazone), sulphonylureas, glinides, α-glucosidase inhibitors (e.g. acarbose, voglibose), GLP-1 or GLP-1 analogues, and insulin or insulin analogues, such as e.g.:
as add-on therapy to metformin, to a α-glucosidase inhibitor, to a sulphonylurea or to a glinide;
or as add-on therapy to metformin plus α-glucosidase inhibitor, to metformin plus sulphonylurea, to metformin plus glinide, to α-glucosidase inhibitor plus sulphonylurea, or to α-glucosidase inhibitor plus glinide;
or as add-on therapy to an insulin, with or without metformin, a thiazolidinedione (particularly pioglitazone), a sulphonylurea, a glinide or an α-glucosidase inhibitor (e.g. acarbose, voglibose).

An embodiment of the patients which may be amenable to the therapies of this invention may include, without being limited, those diabetes patients for whom normal metformin therapy is less appropriate, such as e.g. those diabetes patients who need reduced dose metformin therapy due to reduced tolerability, intolerability or contraindication against metformin or due to impaired/reduced renal function (e.g. elderly patients, such as e.g. ≥60-65 years).

In a further embodiment, the patient described herein is a subject having diabetes (e.g. type 1 or type 2 diabetes or LADA, particularly type 2 diabetes).

In particular, the subject within this invention may be a human, e.g. human child, a human adolescent or, particularly, a human adult.

In further particular, the subject within this invention is a human type 2 diabetes patient.

In certain embodiments, the subject within this invention is a (human) type 2 diabetes patient in early diabetes stage or, particularly, in advanced diabetes stage. In an embodiment, the patient has long-standing type 2 diabetes (e.g. >10 years) and/or is treated with insulin.

In further certain embodiments, the subject within this invention is a (human) type 2 diabetes patient in early CKD stage or, particularly, in advanced CKD stage.

The enzyme DPP-4 (dipeptidyl peptidase IV) also known as CD26 is a serine protease known to lead to the cleavage of a dipeptide from the N-terminal end of a number of proteins having at their N-terminal end a prolin or alanin residue. Due to this property DPP-4 inhibitors interfere with the plasma level of bioactive peptides including the peptide GLP-1 and are considered to be promising drugs for the treatment of diabetes mellitus.

A particularly preferred DPP-4 inhibitor to be emphasized within the present invention is 1-[(4-methyl-quinazolin-2-Amethyl]-3-methyl-7-(2-butyn-1-yl)-8-(3-(R)-amino-piperidin-1-yl)-xanthine, particularly the free base thereof (which is also known as linagliptin or BI 1356).

The DPP-4 inhibitor of this invention may be selected from the group consisting of linagliptin, sitagliptin, vildagliptin, alogliptin, saxagliptin, teneligliptin, anagliptin, gemigliptin and dutogliptin, or a pharmaceutically acceptable salt of one of the herein mentioned DPP-4 inhibitors, or a prodrug thereof.

DPP-4 is analogous to CD26 a T-cell antigene which plays a role in T-cell activation and immuno-modulation. Further, some substrates of DPP-4 (beyond incretins) may have potential cardio-renal effects.

Furthermore, linagliptin, a selective DPP-4 inhibitor may qualify for the instant purposes with certain anti-oxidative and/or anti-inflammatory features.

Linagliptin may further have a direct impact on the integrity of the endothelium and podocytes of the glomerula and the proximal tubular cells of the kidney as well as on endothelial function and linagliptin has a relatively high tissue distribution, including in the kidney.

Further, samples from human kidneys indicate that proteinuric human diseases (such as e.g. diabetic nephropathy or nephrotic syndrome) seem to be characterized by an upregulation of glomerular DPP-4.

Moreover, linagliptin may further qualify for the instant purposes by antidiabetic and anti-albuminuric effects/usability preferably in type 2 diabetes patients, with micro- or macroalbuminuria (e.g. 30-3000 mg/g creatinine), preferably on top of current standard treatment for diabetic nephropathy (e.g. ACE inhibitor or ARB).

It is further noteworthy that most major DPP-4 inhibitors (e.g. sitagliptin, saxagliptin, alogliptin and vildagliptin) require dose adjustment/reduction in the renally impaired (CKD) population. The DPP-4 inhibitor linagliptin, however, is unique in being secreted via the bile and does not require adjustment of dose with declining renal function.

Additionally, the DPP-4 inhibitor linagliptin can exert anti-fibrotic effects, such as on kidney fibrosis.

A special embodiment of the DPP-4 inhibitors of this invention refers to those orally administered DPP-4 inhibitors which are therapeutically efficacious at low dose levels, e.g. at dose levels<100 mg or <70 mg per patient per day, preferably <50 mg, more preferably <30 mg or <20 mg, even more preferably from 1 mg to 10 mg (if required, divided into 1 to 4 single doses, particularly 1 or 2 single doses, which may be of the same size), particularly from 1 mg to 5 mg (more particularly 5 mg), per patient per day, preferentially, administered orally once-daily, more preferentially, at any time of day, administered with or without food. Thus, for example, the therapeutic daily oral dose 5 mg BI 1356 can be given in a once daily dosing regimen (i.e. 5 mg BI 1356 once daily) or in a twice daily dosing regimen (i.e. 2.5 mg BI 1356 twice daily), at any time of day, with or without food.

The present invention further relates to a pharmaceutical composition or combination comprising or consisting essentially of a certain DPP-4 inhibitor (particularly linagliptin) and metformin (particularly in the form of metformin hydrochloride), optionally in combination or alternation with one or more other therapeutic agents, each as described herein, such as e.g. for simultaneous, sequential or separate medical use in therapy or prophylaxis as described herein.

Within this invention it is to be understood that the combinations or combined uses according to this invention may envisage the simultaneous, sequential or separate administration of the active components.

In this context, "combination" or "combined" within the meaning of this invention may include, without being limited, fixed and non-fixed (e.g. free) forms (including kits, or other administration, application or dosage forms) and uses, such as e.g. the simultaneous, sequential or separate use of the components.

The combined administration or application of this invention may take place by administering the therapeutic components together, such as e.g. by administering them simultaneously in one single or in two separate formulations. Alternatively, the administration may take place by administering the therapeutic components sequentially, such as e.g. successively in two separate formulations.

For the combination therapy of this invention the therapeutic components may be administered separately (which implies that they are formulated separately) or formulated altogether (which implies that they are formulated in the same preparation). Hence, the administration of one element of the combination of the present invention may be prior to, concurrent to, or subsequent to the administration of the other element of the combination.

Unless otherwise noted, combination therapy may refer to first line, second line or third line therapy, or initial or add-on combination therapy or replacement therapy.

Unless otherwise noted, monotherapy may refer to first line therapy (e.g. therapy of patients with insufficient glycemic control by diet and exercise alone, such as e.g. drug-naive patients, typically patients early after diagnosis and/or who have not been previously treated with an antidiabetic agent, and/or patients ineligible for metformin therapy such as e.g. patients for whom metformin therapy is contraindicated, such as e.g. due to renal impairment, or inappropriate, such as e.g. due to intolerance).

Unless otherwise noted, add-on combination therapy may refer to second line or third line therapy (e.g. therapy of patients with insufficient glycemic control despite (diet and exercise plus) therapy with one or two conventional antidiabetic agents, typically patients who are pre-treated with one or two antidiabetic agents, such as e.g. patients with such existing antidiabetic background medication).

Unless otherwise noted, initial combination therapy may refer to first line therapy (e.g. therapy of patients with insufficient glycemic control by diet and exercise alone, such as e.g. drug-naive patients, typically patients early after diagnosis and/or who have not been previously treated with an antidiabetic agent).

A DPP-4 inhibitor according to the invention is preferably administered orally.

In one embodiment, pharmaceutical compositions or fixed dose combinations of a DPP-4 inhibitor (particularly linagliptin) and metformin (particularly in the form of metformin hydrochloride) such as described herein include, without being limited to, such compositions which comprise immediate release metformin and the DPP-4 inhibitor (preferably as an immediate release component). In connection with such compositions, further reference is made for example to WO 2009/121945, the disclosure of which is incorporated herein. Particular reference is made to those tablet forms which are described in more detail in the example section of WO 2009/121945; the mono-layer tablet hereby being preferred.

In another embodiment, pharmaceutical compositions or fixed dose combinations of a DPP-4 inhibitor (particularly linagliptin) and metformin (particularly in the form of metformin hydrochloride) such as described herein include, without being limited to, such compositions which comprise controlled or sustained (e.g. slow or extended) release metformin and the DPP-4 inhibitor (preferably as an immediate release component). Examples of such compositions include, without being limited, drug (DPP-4 inhibitor)-coated tablets (which may be optionally over-coated with a non-functional film-coat), e.g. compositions comprising i) an extended release core comprising metformin and one or more suitable excipients and ii) a (preferably immediate release) film-coating comprising DPP-4 inhibitor (e.g. such as film-coat layer). In connection with such compositions, further reference is made for example to WO 2012/120040, WO 2013/131967 and PCT/EP2015074030, the disclosures of which are incorporated herein. Particular reference is made to the tablet forms as described in more detail in the example section of PCT/EP2015074030. Examples of slow release may include, without being limited, a metformin composition (e.g. as tablet core) where metformin is released at a rate where the peak plasma levels of metformin are typically achieved about 8-22 h after administration.

In more detailed example, a pharmaceutical composition as mentioned herein comprises a certain DPP-4 inhibitor (particularly linagliptin) and metformin (particularly in the form of metformin hydrochloride), and optionally one or more pharmaceutically acceptable auxiliaries.

Pharmaceutically acceptable auxiliaries for the pharmaceutical compositions as described herein may comprise a stabilizer, such as e.g. arginine, particularly L-arginine.

Particularly, a pharmaceutical composition as described herein comprises linagliptin and metformin (particularly in the form of metformin hydrochloride), L-arginine (such as e.g. as inactive ingredient or as stabilizer), and optionally one or more further pharmaceutically acceptable auxiliaries or excipients.

Pharmaceutically acceptable auxiliaries or excipients mentioned herein may comprise optionally in addition to L-arginine other auxiliaries such as e.g. one or more fillers, one or more diluents, one or more binders, one or more lubricants, one or more release agents, one or more disintegrants, one or more breakdown agents, one or more flow agents, one or more coating agents, one or more plasticizers, one or more pigments, etc.

In an embodiment, a pharmaceutical composition as described herein comprises linagliptin (e.g. in an amount of 2.5 mg, such as for twice daily administration, or in an amount of 5 mg, such as for once daily administration) and metformin (particularly in the form of metformin hydrochloride; e.g. in an amount of 500, 750, 850 or 1000 mg; e.g. in immediate release formulation or in extended release formulation), L-arginine (particularly as stabilizer) and optionally one or more other auxiliaries.

In an embodiment, a pharmaceutical composition as described herein comprises linagliptin (e.g. in an amount of 2.5 mg, particularly in immediate release formulation such as for twice daily administration), metformin (particularly metformin hydrochloride, e.g. in an amount of 500, 850 or 1000 mg, particularly in immediate release formulation), L-arginine (particularly as stabilizer), a filler (e.g. maize starch), a binder (e.g. copovidone), and a lubricant (e.g. magnesium stearate) and optionally a flow agent (e.g. anhydrous colloidal silicon dioxide).

In another embodiment of the present invention the tablets mentioned herein include for example single-layer, double-layer or triple-layer tablets, coated core tablets, film-coated tablets, etc.

Typical dosage strengths of the dual fixed dose combination (tablet) of linagliptin/metformin IR (immediate release) are 2.5/500 mg, 2.5/850 mg and 2.5/1000 mg (linagliptin/metformin hydrochloride), which may be administered twice a day.

In a particular embodiment, for use in renally impaired patients according to the present invention, especially for use in patients with (chronic) renal impairment of mild-to-moderate stage (CKD stage 3a) such as having eGFR levels 45-59 or of moderate-to-severe stage such as having eGFR levels 30-44 (CKD stage 3b), a particular dosage strength of linagliptin/metformin IR (immediate release) is 2.5/500 mg (linagliptin/metformin hydrochloride), administered twice daily.

Typical dosage strengths of the dual fixed dose combination (tablet) of linagliptin/metformin XR (extended release) are 5/1000 mg (linagliptin/metformin hydrochloride), which may be administered as one tablet once a day (preferably to be taken in the evening preferably with meal), or 2.5/750 and 2.5/1000 (linagliptin/metformin hydrochloride), which may be administered as two tablets once a day (preferably to be taken in the evening preferably with meal).

In a further embodiment, for use in renally impaired patients according to the present invention, especially for use in patients with (chronic) renal impairment of mild-to-moderate stage (CKD stage 3a) such as having eGFR levels 45-59 or of moderate-to-severe stage such as having eGFR levels 30-44 (CKD stage 3b), a particular dosage strength of linagliptin/metformin XR (extended release) is 5/1000 mg (linagliptin/metformin hydrochloride), administered once daily.

In a particular embodiment, for use in renally impaired patients according to the present invention, especially for use in patients with (chronic) renal impairment of mild-to-moderate stage (CKD stage 3a) such as having eGFR levels 45-59 or of moderate-to-severe stage such as having eGFR levels 30-44 (CKD stage 3b), the maximum daily dose may be 1000 mg metformin hydrochloride, preferably given as two divided doses, such as e.g. 500 mg BID.

Metformin is usually given in doses varying from about 500 mg to 2000 mg up to 2500 mg or 3000 mg per day using various dosing regimens from about 100 mg to 500 mg or 200 mg to 850 mg (1-3 times a day), or about 300 mg to 1000 mg once or twice a day, or delayed-release metformin in doses of about 100 mg to 1000 mg or preferably 500 mg to 1000 mg once or twice a day or about 500 mg to 2000 mg once a day. Particular dosage strengths may be 250, 500, 625, 750, 850 and 1000 mg of metformin hydrochloride.

As different metabolic functional disorders often occur simultaneously, it is quite often indicated to combine a number of different active principles with one another. Thus, depending on the functional disorders diagnosed, improved treatment outcomes may be obtained if a DPP-4 inhibitor or pharmaceutical combination or composition according to this invention is combined with active substances customary for the respective disorders, such as e.g. one or more active substances selected from among the other antidiabetic substances, especially active substances that lower the blood sugar level or the lipid level in the blood, raise the HDL level in the blood, lower blood pressure or are indicated in the treatment of atherosclerosis or obesity.

The DPP-4 inhibitors or pharmaceutical combinations or compositions mentioned herein—besides their use on their own—may also be used in conjunction with other active substances, by means of which improved treatment results can be obtained. Such a combined treatment may be given as a free combination of the substances or in the form of a fixed combination, for example in a tablet or capsule. Pharmaceutical formulations of the combination partner needed for this may either be obtained commercially as pharmaceutical compositions or may be formulated by the skilled man using conventional methods. The active substances which may be obtained commercially as pharmaceutical compositions are described in numerous places in the prior art, for example in the list of drugs that appears annually, the "Rote Liste®" of the federal association of the pharmaceutical industry, or in the annually updated compilation of manufacturers' information on prescription drugs known as the "Physicians' Desk Reference".

Examples of antidiabetic combination partners (such as beyond metformin) are sulphonylureas such as glibenclamide, tolbutamide, glimepiride, glipizide, gliquidon, glibornuride and gliclazide; nateglinide; repaglinide; mitiglinide; thiazolidinediones such as rosiglitazone and pioglitazone; PPAR gamma modulators such as metaglidases; PPAR-gamma agonists such as e.g. rivoglitazone, mitoglitazone, INT-131 and balaglitazone; PPAR-gamma antagonists; PPAR-gamma/alpha modulators such as tesaglitazar, muraglitazar, aleglitazar, indeglitazar and KRP297; PPAR-gamma/alpha/delta modulators such as e.g. lobeglitazone; AMPK-activators such as AICAR; acetyl-CoA carboxylase (ACC1 and ACC2) inhibitors; diacylglycerol-acetyltransferase (DGAT) inhibitors; pancreatic beta cell GCRP agonists such as GPR119 agonists (SMT3-receptor-agonists); 11β-HSD-inhibitors; FGF19 agonists or analogues; alpha-glucosidase blockers such as acarbose, voglibose and miglitol; alpha2-antagonists; insulin and insulin analogues such as human insulin, insulin lispro, insulin glusilin, r-DNA-insulinaspart, NPH insulin, insulin detemir, insulin degludec, insulin tregopil, insulin zinc suspension and insulin glargin; Gastric inhibitory Peptide (GIP); amylin and amylin analogues (e.g. pramlintide or davalintide); GLP-1 and GLP-1 analogues such as Exendin-4, e.g. exenatide, exenatide LAR, liraglutide, taspoglutide, lixisenatide (AVE-0010), LY-2428757 (a PEGylated version of GLP-1), dulaglutide (LY-2189265), semaglutide or albiglutide; SGLT2-inhibitors such as e.g. dapagliflozin, sergliflozin (KGT-1251), atigliflozin, canagliflozin, ipragliflozin, luseogliflozin or tofogliflozin; inhibitors of protein tyrosine-phosphatase (e.g. trodusquemine); inhibitors of glucose-6-phosphatase; fructose-1,6-bisphosphatase modulators; glycogen phosphorylase modulators; glucagon receptor antagonists; phosphoenolpyruvatecarboxykinase (PEPCK) inhibitors; pyruvate dehydrogenasekinase (PDK) inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976) or of serine/threonine kinases; glucokinase/regulatory protein modulators incl. glucokinase activators; glycogen synthase kinase inhibitors; inhibitors of the SH2-domain-containing inositol 5-phosphatase type 2 (SHIP2); IKK inhibitors such as high-dose salicylate; JNK1 inhibitors; protein kinase C-theta inhibitors; beta 3 agonists such as ritobegron, YM 178, solabegron, talibegron, N-5984, GRC-1087, rafabegron, FMP825; aldosereductase inhibitors such as 3201, zenarestat, fidarestat, epalrestat, ranirestat, NZ-314, CP-744809, and CT-112; SGLT-1 or SGLT-2 inhibitors; KV 1.3 channel inhibitors; GPR40 modulators such as e.g. [(3S)-6-({2',6'-dimethyl-4'-[3-(methylsulfonyl)propoxy]biphenyl-3-yl}methoxy)-2,3-dihydro-1-benzofuran-3-yl]acetic acid; SCD-1 inhibitors; CCR-2 antagonists; dopamine receptor agonists (bromocriptine mesylate [Cycloset]); 4-(3-(2,6-dimethylbenzyloxy)phenyl)-4-oxobutanoic acid; sirtuin stimulants; and other DPP IV inhibitors.

A dosage of pioglitazone is usually of about 1-10 mg, 15 mg, 30 mg, or 45 mg once a day.

Rosiglitazone is usually given in doses from 4 to 8 mg once (or divided twice) a day (typical dosage strengths are 2, 4 and 8 mg).

Glibenclamide (glyburide) is usually given in doses from 2.5-5 to 20 mg once (or divided twice) a day (typical dosage strengths are 1.25, 2.5 and 5 mg), or micronized glibenclamide in doses from 0.75-3 to 12 mg once (or divided twice) a day (typical dosage strengths are 1.5, 3, 4.5 and 6 mg).

Glipizide is usually given in doses from 2.5 to 10-20 mg once (up to 40 mg divided twice) a day (typical dosage strengths are 5 and 10 mg), or extended-release glipizide in doses from to 10 mg (up to 20 mg) once a day (typical dosage strengths are 2.5, 5 and 10 mg).

Glimepiride is usually given in doses from 1-2 to 4 mg (up to 8 mg) once a day (typical dosage strengths are 1, 2 and 4 mg).

A dual combination of glibenclamide/metformin is usually given in doses from 1.25/250 once daily to 10/1000 mg twice daily (typical dosage strengths are 1.25/250, 2.5/500 and 5/500 mg).

A dual combination of glipizide/metformin is usually given in doses from 2.5/250 to 10/1000 mg twice daily (typical dosage strengths are 2.5/250, 2.5/500 and 5/500 mg).

A dual combination of glimepiride/metformin is usually given in doses from 1/250 to 4/1000 mg twice daily.

A dual combination of rosiglitazone/glimepiride is usually given in doses from 4/1 once or twice daily to 4/2 mg twice daily (typical dosage strengths are 4/1, 4/2, 4/4, 8/2 and 8/4 mg).

A dual combination of pioglitazone/glimepiride is usually given in doses from 30/2 to 30/4 mg once daily (typical dosage strengths are 30/4 and 45/4 mg).

A dual combination of rosiglitazone/metformin is usually given in doses from 1/500 to 4/1000 mg twice daily (typical dosage strengths are 1/500, 2/500, 4/500, 2/1000 and 4/1000 mg).

A dual combination of pioglitazone/metformin is usually given in doses from 15/500 once or twice daily to 15/850 mg thrice daily (typical dosage strengths are 15/500 and 15/850 mg).

The non-sulphonylurea insulin secretagogue nateglinide is usually given in doses from 60 to 120 mg with meals (up to 360 mg/day, typical dosage strengths are 60 and 120 mg); repaglinide is usually given in doses from 0.5 to 4 mg with meals (up to 16 mg/day, typical dosage strengths are 0.5, 1 and 2 mg). A dual combination of repaglinide/metformin is available in dosage strengths of 1/500 and 2/850 mg.

Acarbose is usually given in doses from 25 to 100 mg with meals (up to 300 mg/day, typical dosage strengths are 25, 50 and 100 mg). Miglitol is usually given in doses from 25 to 100 mg with meals (up to 300 mg/day, typical dosage strengths are 25, 50 and 100 mg).

Conventional antidiabetics and antihyperglycemics typically used in mono- or dual or triple (add-on or initial) combination therapy may include, without being limited to, metformin, sulphonylureas, thiazolidinediones, glinides, alpha-glucosidase blockers, GLP-1 and GLP-1 analogues, as well as insulin and insulin analogues, such as e.g. those agents indicated herein by way of example, including combinations thereof.

Examples of combination partners that lower the lipid level in the blood are HMG-CoA-reductase inhibitors such as simvastatin, atorvastatin, lovastatin, fluvastatin, pravastatin, pitavastatin and rosuvastatin; fibrates such as bezafibrate, fenofibrate, clofibrate, gemfibrozil, etofibrate and etofyllinclofibrate; nicotinic acid and the derivatives thereof such as acipimox; PPAR-alpha agonists; PPAR-delta agonists such as e.g. {4-[(R)-2-ethoxy-3-(4-trifluoromethyl-phenoxy)-propylsulfanyl]-2-methyl-phenoxy}-acetic acid; PPAR-alpha/delta agonists; inhibitors of acyl-coenzyme A:cholesterolacyltransferase (ACAT; EC 2.3.1.26) such as avasimibe; cholesterol resorption inhibitors such as ezetimib; substances that bind to bile acid, such as cholestyramine, colestipol and colesevelam; inhibitors of bile acid transport; HDL modulating active substances such as D4F, reverse D4F, LXR modulating active substances and FXR modulating active substances; CETP inhibitors such as torcetrapib, JTT-705 (dalcetrapib) or compound 12 from WO 2007/005572 (anacetrapib); LDL receptor modulators; MTP inhibitors (e.g. lomitapide); and ApoB100 antisense RNA.

A dosage of atorvastatin is usually from 1 mg to 40 mg or 10 mg to 80 mg once a day.

Examples of combination partners that lower blood pressure are beta-blockers such as atenolol, bisoprolol, celiprolol, metoprolol and carvedilol; diuretics such as hydrochlorothiazide, chlortalidon, xipamide, furosemide, piretanide, torasemide, spironolactone, eplerenone, amiloride and triamterene; calcium channel blockers such as amlodipine, nifedipine, nitrendipine, nisoldipine, nicardipine, felodipine, lacidipine, lercanipidine, manidipine, isradipine, nilvadipine, verapamil, gallopamil and diltiazem; ACE inhibitors such as ramipril, lisinopril, cilazapril, quinapril, captopril, enalapril, benazepril, perindopril, fosinopril and trandolapril; as well as angiotensin II receptor blockers (ARBs) such as telmisartan, candesartan, valsartan, losartan, irbesartan, olmesartan, azilsartan and eprosartan.

A dosage of telmisartan is usually from 20 mg to 320 mg or 40 mg to 160 mg per day.

Examples of combination partners which increase the HDL level in the blood are Cholesteryl Ester Transfer Protein (CETP) inhibitors; inhibitors of endothelial lipase; regulators of ABC1; LXRalpha antagonists; LXRbeta agonists; PPAR-delta agonists; LXRalpha/beta regulators, and substances that increase the expression and/or plasma concentration of apolipoprotein A-I.

Examples of combination partners for the treatment of obesity are sibutramine; tetrahydrolipstatin (orlistat); alizyme (cetilistat); dexfenfluramine; axokine; cannabinoid receptor 1 antagonists such as the CB1 antagonist rimonobant; MCH-1 receptor antagonists; MC4 receptor agonists; NPY5 as well as NPY2 antagonists (e.g. velneperit); beta3-AR agonists such as SB-418790 and AD-9677; 5HT2c receptor agonists such as APD 356 (lorcaserin); myostatin inhibitors; Acrp30 and adiponectin; steroyl CoA desaturase (SCD1) inhibitors; fatty acid synthase (FAS) inhibitors; CCK receptor agonists; Ghrelin receptor modulators; Pyy 3-36; orexin receptor antagonists; and tesofensine; as well as the dual combinations bupropion/naltrexone, bupropion/zonisamide, topiramate/phentermine and pramlintide/metreleptin.

Examples of combination partners for the treatment of atherosclerosis are phospholipase A2 inhibitors; inhibitors of tyrosine-kinases (50 mg to 600 mg) such as PDGF-receptor-kinase (cf. EP-A-564409, WO 98/35958, U.S. Pat. No. 5,093,330, WO 2004/005281, and WO 2006/041976); oxLDL antibodies and oxLDL vaccines; apoA-1 Milano; ASA; and VCAM-1 inhibitors.

Further, the certain DPP-4 inhibitor of this invention may be used in combination with a substrate of DPP-4 (particularly with an anti-inflammatory substrate of DPP-4), which may be other than GLP-1, for the purposes according to the present invention, such substrates of DPP-4 include, for example—without being limited to, one or more of the following:

Incretins:
Glucagon-like peptide (GLP)-1
Glucose-dependent insulinotropic peptide (GIP)
Neuroactive:
Substance P
Neuropeptide Y (NPY)
Peptide YY
Energy homeostasis:
GLP-2
Prolactin
Pituitary adenylate cyclase activating peptide (PACAP)
Other hormones:
PACAP 27
Human chorionic gonadotrophin alpha chain
Growth hormone releasing factor (GHRF)
Luteinizing hormone alpha chain
Insulin-like growth factor (IGF-1)
CCL8/eotaxin
CCL22/macrophage-derived chemokine
CXCL9/interferon-gamma-induced monokine
Chemokines:
CXCL10/interferon-gamma-induced protein-10
CXCL11/interferon-inducible T cell a chemoattractant
CCL3L1/macrophage inflammatory protein 1alpha isoform
LD78beta
CXCL12/stromal-derived factor 1 alpha and beta
Other:
Enkephalins, gastrin-releasing peptide, vasostatin-1,
peptide histidine methionine, thyrotropin alpha Further or in addition, the certain DPP-4 inhibitor of this invention may be used in combination with one or more active substances which are indicated in the treatment of nephropathy, such as selected from diuretics, ACE inhibitors and/or ARBs.

Further or in addition, the certain DPP-4 inhibitor of this invention may be used in combination with one or more active substances which are indicated in the treatment or prevention of cardiovascular diseases or events (e.g. major cardiovascular events).

Moreover, optionally in addition, the certain DPP-4 inhibitor of this invention may be used in combination with one or more antiplatelet agents, such as e.g. (low-dose) aspirin (acetylsalicylic acid), a selective COX-2 or nonselective COX-1/COX-2 inhibitor, or a ADP receptor inhibitor, such as a thienopyridine (e.g. clopidogrel or prasugrel), elinogrel or ticagrelor, or a thrombin receptor antagonist such as vorapaxar.

Yet moreover, optionally in addition, the certain DPP-4 inhibitor of this invention may be used in combination with one or more anticoagulant agents, such as e.g. heparin, a coumarin (such as warfarin or phenprocoumon), a pentasaccharide inhibitor of Factor Xa (e.g. fondaparinux), or a direct thrombin inhibitor (such as e.g. dabigatran), or a Faktor Xa inhibitor (such as e.g. rivaroxaban or apixaban or edoxaban or otamixaban).

Still yet moreover, optionally in addition, the certain DPP-4 inhibitor of this invention may be used in combination with one or more agents for the treatment of heart failure (such as e.g. those mentioned in WO 2007/128761).

The dosage of the active components in the combinations or compositions in accordance with the present invention may be varied, although the amount of the active ingredients shall be such that a suitable dosage form is obtained. Hence, the selected dosage and the selected dosage form shall depend on the desired therapeutic effect, the route of administration and the duration of the treatment. Dosage ranges for the combination may be from the maximal tolerated dose for the single agent to lower doses.

The present invention is not to be limited in scope by the specific embodiments described herein. Various modifications of the invention in addition to those described herein may become apparent to those skilled in the art from the present disclosure. Such modifications are intended to fall within the scope of the appended claims.

Further embodiments, features and advantages of the present invention may become apparent from the following examples. The following examples serve to illustrate, by way of example, the principles of the invention without restricting it.

All patent applications cited herein are hereby incorporated by reference in their entireties.

EXAMPLES

In order that this invention be more fully understood, the herein-given examples are set forth. Further embodiments, features or aspects of the present invention may become apparent from the examples. The examples serve to illustrate, by way of example, the principles of the invention without restricting it.

Treatment of Patients with Type 2 Diabetes Mellitus Having Albuminuria

A multicentre, double-blind, placebo-controlled clinical trial investigates glycaemic and renal effects of linagliptin in patients with type 2 diabetes, albuminuria and estimated GFR≥30 ml/min/1.73 m$^2$ (with or without renal function impairment).

A total of 360 patients with type 2 diabetes (HbA1c 6.5-10%) and persistent albuminuria (urinary albumin-to-creatinine ratio [UACR] 30-3000 mg/gCr; i.e. micro- or macro-albuminuria) despite stable background (standard-of-care) of single renin-angiotensin system blockade (ARB or ACE inhibitor) are randomised to either linagliptin 5 mg (n=182) or placebo (n=178) for 24 weeks. Primary glycaemic and key secondary renal surrogate endpoints are HbA1c and UACR change from baseline over 24 weeks, respectively.

Overall mean (SD) baseline HbA1c and geometric mean (gMean) UACR are 7.8% (0.9) and 126 mg/gCr (microalbuminuria, 73.7%; macroalbuminuria, 20.3%), respectively. At week 24, the adjusted mean (SE) % change from baseline in HbA1c for linagliptin and placebo is −0.63 (0.06) and −0.03 (0.06), respectively; the placebo-adjusted mean HbA1c change from baseline is −0.60% (95% CI −0.78, −0.43; p<0.0001). The gMean for time-weighted average of % change (95% Cl) from baseline in UACR over 24 weeks for linagliptin and placebo is −11.0% (−16.8, −4.7) and −5.1% (−11.4, 1.6), respectively; the placebo-adjusted gMean for time-weighted average of % change in UCAR from baseline is −6.0% (95% Cl −15.0, 3.0; NS).

Exploratory analyses of the subgroup of patients treated with linagliptin on a background of metformin (as well as of those with moderate renal impairment CKD3, eGFR of 30-60 ml/min/1.73 m$^2$) in the above study show a numerically larger difference in the changes from baseline vs. placebo in urinary albumin to creatinine ratio (UACR) compared to patients without the combination with metformin (post hoc subgroup analysis of key secondary endpoint).

Alternatively, the renal effects can be evaluated by a scoring system (diabetic nephropathy score) for staging diabetic kidney disease such as generated from the profiles of a urinary biomarker panel composed of alpha2-HS-glycoprotein, alpha-1-antitrypsin and acid-1-glycoprotein.

Treatment of Patients with Type 2 Diabetes Mellitus at High Cardiovascular and Renal Microvascular Risk:

The long term impact on cardiovascular and renal (microvascular) safety, morbidity and/or mortality and relevant efficacy parameters (e.g. HbA1c, fasting plasma glucose, treatment sustainability) of treatment with linagliptin in combination with metformin in a relevant population of patients with type 2 diabetes mellitus (such as e.g. at high vascular risk, at advanced stage of diabetic kidney disease) can be investigated as follows:

Type 2 diabetes patient with insufficient glycemic control (naïve or pre-treated with any antidiabetic background medication including metformin, excluding treatment with GLP-1 receptor agonists, DPP-4 inhibitors or SGLT-2 inhibitors if consecutive 7 days, e.g. having HbA1c 6.5-10%), and high risk of cardiovascular events, e.g. defined by:
  albuminuria (micro or macro) and previous macrovascular disease: e.g. defined according to Condition I as indicated below;
  and/or
  impaired renal function: e.g. as defined according to Condition II as indicated below;
Condition I:
albuminuria (such as e.g. urine albumin creatinine ratio (UACR)≥30 mg/g creatinine or ≥30 mg/l (milligram albumin per liter of urine) or ≥30 μg/min (microgram albumin per minute) or ≥30 mg/24 h (milligram albumin per 24 hours)) and
previous macrovascular disease, such as e.g. defined as one or more of a) to f):
a) previous myocardial infarction (e.g. >2 months),
b) advanced coronary artery disease, such as e.g. defined by any one of the following:
  ≥50% narrowing of the luminal diameter in 2 or more major coronary arteries (e.g. LAD (Left Anterior Descending), CX (Circumflex) or RCA (Right Coronary Artery)) by coronary angiography or CT angiography,
  left main stem coronary artery with ≥50% narrowing of the luminal diameter,
  prior percutaneous or surgical revascularization of ≥2 major coronary arteries (e.g. ≥2 months),
  combination of prior percutaneous or surgical revascularization, such as e.g. of 1 major coronary artery (e.g. ≥2 months) and ≥50% narrowing of the luminal diameter by coronary angiography or CT angiography of at least 1 additional major coronary artery,
c) high-risk single-vessel coronary artery disease, such as e.g. defined as the presence of ≥50% narrowing of the luminal diameter of one major coronary artery (e.g. by coronary angiography or CT angiography in patients not revascularised) and at least one of the following:
  a positive non invasive stress test, such as e.g. confirmed by either:
    a positive ECG exercise tolerance test in patients without left bundle branch block, Wolff-Parkinson-White syndrome, left ventricular hypertrophy with repolarization abnormality, or paced ventricular rhythm, atrial fibrillation in case of abnormal ST-T segments,
    a positive stress echocardiogram showing induced regional systolic wall motion abnormalities,
    a positive nuclear myocardial perfusion imaging stress test showing stress induced reversible perfusion abnormality,
  patient discharged from hospital with a documented diagnosis of unstable angina pectoris (e.g. ≥2-12 months),
d) previous ischemic or haemorrhagic stroke (e.g. >3 months),
e) presence of carotid artery disease (e.g. symptomatic or not), such as e.g. documented by either:
  imaging techniques with at least one lesion estimated to be ≥50% narrowing of the luminal diameter,
  prior percutaneous or surgical carotid revascularization,
f) presence of peripheral artery disease, such as e.g. documented by either:
  previous limb angioplasty, stenting or bypass surgery,
  previous limb or foot amputation due to macrocirculatory insufficiency,
  angiographic evidence of peripheral artery stenosis≥50% narrowing of the luminal diameter in at least one limb (e.g. definition of peripheral artery: common iliac artery, internal iliac artery, external iliac artery, femoral artery, popliteal artery),
Condition II:
  impaired renal function (e.g. with or without CV co-morbidities), such as e.g. defined by:
    impaired renal function (e.g. as defined by MDRD formula) with an estimated glomerular filtration rate (eGFR) 15-45 mL/min/1.73 m$^2$ with any urine albumin creatinine ratio (UACR), and/or
    impaired renal function (e.g. as defined by MDRD formula) with an with an estimated glomerular filtration rate (eGFR)≥45-75 mL/min/1.73 m$^2$ with an urine albumin creatinine ratio (UACR)>200 mg/g creatinine or >200 mg/l (milligram albumin per liter of urine) or >200 μg/min (microgram albumin per minute) or >200 mg/24 h (milligram albumin per 24 hours);
  are treated over a lengthy period (e.g. for 4-5 years, or preferably at least 48 months) with linagliptin (preferably 5 mg per day, administered orally) in combination with metformin (optionally in combination with one or more further active substances, e.g. such as those described herein) and compared with patients who have been treated with placebo (as add-on therapy on top of standard of care).

Evidence of the therapeutic success compared with patients who have been treated with placebo can be found in non-inferiority or superiority compared to placebo, e.g. in the (longer) time taken to first occurrence of cardio- or cerebrovascular events, e.g. time to first occurrence of any of the following components of the composite CV endpoint: cardiovascular death (including fatal stroke, fatal myocardial infarction and sudden death), non-fatal myocardial infarction (excluding silent myocardial infarction), non-fatal stroke, and (optional) hospitalization e.g. for unstable angina pectoris; and/or in the (longer) time taken to first occurrence of renal microvascular events, e.g. time to first occurrence of any of the following components of the composite renal endpoint: renal death, sustained end-stage renal disease, and sustained decrease of 50% or more in eGFR.

Further therapeutic success can be found in the (smaller) number of or in the (longer) time taken to first occurrence of any of: cardiovascular death, (non)-fatal myocardial infarction, silent MI, (non)-fatal stroke, hospitalization for unstable angina pectoris, hospitalization for coronary revascularization, hospitalization for peripheral revascularization, hospitalization for congestive heart failure, all cause mortality, renal death, sustained end-stage renal disease, loss in eGFR, new incidence of macroalbuminuria, progression in albuminuria, progression in CKD, need for anti-retinopathy therapy; or improvement in albuminuria, renal function, CKD; or improvement in cognitive function or prevention of/protection against accelerated cognitive decline.

Cognitive functions can be assessed by standardized tests as measure of cognitive functioning such as e.g. by using the Mini-Mental State Examination (MMSE), the Trail Making Test (TMT) and/or the Verbal Fluency Test (VFT).

Additional therapeutic success (compared to placebo) can be found in greater change from baseline in HbA1c and/or FPG.

Further additional therapeutic success can be found in greater proportion of patients on study treatment at study end maintain glycemic control (e.g. HbA1c</=7%).

Further additional therapeutic success can be found in greater proportion of patients on study treatment who at study end maintain glycemic control without need for additional antidiabetic medication (during treatment) to obtain HbA1c</=7%.

Further additional therapeutic success can be found in lower proportion of patients on study treatment initiated on insulin or treated with insulin or in lower dose of insulin dose used.

Further additional therapeutic success can be found in lower change from baseline in body weight or greater proportion of patients with ≤2% weight gain or lower proportion of patients with ≥2% weight gain at study end.

Respective subgroup analysis may be made in this study for patients having chronic kidney disease (CKD) such as e.g. up to stage 3 and/or having estimated glomerular filtration rate (eGFR; mL/minute/1.73 m$^2$) levels down to 45, or down to 30, such as for patients with (chronic) renal impairment of moderate stage (CKD stage 3, eGFR 30-60), particularly of mild-to-moderate stage (CKD stage 3a) such as having eGFR levels 45-59 or of moderate-to-severe stage (CKD stage 3b) such as having eGFR levels 30-44; optionally with or without micro- or macroalbuminuria.

The invention claimed is:

1. A method for treating a type 2 diabetes patient having estimated glomerular filtration rate (eGFR) levels down to 30 mL/minute/1.73 m$^2$, comprising administering to the patient an effective amount of linagliptin, or a pharmaceutically acceptable salt thereof, in combination with metformin, and optionally one or more further active agents selected from the group consisting of insulin and a sulfonylurea; wherein
the patient has both albuminuria and previous macrovascular disease.

2. The method of claim 1, wherein the type 2 diabetes patient has an eGFR level down to 45 mL/minute/1.73 m$^2$.

3. The method of claim 2, wherein linagliptin and metformin are administered in a single pharmaceutical composition.

4. The method of claim 3, wherein the linagliptin is present in the composition in a dosage strength of 2.5 mg; or of 5 mg.

5. The method of claim 4, wherein the metformin is present in the composition in a dosage strength of 500 mg, 850 mg or 1000 mg in the form of immediate release metformin; or 500 mg, 750 mg, 1000 mg, 1500 mg or 2000 mg in the form of extended release metformin.

6. The method of claim 3, wherein the pharmaceutical composition comprises 2.5 mg of linagliptin and 500 mg, 850 mg or 1000 mg of metformin in immediate release form, and optionally one or more pharmaceutically auxiliaries.

7. The method of claim 3, wherein the pharmaceutical composition comprises 5 mg of linagliptin and 1000 mg of metformin in extended release form, and optionally one or more pharmaceutically auxiliaries, or
the pharmaceutical composition comprises 2.5 mg of linagliptin and 750 mg or 1000 mg of metformin in an extended release form, and optionally one or more pharmaceutically auxiliaries.

8. The method of claim 1, wherein linagliptin is administered in a total oral daily dose of 5 mg.

9. The method of claim 1, wherein linagliptin is administered in a total oral daily dose of 5 mg, wherein the 5 mg daily dose is administered as 2.5 mg linagliptin twice daily or 5 mg linagliptin once daily.

10. A method of treating a type 2 diabetes patient having eGFR level 30-44 mL/minute/1.73 m$^2$, comprising administering to the patient an effective amount of linagliptin, or a pharmaceutically acceptable salt thereof, in combination with metformin,
wherein linagliptin and metformin are administered in a single oral dosage form comprising 2.5 mg linagliptin and 500 mg metformin, and optionally one or more pharmaceutically auxiliaries, and
wherein the single oral dosage form is administered orally twice daily to the patient, and wherein
the patient has both albuminuria and previous macrovascular disease.

11. The method of claim 1, wherein the patient has an eGFR of 30-60 mL/minute/1.73 m$^2$.

12. The method of claim 1, wherein the patient has an eGFR of 45-59 mL/minute/1.73 m$^2$.

13. The method of claim 1, wherein the patient has an eGFR of 30-44 mL/minute/1.73 m$^2$.

14. The method of claim 1 wherein the patient has:
renal impairment with an eGFR≥45-75 mL/min/1.73 m$^2$ with macro-albuminuria.

15. The method of claim 1 wherein the patient has:
i) albuminuria defined as urine albumin creatinine ratio (UACR)≥30 mg/g creatinine or ≥30 mg/l (milligram albumin per liter of urine) or ≥30 µg/min (microgram albumin per minute) or ≥30 mg/24 h (milligram albumin per 24 hours) and a previous macrovascular disease defined as one or more of a) to f):
a) previous myocardial infarction,
b) advanced coronary artery disease, c) high-risk single-vessel coronary artery disease,
d) previous ischemic or haemorrhagic stroke,
e) presence of carotid artery disease,
f) presence of peripheral artery disease;
and/or
ii) impaired renal function defined by:
   impaired renal function defined by MDRD formula with an eGFR [15 or] 30-45 mL/min/1.73 m$^2$ with any urine albumin creatinine ratio (UACR), or impaired renal function defined by MDRD formula with an eGFR≥45-75 mL/min/1.73 m$^2$ with an urine albumin creatinine ratio (UACR)>200 mg/g creatinine or >200 mg/l (milligram albumin per liter of urine) or >200 μg/min (microgram albumin per minute) or >200 mg/24 h (milligram albumin per 24 hours).

16. The method of claim 1, further comprising administering to the patient an active substance that lowers blood pressure.

17. The method of claim 1, further comprising administering to the patient an active substance that lowers the lipid level in the blood.

18. The method of claim 1, further comprising administering aspirin to the patient.

* * * * *

UNITED STATES PATENT AND TRADEMARK OFFICE
CERTIFICATE OF CORRECTION

PATENT NO. : 12,364,700 B2
APPLICATION NO. : 18/230693
DATED : July 22, 2025
INVENTOR(S) : Thomas Meinicke et al.

Page 1 of 1

It is certified that error appears in the above-identified patent and that said Letters Patent is hereby corrected as shown below:

On the Title Page

In Column 1, after Item (22), add Item (30) and the following priority details:
--(30) Foreign Application Priority Data
Jun. 10, 2016 (EP) .......................... 16174075
Feb. 1, 2017 (EP) ........................... 17154248--

Signed and Sealed this
Twenty-first Day of October, 2025

John A. Squires
*Director of the United States Patent and Trademark Office*